United States Patent [19]

Tsujihara et al.

[11] Patent Number: 5,677,470

[45] Date of Patent: Oct. 14, 1997

[54] BACCATIN DERIVATIVES AND PROCESSES FOR PREPARING THE SAME

[75] Inventors: Kenji Tsujihara, Urawa; Tomiki Hashiyama, Washimiya-machi; Naoyuki Harada, Urawa; Kunihiko Ozaki, Higashimurayama; Motoaki Ohashi, Koganei; Noriyuki Nakanishi, Kawaguchi; Tetsuo Yamaguchi, Osaka, all of Japan

[73] Assignee: Tanabe Seiyaku Co., Ltd., Osaka, Japan

[21] Appl. No.: 480,052

[22] Filed: Jun. 7, 1995

[30] Foreign Application Priority Data

| Jun. 28, 1994 | [JP] | Japan | 6-145843 |
| Jun. 28, 1994 | [JP] | Japan | 6-145844 |
| Feb. 28, 1995 | [JP] | Japan | 7-039480 |

[51] Int. Cl.$^6$ .............................................. C07D 305/14
[52] U.S. Cl. ........................................ 549/510; 549/511
[58] Field of Search ................................ 549/510, 511

[56] References Cited

U.S. PATENT DOCUMENTS

| 4,814,470 | 3/1989 | Colin | 514/449 |
| 4,857,653 | 8/1989 | Colin et al. | 549/511 |
| 4,924,012 | 5/1990 | Colin et al. | 549/510 |
| 4,960,790 | 10/1990 | Stella et al. | 514/449 |
| 5,059,699 | 10/1991 | Kingston et al. | 549/511 |
| 5,272,171 | 12/1993 | Ueda et al. | 514/449 |
| 5,283,253 | 2/1994 | Holton et al. | 514/444 |
| 5,284,865 | 2/1994 | Holton et al. | 514/449 |
| 5,352,806 | 10/1994 | Gunawardana et al. | 549/510 |
| 5,470,866 | 11/1995 | Kingston et al. | 514/376 |

FOREIGN PATENT DOCUMENTS

| 0336841A1 | 10/1989 | European Pat. Off. |
| 0473326A1 | 3/1992 | European Pat. Off. |
| 0590267 | 4/1994 | European Pat. Off. |
| 0604910 | 7/1994 | European Pat. Off. |
| 0624377A2 | 11/1994 | European Pat. Off. |
| 0629701 | 12/1994 | European Pat. Off. |
| 0639577 | 2/1995 | European Pat. Off. |
| 0671399A1 | 9/1995 | European Pat. Off. |
| 60-013776 | 1/1985 | Japan. |
| 60-013775 | 1/1985 | Japan. |
| 94051689 | 2/1988 | Japan. |
| 130577 | 12/1989 | Japan. |
| 3015398 | 1/1991 | Japan. |
| 94004607 | 1/1994 | Japan. |
| 6504771 | 6/1994 | Japan. |
| 6-1782 | 11/1994 | Japan. |
| WO90/10443 | 9/1990 | WIPO. |
| WO93/06079 | 4/1993 | WIPO. |
| WO93/10076 | 5/1993 | WIPO. |
| WO94/00156 | 1/1994 | WIPO. |
| WO94/07879 | 4/1994 | WIPO. |
| WO94/10997 | 5/1994 | WIPO. |
| WO94/14787 | 7/1994 | WIPO. |
| WO94/15929 | 7/1994 | WIPO. |
| WO94/15599 | 7/1994 | WIPO. |
| WO94/18164 | 8/1994 | WIPO. |
| WO94/18186 | 8/1994 | WIPO. |
| WO94/17052 | 8/1994 | WIPO. |
| WO94/17051 | 8/1994 | WIPO. |
| WO94/17050 | 8/1994 | WIPO. |
| WO94/21251 | 9/1994 | WIPO. |
| WO94/21250 | 9/1994 | WIPO. |
| WO94/20485 | 9/1994 | WIPO. |
| WO94/20088 | 9/1994 | WIPO. |
| WO94/21623 | 9/1994 | WIPO. |
| WO94/21651 | 9/1994 | WIPO. |
| WO95/04154 | 2/1995 | WIPO. |
| WO95/03265 | 2/1995 | WIPO. |
| WO95/11247 | 4/1995 | WIPO. |
| WO95/13271 | 5/1995 | WIPO. |
| WO95/20582 | 8/1995 | WIPO. |
| WO95/25728 | 9/1995 | WIPO. |

OTHER PUBLICATIONS

Derwent Abstract of EP 558959, published Sep. 1993.
Derwent Abstract of EP 253739, published Jan. 1988.
Derwent Abstract of EP 253,738, published Jan, 1988.
Derwent Abstract of JP 60.013775, published Jan. 1985.
Derwent Abstract of JP 60.013776, published Jan. 1985.
Derwent Abstract of EP 362,556, published Nov. 1994.
Derwent Abstract of EP 558,623, published Sep. 1993.
Derwent Abstract of EP 336,841, published May 1993.
"Dictionary of Organic Compounds", Executive Director J. Buckingham, 5th edition, p. 506, 1982.
M. Suffness, "Chapter 32. Taxol: From Discovery to Therapeutic Use," *Annual Reports in Medicinal Chemistry*, vol. 28, pp. 305–314 (1993).
J.N. Denis et al., "A Highly Efficient, Practical Approach to Natural Taxol," *J. Am. Chem. Soc.*, vol. 110, pp. 5917–5919 (1988).

(List continued on next page.)

*Primary Examiner*—Ba K. Trinh
*Attorney, Agent, or Firm*—Finnegan, Henderson, Farabow, Garrett & Dunner, L.L.P.

[57] ABSTRACT

Disclosed are 13α-(3-substituted-2-hydroxypropionyloxy) baccatin compounds represented by the formula:

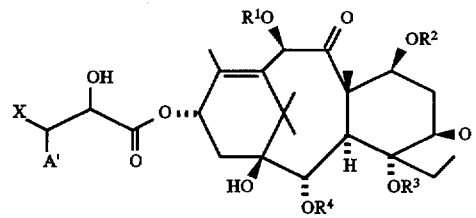

wherein $R^1$ represents a lower alkanoyl group or a protective group for hydroxy group; $R^2$ represents a protective group for hydroxy group; $R^3$ represents a lower alkanoyl group; $R^4$ represents a substituted or unsubstituted benzoyl group; X represents a substituted or unsubstituted aryl group, a substituted or unsubstituted lower alkenyl group, or a substituted or unsubstituted lower alkynyl group; and A' represents a halogen atom, azido group or amino group, and processes for preparing the same.

22 Claims, No Drawings

OTHER PUBLICATIONS

A. Commercon et al., "Improved Protection and Esterification of a Precursor of the Taxotere ®and Taxol Side Chains," *Tetrahedron Letters*, vol. 33, No. 36, pp. 5185–5188 (1992).

T. C. Boge et al., "The Effect of the Aromatic Rings of Taxol on Biological Activity and Solution Conformation: Synthesis and Evaluation of Saturated Taxol and Taxotere Analoques," *J. Med. Chem.*, vol. 37, pp. 3337–3343 (1994).

A. Mori et al., "Asymmetric Simmons–Smith Reactions Using Homochiral Protecting Groups," *Tetrahedron*, vol. 42, No. 23, pp. 6447–6458 (1986).

L. Li et al., "Synthesis and Biological Evaluation of C–3'–Modified Analogs of 9 (R) –Dihydrotaxol," *J. Med. Chem.*, vol. 37, pp. 2655–2663 (1984).

I. Ojima et al., "Synthesis and Structure–Activity Relationships of New Antitumor Taxoids, Effects of Cyclohexyl Substitution at the C–3' and/or C–2 of Taxotere (Docetaxel)," *J. Med. Chem.*, vol. 37, pp. 2602–2608 (1994).

J.N. Denis et al., "An Efficient, Enantioselective Synthesis of the Taxol Side Chain," *J. Org. Chem.*, vol. 51, pp. 46–50 (1986).

K.C. Nicolaou et al., "Design, Synthesis and Biological Activity of Protaxois," *Nature*, vol. 364, pp. 464–466, (Jul. 29, 1993).

L. Mangatal et al., "Application of the Vicinal Oxyamination Reaction With Asymmetric Induction to the Hemisynthesis of Taxol and Analogues," *Tetrahedron*, vol. 45, No. 13, pp. 4177–4190 (1989).

J.N. Denis et al., "An Improved Synthesis of the Taxol Side Chain and of RP 56976," *J. Org. Chem.*, vol. 55, pp. 1957–1959 (1990).

I. Oshima et al., "Synthesis and Biological Activity of 3'–alkyl–and 3'–alkenyl–3'–dephenyldocetaxels," *Bioorganic & Medicinal Chemistry Letters*, vol. 4, No. 21, pp.–2631–2634 (1994).

D. Gou et al., "A Practical Chemoenzymatic Synthesis of the Taxol C–13 Side Chain N–Benzoyl–(2R, 3S)–3–phenylisoserine," *J. Org. Chem.*, vol. 58, pp. 1287–1289 (1993).

Françoise Guéritte–Volegelein et al., "Relationships Between the Structure of Taxol Analoques and Their Antimitotic" J. Med. Chem. 34, pp. 992–998 (1991).

Chemical Abstracts, vol. 110, No. 19, May 8, 1989, abstract No. 173488h.

BACCATIN DERIVATIVES AND PROCESSES FOR PREPARING THE SAME

BACKGROUND OF THE INVENTION

This invention relates to baccatin derivatives which are synthetic intermediates of taxol derivatives useful as an antitumor agent, and processes for preparing the same.

It has been known that taxol (chemical name: 4α,10β-diacetoxy-2α-benzoyloxy-5β,20-epoxy-1β,7β-dihydroxy-13α-[(2R,3S)-3-phenyl-3-benzoylamino-2-hydroxypropionyloxy]-tax-11-en-9-one) which is diterpenoid obtained from bark of Taxus brevifolia and N-debenzoyl-N-(t-butoxycarbonyl)-10-deacetyltaxol (chemical name: 4α-acetoxy-2α-benzoyloxy-5β,20-epoxy-1β,7β,10β-trihydroxy-13α-[(2R,3S)-3-phenyl-3-(t-butoxycarbonylamino)-2-hydroxypropionyloxy]-tax-11-en-9-one) which is a derivative thereof have excellent antitumor activities on ovary cancer and cancers of thymus and others ("Annual Reports in Medicinal Chemistry", Chapter 32, p. 305 (1993)).

Among taxane derivatives, a compound in which a side chain at 13-position of a taxane skeleton is hydroxy group has been known as a baccatin compound and named baccatin I–VII or the like depending on a substituent on the taxane skeleton ("Dictionary of Organic Compounds, the 4th edition (the 3rd supplement), p. 506 (1985)).

It has been variously attempted to prepare taxol and N-debenzoyl-N-(t-butoxycarbonyl)-10-deacetyltaxol by introducing a side chain into hydroxy group which is a substituent at 13-position of a baccatin compound. There have been known, for example, (A) a method of reacting a baccatin compound with N-benzoyl-3-phenylisoserine in which hydroxy group is protected, in the presence of a condensing agent ("Journal of American Chemical Society", Vol. 110, p. 5917 (1988)), (B) a method of reacting a baccatin compound with a 4-phenylazetidinone compound (Japanese Provisional Patent Publication No. 1782/1994), (C) a method of reacting a baccatin compound with an oxazolidine compound ("Tetrahedron Letters", Vol. 33, No. 36, p. 5185 (1992)) and (D) a method consisting of reaction of baccatin with cinnamoyl chloride and osmium oxidation of the resulting cynnamic ester in the presence of sodium t-butylchlorocarbamate (Japanese Provisional Patent Publications No. 30478/1988 and No. 30479/1988).

However, in the above method (A), the reaction time is long and also the yield is low even when N-benzoyl-3-phenylisoserine is used excessively; in the above methods (B) and (C), the preparation of the 4-phenylazetidinone compound and the oxazolidine compound are both complicated; and in the above method (D), the reaction doesn't proceed stereoselectively or regioselectively so that this method is not good for preparing taxol derivatives.

It has been also known that taxol has an excellent antitumor activity on various kinds of cancers as mentioned above, but water-solubility is as extremely low as 0.004 mg/ml or less ("Nature", Vol. 346, p. 464 (1993)), which is a clinical problem.

In order to improve the antitumor activity and water-solubility of taxol, modifications of various substituents have been carried out in the prior art (e.g., Japanese Provisional Patent Publications No. 30478/1988 and No. 30479/1988, "Tetrahedron Letters", Vol. 33, p. 5185 (1992) and "Tetrahedron", Vol. 45, p. 4177 (1989)). As an example of improving water-solubility by modifying hydroxy group in a side chain at 13-position and/or hydroxy group at 7-position of taxol with a hydrophilic group, there may be mentioned, for example, U.S. Pat. Nos. 4,960,790, 5,059,699 and 5,283,253, and Japanese Provisional Patent Publication No. 1782/1994. In U.S. Pat. No. 4,960,790, there has been described a taxol derivative obtained by modifying hydroxy group in a side chain at 13-position and/or hydroxy group at 7-position directly with a residue obtained from amino acid such as alanine, leucine and isoleucine. In U.S. Pat. No. 5,059,699, there has been described a taxol derivative obtained by modifying hydroxy group in a side chain at 13-position with a group such as —CO—(CH$_y$)$_n$—CO—NH—(CH$_2$)$_2$—SO$_3$—M (where y is 1 or 2, n is 1 to 3, M is hydrogen atom, an alkali metal or the like, e.g., sodium 4-(2-sulfonatoethyl)amino-1,4-dioxobutyl group). In Japanese Provisional Patent Publication No. 1782/1994, there has been described a taxol derivative obtained by esterifying hydroxy group in a side chain at 13-position, hydroxy group at 7-position and/or hydroxy group at 10-position with phosphoric acid or carbonic acid. Further, in U.S. Pat. No. 5,283,253, there has been described a taxol derivative obtained by substituting amino group in a side chain at 13-position by furancarbonyl group or thiophenecarbonyl group and modifying hydroxy group in a side chain at 13-position and/or hydroxy group at 7-position with a carboxyl group-substituted or carbamoyl group-substituted lower alkanoyl group.

However, heretofore, it has not been reported that a taxol derivative having high water-solubility, and stability and excellent antitumor activity is used clinically.

SUMMARY OF THE INVENTION

An object of the present invention is to provide a process for efficiently preparing baccatin derivatives, which are important synthetic intermediates for preparing taxol derivative, by efficiently introducing a side chain into hydroxy group at 13-position of a baccatin compound by the use of a starting compound synthesized in a simple and easy method, and to provide novel synthetic intermediates generated in the course of the above-mentioned preparation.

Another object of the present invention is to provide novel taxol derivatives each having an excellent antitumor activity and improved water-solubility. Still another object of the present invention is to provide processes for preparing such novel taxol derivatives.

According to the first embodiment of the present invention, a 13α-(3-amino-2-hydroxypropionyloxy) baccatin derivative represented by the formula (VI):

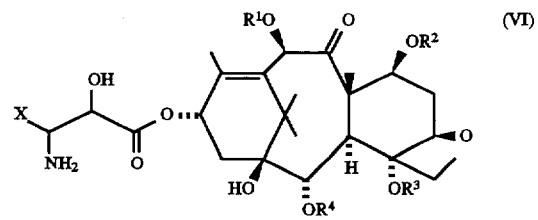

wherein R$^1$ represents a lower alkanoyl group or a protective group for hydroxy group; R$^2$ represents a protective group for hydroxy group; R$^3$ represents a lower alkanoyl group; R$^4$ represents a substituted or unsubstituted benzoyl group; and X represents a substituted or unsubstituted aryl group, a substituted or unsubstituted lower alkenyl group, or a substituted or unsubstituted lower alkynyl group, or a salt thereof can be prepared by condensing a baccatin compound represented by the formula (II):

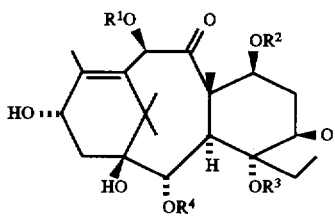

wherein $R^1$, $R^2$, $R^3$ and $R^4$ have the same meanings as described above, and an epoxypropionic acid compound represented by the formula (I):

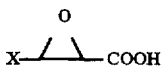

wherein X has the same meaning as described above, or a reactive derivative thereof to obtain a 13α-epoxypropionyloxybaccatin compound represented by the formula (III):

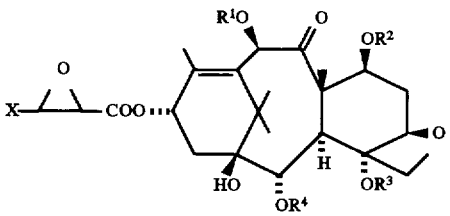

wherein $R^1$, $R^2$, $R^3$, $R^4$ and X have the same meanings as described above, introducing an azido group to the compound represented by the formula (III) to obtain a 13α-(3-azido-2-hydroxypropionyloxy)baccatin compound represented by the formula (V):

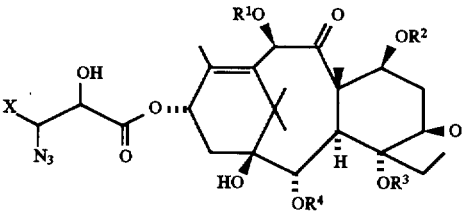

wherein $R^1$, $R^2$, $R^3$, $R^4$ and X have the same meanings as described above, reducing the compound represented by the formula (V) and, if necessary, converting the resulting compound into a salt.

In the second embodiment of the present invention, the 13α-(3-azido-2-hydroxypropionyloxy)baccatin derivative represented by the above formula (V) can be prepared by halogenating the compound represented by the above formula (III) to obtain a 13α-(3-halogeno-2-hydroxypropionyloxy)baccatin compound represented by the formula (IV):

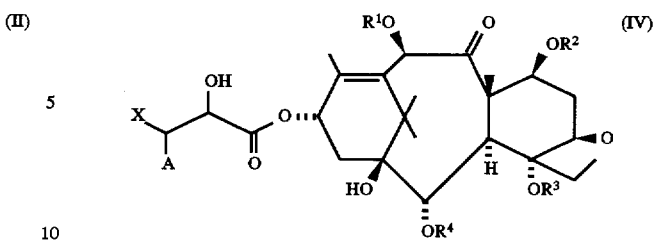

wherein A represents a halogen atom; and $R^1$, $R^2$, $R^3$, $R^4$ and X have the same meanings as described above, and introducing an azido group to the compound represented by the formula (IV).

According to the third embodiment of the present invention, there are provided a compound represented by the formula (X):

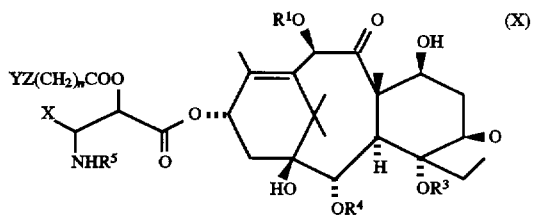

wherein $R^5$ represents a substituted or unsubstituted lower alkoxycarbonyl group (where said lower alkoxycarbonyl group may have a cycloalkyl portion), a substituted or unsubstituted lower alkanoyl group, a substituted or unsubstituted arylcarbonyl group or a substituted or unsubstituted aromatic heterocyclic group-substituted carbonyl group; Y represents a residue obtained by removing hydroxy group of one carboxyl group from an amino acid or dipeptide (where amino group and/or carboxyl group existing in said residue may be protected); Z represents a group represented by —O— or —NH—; and n represents an integer of 1 to 6; X, $R^3$ and $R^4$ have the same meaning as described above, or a pharmaceutically acceptable salt thereof.

DESCRIPTION OF THE PREFERRED EMBODIMENTS

In the following, the present invention is explained in detail.

In the first and second embodiments of the present invention, as the aryl group of X in the above formulae (I), (III), (IV), (V), (VI) or (X), there may be mentioned an aromatic hydrocarbon cyclic group (e.g., phenyl group and naphthyl group) or an aromatic heterocyclic group (e.g., furyl group, thienyl group and pyridyl group); and as the halogen atom of A in the formula (IV), there may be mentioned chlorine atom, bromine atom and iodine atom. Furthermore, as the protective group for hydroxy group used as $R^1$ and/or $R^2$ in formulae (II) to (VI) and (X), there may be mentioned a conventionally used protective group for hydroxy group, which can be removed easily according to a conventional method.

Specifically, the processes in the first and second embodiments of the present invention can be applied suitably when $R^1$ is a lower alkanoyl group (e.g., acetyl group, propionyl group, butyryl group and pentanoyl group), or a protective group for hydroxy group such as a trihalo-lower alkoxycarbonyl group (e.g., trichloroethoxycarbonyl group) and a tri-lower alkylsilyl group (e.g., trimethylsilyl group and triethylsilyl group); $R^2$ is a protective group such as a trihalo-lower alkoxycarbonyl group (e.g., trichloroethoxycarbonyl group), a tri-lower alkylsilyl group (e.g., trimethylsilyl group and triethylsilyl group); $R^3$ is a lower alkanoyl group (e.g., acetyl group, propionyl group, butyryl group and pentanoyl group); $R^4$ is unsubstituted benzoyl group or a substituted benzoyl group (e.g., a benzoyl group substituted by a lower alkyl group, a lower alkoxy group or a halogen atom); and X is unsubstituted phenyl group, a substituted phenyl group (e.g., a phenyl group substituted by a lower alkyl group, a lower alkoxy group or a halogen atom) or an unsubstituted lower alkenyl group (e.g., vinyl group). Said processes of the present invention can be applied particularly suitably when $R^1$ is acetyl group or trichloroethoxycarbonyl group, $R^2$ is trichloroethoxycarbonyl group, $R^3$ is acetyl group, $R^4$ is unsubstituted benzoyl group, X is unsubstituted phenyl group and A is bromine atom.

In the epoxypropionic acid compound (I) of the present invention, there exist four kinds of stereoisomers [a (2R,3S) type and a (2S,3R) type (trans isomer) and a (2R,3R) type and a (2S,3S) type (cis isomer)] based on asymmetric carbon atoms at 2-position and 3-position. Also in the 13α-epoxypropionyloxybaccatin compound (III), the 13α-(3-halogeno-2-hydroxypropionyloxy)baccatin compound (IV), the 13α-(3-azido-2-hydroxypropionyloxy)baccatin derivative (V) and a 13α-(3-amino-2-hydroxypropionyloxy) baccatin derivative (VI), there exist four kinds of stereoisomers [a (2R,3S) type, a (2S,3R) type, a (2R,3R) type or a (2S,3S) type isomer] based on two asymmetric carbon atoms existing in a side chain at 13-position.

The processes of the present invention are applicable to the cases using either of the isomers or a mixture thereof and all the reactions proceed regioselectively and stereoselectively.

When (2R,3S), (2S,3R), (2R,3R) and (2S,3S) type of epoxypropionic acid compound (I) is used in the first embodiment, (2R,3S), (2S,3R), (2R,3R) and (2S,3S) type of 13α-epoxypropionyloxybaccatin compound (III); (2R,3R), (2S,2S), (2R,3S) and (2S,3R) type of 13α-(3-azido-2-hydroxypropionyloxy)baccatin derivative (V); and (2R,3R), (2S,3S), (2R,3S) and (2S,3R) type of 13α-(3-amino-2-hydroxypropionyloxy)baccatin derivative (VI) are obtained, respectively.

The first embodiment of the present invention can be preferably carried out by the use of (2R,3R) or (2S,3S) type of epoxypropionic acid compound (I) to give (2R,3R) or (2S,3S) type of 13α-epoxypropionyloxybaccatin compound (III); (2R,3S) or (2S,3R) type of 13α-(3-azido-2-hydroxypropionyloxy)baccatin derivative (V); and (2R,3S) or (2S,3R) type of 13α-(3-amino-2-hydroxypropionyloxy) baccatin derivative (VI), respectively. In this embodiment, the process in which (2R,3R) type of epoxypropionic acid compound (I) is used to give (2R,3S) type of 13α-(3-amino-2-hydroxypropionyloxy)baccatin derivative (VI) is the most preferred.

On the other hand, when (2R,3S), (2S,3R), (2R,3R) and (2S,3S) type of epoxypropionic acid compound (I) is used in the second embodiment, (2R,3S), (2S,3R), (2R,3R) and (2S,3S) type of 13α-epoxypropionyloxybaccatin compound (III); (2S,3R), (2R,3S), (2S,3S) and (2R,3R) type of 13α-(3-halogeno-2-hydroxypropionyloxy)baccatin derivative (IV) (2R,3S), (2S,3R), (2R,3R) and (2S,3S) type of 13α-(3-azido-2-hydroxypropionyloxy)baccatin derivative (V); and (2R,3S), (2S,3R), (2R,3R) and (2S,3S) type of 13α-(3-amino-2-hydroxypropionyloxy)baccatin derivative (VI) are obtained, respectively.

The second embodiment of the present invention can be preferably carried out by the use of (2R,3S) or (2S,3R) type of epoxypropionic acid compound (I) to give (2R,3S) or (2S,3R) type of 13α-epoxypropionyloxybaccatin compound (III); (2S,3R) or (2R,3S) type of 13α-(3-halogeno-2-hydroxypropionyloxy)baccatin derivative (IV); (2R,3S) or (2S,3R) type of 13α-(3-azido-2-hydroxypropionyloxy) baccatin derivative (V); and (2R,3S) or (2S,3R) type of 13α-(3-amino-2-hydroxypropionyloxy)baccatin derivative (VI), respectively. In this embodiment, the process in which (2R,3S) type of epoxypropionic acid compound (I) is used to give (2R,3S) type of 13α-(3-amino-2-hydroxypropionyloxy)baccatin derivative (VI) is the most preferred.

The condensation of the baccatin compound (II) and the epoxypropionic acid compound (I) or a reactive derivative thereof can be carried out in a suitable solvent. As the solvent, there may be mentioned an aromatic solvent (e.g., benzene, toluene and xylene), and as the reactive derivative, there may be mentioned an acid halide (e.g., acid chloride, acid bromide and acid iodide), an active ester (e.g., p-nitrophenyl ester) and a mixed acid anhydride (e.g., a mixed acid anhydride with methanesulfonic acid, benzenesulfonic acid or toluenesulfonic acid). The condensation of the baccatin compound (II) and the epoxypropionic acid compound (I) can be carried out by using a condensing agent. As the condensing agent, there may be used N,N'-dicyclohexylcarbodiimide, N,N'-carbonyldiimidazole, a dilower alkyl azodicarboxylate (e.g., dimethyl azodicarboxylate) and a 1-methyl-2-halopyridinium iodide (e.g., 1-methyl-2-bromopyridinium iodide). The condensation is carried out preferably in the presence of an organic base. As the organic base, there may be used an aromatic tertiary amine (e.g., 4-(N,N-dimethylamino)pyridine and N,N-dimethylaniline). On the other hand, the condensation of the baccatin compound (II) and the reactive derivative of the epoxypropionic acid compound (I) can be carried out in the presence or absence of an acid acceptor. As the acid acceptor, there may be used an organic base (e.g., pyridine, triethylamine, N-methylpiperidine, N-methylmorpholine and N-ethyl-N,N-diisopropylamine). The present reaction can be carried out under cooling to under heating and is carried out particularly preferably at 18° C. to 80° C.

The subsequent azido group-introduction to the 13α-(epoxypropionyloxy)baccatin compound (III) can be carried out in a suitable solvent or without a solvent, and the azido group-introduction can be carried out by using a metal azide. As the metal azide, there may be suitably used either an alkali metal azide (e.g., lithium azide, sodium azide and potassium azide) or a tri-lower alkyltin azide (e.g., tri-n-butyltin azide). When the alkali metal azide is used, water, a mixture of water and a hydrophilic solvent (e.g., an alcohol type solvent such as methanol, ethanol, propanol and butanol, and a ketone type solvent such as acetone) or an aprotic polar organic solvent (e.g., dimethylsulfoxide, dimethylformamide and dimethylacetamide) may be used as a solvent. The reaction is carried out preferably in the presence of a base acceptor (e.g., a formate such as methyl formate and an ammonium salt such as ammonium chloride). On the other hand, when the tri-lower alkyltin azide is used, the reaction can be carried out without a solvent and may be carried out by adding an aprotic organic solvent (e.g., dimethylsulfoxide, dimethylformamide and dimethylacetamide), if necessary. The reaction can be accelerated by adding a Lewis acid (e.g., zinc bromide, zinc iodide, tin bromide and tin iodide). The present reaction can be carried out under cooling to under heating and is carried out particularly preferably at 20° C. to 60° C.

In the process of the present invention, the reaction of the 13α-(epoxypropionyloxy)baccatin compound (III) and the metal azide can be carried out regioselectively and stereoselectively. Trans opening of the 3-phenylepoxypropionyl group proceeds by the SN2 mechanism so that by using the (2R,3R) type, (2R,3S) type, (2S,3S) type and (2S,3R) type epoxypropionic acid compounds (I), the corresponding (2R, 3S) type, (2R,3R) type, (2S,3R) type and (2S,3S) type 13α-(3-azido-2-hydroxypropionyloxy)baccatin compounds (V) and 13α-(3-amino-2-hydroxypropionyloxy)baccatin derivatives (VI) can be obtained, respectively.

On the other hand, the halogenation of the 13α-epoxypropionyloxybaccatin compound (III) can be carried out in a solvent in the presence of a Lewis acid and a halogenating agent. As the Lewis acid, there may be mentioned a titanium halide (e.g., titanium tetrachloride, titanium tetrabromide and titanium tetraiodide), a tin halide (e.g., tin tetrachloride, tin tetrabromide and tin tetraiodide), a magnesium halide (e.g., magnesium chloride, magnesium bromide and magnesium iodide) and a di-lower alkylaluminum halide (e.g., diethylaluminum chloride). As the halogenating agent, there may be mentioned a di-lower alkylamine hydrohalide (e.g., diethylamine hydrochloride, diethylamine hydrobromide and diethylamine hydroiodide). When a titanium halide, tin halide or magnesium halide is used as a Lewis acid, said compound also acts as a halogenating agent so that it is not necessary to add a halogenating agent. As the solvent, there may be preferably used a mixed solvent of a halogenated hydrocarbon type solvent (e.g., dichloromethane and chloroform), an ether type solvent (e.g., tetrahydrofuran and diethyl ether) or an aromatic solvent (e.g., toluene and nitrobenzene) and an aprotic polar solvent (e.g., hexamethylphosphoric triamide (HMPA), dimethylformamide and dimethylimidazolidinone), and particularly preferred is a mixed solvent of a halogenated hydrocarbon type solvent and HMPA. Concerning of a ratio of the halogenated hydrocarbon type solvent and HMPA to be mixed, when the ratio of the halogenated hydrocarbon type solvent : HMPA is 1:0 to 0:1, in general, 20:1 to 5:1, the reaction proceeds suitably. The present reaction can be carried out under cooling to under heating and is carried out usually at −70° C. to 0° C.

The present halogenation proceeds regioselectively and stereoselectively, since opening of the epoxypropionyl group always proceeds by the SN2 mechanism so that using the 13α-(epoxypropionyloxy)baccatin compound (III) in which stereospecific configuration in a side chain at 13-position is (2R,3S) type, (2S,3R) type, (2R,3R) type or (2S,3S) type, the corresponding (2S,3R) type, (2R,3S) type, (2S,3S) type or (2R,3R) type 13α-(3-halogeno-2-hydroxypropionyloxy)baccatin compound (IV) can be obtained, respectively.

The azido group-introduction to the 13α-(3-halogeno-2-hydroxypropionyloxy)baccatin compound (IV) obtained can be carried out by protecting hydroxy group at 2-position in a side chain at 13-position, if desired, reacting the compound with a metal azide in a suitable solvent in the presence or absence of a metal clathration agent (a metal chelating agent) and removing a protective group when hydroxy group is protected.

When hydroxy group at 2-position in a side chain at 13-position is protected, a conventionally used protective group for hydroxy group which can be easily removed by a conventional method may be used as the protective group, and there may be mentioned, for example, a tri-lower alkylsilyl group (e.g., trimethylsilyl group and triethyl silyl group). As the metal clathration agent, there may be used crown ethers (e.g., 1,4,7,10-tetraoxacyclododecane, 1,4,7,10,13-pentaoxacyclopentadecane and 1,4,7,10,13,16-hexaoxacyclooctadodecane), and particularly preferred is 1,4,7,10,13-pentaoxacyclopentadecane. The metal azide, the solvent and the reaction conditions employed in the azido group-introduction to the 13α-(epoxypropionyloxy)baccatin compound (III) are also applicable to the azido-group introduction to the 13α-(3-halogeno-2-hydroxypropionyloxy) baccatin compound (IV).

The present azido group-introduction can be also carried out stereoselectively, and 3-position of the 3-halogeno-2-propionyloxy group is substituted by an azido group so that by using the 13α-(3-halogeno-2-hydroxypropionyloxy) baccatin compound (IV) in which stereospecific configuration in a side chain at 13-position is (2S,3R) type, (2R,3S) type, (2S,3S) type or (2R,3R) type, the corresponding (2R, 3S) type, (2S,3R) type, (2R,3R) type or (2S,3S) type 13α-(3-azido-2-hydroxypropionyloxy)baccatin derivative (V) can be obtained, respectively.

The 13α-(3-azido-2-hydroxypropionyloxy)baccatin derivative (V) thus obtained or a salt thereof can be converted into taxol derivative represented by the formula (IX):

(IX)

wherein $R^{11}$ represents a lower alkanoyl group or hydrogen atom; and $R^3$, $R^4$, $R^5$ and X have the same meanings as described above, (1) by subjecting the compound of the formula (V) or a salt thereof to reduction reaction to obtain a 13α-(3-amino-2-hydroxypropionyloxy)baccatin compound represented by the formula (VI):

(VI)

wherein $R^1$, $R^2$, $R^3$, $R^4$ and X have the same meanings as described above, reacting the compound obtained, with a carboxylic acid compound represented by the formula (VII):

$R^5OH$                                    (VII)

wherein $R^5$ represents a substituted or unsubstituted lower alkoxycarbonyl group (where said lower alkoxycarbonyl group may have a cycloalkyl portion), a substituted or unsubstituted lower alkanoyl group, a substituted or unsubstituted arylcarbonyl group or a substituted or unsubstituted aromatic heterocyclic group-substituted carbonyl group, a salt thereof or a reactive derivative thereof to obtain a 13α-(3-acylamino-2-hydroxypropionyloxy)baccatin compound represented by the formula (VIII):

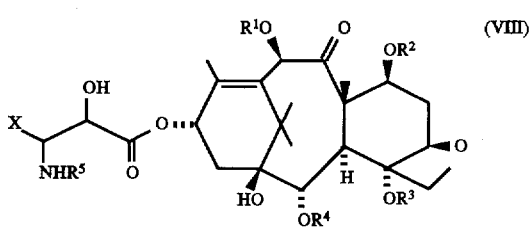

wherein $R^1, R^2, R^3, R^4, R^5$ and X have the same meanings as described above,
and removing a protective group from the compound obtained; or (2) subjecting the compound of the formula (V) or a salt thereof to reduction reaction in a suitable solvent in the presence of a reactive derivative of the carboxylic acid compound (VII) to obtain the 13α-(3-acylamino-2-hydroxypropionyloxy)baccatin compound (VIII) and removing a protective group from the compound obtained.

The taxol derivative represented by the formula (IX) is useful as an antitumor agent and a synthetic intermediate of an antitumor agent, and has been described as taxol, N-debenzoyl-N-(t-butoxycarbonyl)-10-deacetyltaxol or the like in Japanese Provisional Patent Publications No. 30479/1988 and No. 1782/1994, French Patent No. 2698363, PCT Provisional Patent Publication No. 92/09589 and "Bioorganic & Medicinal Chemistry Letters", Vol. 4, p. 2631 (1994).

The reduction of the 13α-(3-azido-2-hydroxypropionyloxy)baccatin derivative (V) can be carried out in a suitable solvent. As the solvent, there may be used an alcohol type solvent (e.g., methanol, ethanol, propanol and butanol), an ether type solvent (e.g., tetrahydrofuran and dioxane), acetic acid and a mixed solvent thereof. The reduction may be effected by catalytic reduction in the presence of a metal catalyst (e.g., palladium-carbon) or by using a reducing agent (e.g., triphenylphosphine). Especially, using triphenylphosphine, it is preferred to add a small amount of water.

The condensation of the 13α-(3-amino-2-hydroxypropionyloxy)baccatin compound (VI) or a salt thereof with the compound (VII) or a reactive derivative thereof can be carried out in a suitable solvent or without a solvent. Examples of the acid addition salt of the 13α-(3-amino-2-hydroxypropionyloxy)baccatin compound (VI) include formate thereof. As the solvent, there may be used an organic solvent (e.g., a halogenated hydrocarbon type solvent such as methylene chloride, an ether type solvent such as tetrahydrofuran and an aprotic organic solvent such as dimethylformamide). As the reactive derivative of the compound (VII), there may be mentioned the same acid halide and mixed acid anhydride as in the case of the epoxypropionic acid compound (I).

The condensation of the 13α-(3-amino-2-hydroxypropionyloxy)baccatin compound (VI) or a salt thereof with the compound (VII) can be carried out by employing the same condensing agent, the same organic base and the same reaction conditions as in the case of condensation of the baccatin compound (II) with the epoxypropionic acid compound (I). On the other hand, the condensation of the 13α-(3-amino-2-hydroxypropionyloxy) baccatin compound (VI) or a salt thereof with a reactive derivative of the compound (VII) can be carried out by employing the same condensing agent, the same organic base and the same reaction conditions as in the case of condensation of the baccatin compound (II) with a reactive derivative of the epoxypropionic acid compound (I).

The removal of the protective group from the 13α-(3-acylamino-2-hydroxypropionyloxy)baccatin compound (VIII) can be suitably carried out depending on the kind of the protective group according to a conventional method. When the protective group is a trihalo-lower alkoxycarbonyl group, the protective group can be easily removed by zinc-acetic acid-methanol treatment.

When the 13α-(3-azido-2-hydroxypropionyloxy)baccatin compound (V) is reduced in a suitable solvent in the presence of a reactive derivative of the compound (VII), an acid anhydride and a mixed acid anhydride with carbonic acid may be suitably used as the reactive derivative of the compound (VII). As the solvent, there may be suitably used a halogenated hydrocarbon type solvent (e.g., methylene chloride and chloroform) and an aromatic solvent (e.g., toluene and benzene). The reduction can be carried out by using a reducing agent (e.g., triphenylphosphine), and it is preferred to add a small amount of water.

The epoxypropionic acid compound (I) which is a starting compound of the present invention can be prepared by hydrolyzing a corresponding epoxypropionic acid ester with a base (e.g., an alkali metal hydroxide) according to a conventional method. Among the corresponding epoxypropionic acid esters, a trans form ester can be prepared by, for example, reacting a substituted or unsubstituted arylaldehyde, a substituted or unsubstituted lower alkenylaldehyde or a substituted or unsubstituted lower alkynylaldehyde with a haloacetic acid ester according to a conventional method of Darzens reaction and carrying out optical resolution, if necessary (Japanese Provisional Patent Publications No. 13775/1985, No. 13776/1985 and No. 15398/1991 and "Journal of Organic Chemistry", Vol. 58, p. 1287 (1993)). On the other hand, a cis form ester can be prepared by, for example, converting a substituted or unsubstituted trans form cinnamic acid ester into a dihydroxy compound by Sharpless asymmetric dihydroxylation to obtain a reactive monoester and then carrying out intramolecular cyclization by base treatment ("Journal of Organic Chemistry", Vol. 51, p. 46 (1986)) or subjecting a substituted or unsubstituted arylaldehyde, a substituted or unsubstituted lower alkenylaldehyde or a substituted or unsubstituted lower alkynylaldehyde and, if necessary, an optically active N-(2-halogenopropionyl)-2-oxazolidinone derivative to aldol condensation according to a conventional method, subjecting the obtained compound to dehydrohalegenation to form an oxirane ring and then removing a 2-oxazolidinone ring by hydrolysis, according to the method described in PCT Provisional Patent Publication No. 92/09589.

In the present invention, a taxol derivative represented by the formula (X):

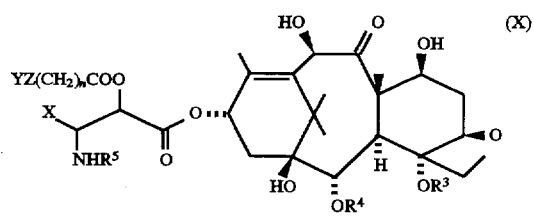

wherein $R^3, R^4, R^5$, X, Y, Z and n have the same meanings as described above, can be prepared by reacting a compound represented by the formula (VI-a):

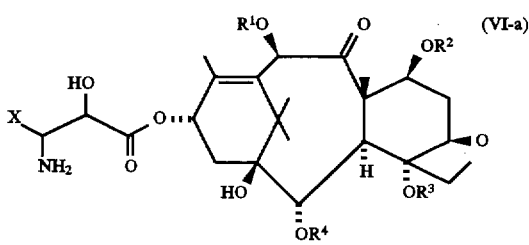

(VI-a)

wherein R' represents a protective group for hydroxy group, $R^2$, $R^3$ and $R^4$ have the same meaning as described above or a salt thereof with the compound (VII), a salt thereof or a reactive derivative thereof to obtain a compound represented by the formula (VIII-a):

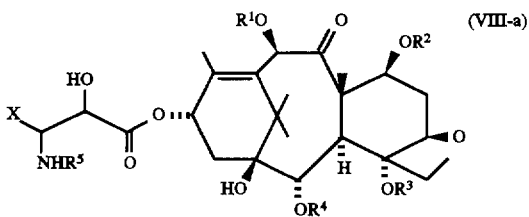

(VIII-a)

wherein R', $R^2$, $R^3$, $R^4$, $R^5$ and X have the same meaning as described above, and (1-a) reacting the obtained compound (VIII-a) with a compound represented by the formula (XI-a):

Y—Z(CH$_2$)$_n$COOH        (XI-a)

wherein Y' represents a residue obtained by removing hydroxy group of one carboxyl group from an amino acid or dipeptide (where amino group in said residue is protected, and carboxyl group existing in said residue may be protected), Z and n have the same meanings as described above, a salt thereof or a reactive derivative thereof and removing protective groups for hydroxy group from the resulting compound, or (1-b) removing protective groups for hydroxy group from the obtained compound (VIII-a) and the reacting the resulting compound with the compound (XI-a), a salt thereof or a reactive derivative thereof, (2) and, if required, further removing protective group(s) for amino group in Y' from the obtained compound.

As the salt of the compound (VI-a), there may be mentioned, for example, an organic acid salt such as formate, acetate, methanesulfonate and p-toluenesulfonate and an inorganic acid addition salt such as hydrochloride and hydrobromide.

As the salts of the compound (VII) and the compound (XI-a), there may be mentioned, for example, an alkali metal salt and an alkaline earth metal salt.

As the reactive derivative of the compound (VII) and the compound (XI-a), there may be mentioned an acid halide, an active ester and a mixed acid anhydride.

As the protective groups for hydroxy group, there may be mentioned, for example, 2,2,2-trichloroethoxycarbonyl group.

The reaction of the compound (VI-a) or a salt thereof with the compound (VII) or a salt thereof can be carried out in the presence or absence of a dehydrating agent in a suitable solvent or without a solvent. As the dehydrating agent, there may be suitably used dicyclohexylcarbodiimide, carbonyldiimidazole, 1-methyl-2-bromopyridinium iodide and benzotriazol-1-yloxytris(dimethylamino)phosphonium hexafluorophosphate. As the solvent, there may be suitably used dichloromethane, dimethyl ether, dimethylformamide, dioxane, tetrahydrofuran and toluene. The present reaction proceeds suitably at –20° to 100° C., particularly 0° to 30° C.

The reaction of the compound (VI-a) or a salt thereof with a reactive derivative of the compound (VII) can be carried out in the presence or absence of an acid acceptor in a suitable solvent or without a solvent. As the acid acceptor, there may be suitably used an alkali metal hydride, an alkali metal carbonate, an alkali metal hydrogen carbonate and an organic base (e.g., triethylamine, diisopropylethylamine, pyridine, 4-(N,N-dimethylamino)pyridine and 1,8-diazabicyclo[5.4.0]undec-7-ene). As the solvent, there may be suitably used dichloromethane, dimethyl ether, dimethylformamide, dioxane, tetrahydrofuran and toluene. The present reaction proceeds suitably at –20° to 80° C., particularly 0° to 30° C.

In step (1-a), the reaction of the compound (VIII-a) with the compound (XI-a) or a salt thereof and the reaction of the compound (VIII-a) with a reactive derivative of the compound (XI-a) can be carried out in the same manner as in the reaction of the compound (VI-a) or a salt thereof with the compound (VII) or a salt thereof and the reaction of the compound (VI-a) or a salt thereof with a reactive derivative of the compound (VII), respectively.

The subsequent removal of protective groups for hydroxy group from the resulting compound can be carried out by a conventional method. For example, when said protective group are 2,2,2-trichloroethoxycarbonyl group, zinc-acetic acid may be used for removing them.

In step (1-b), the reaction of removing protective groups for hydroxy group from the compound (VIII-a) can be carried out in the same manner as in the removal of protective groups in step (1-a).

The subsequent reaction of the resulting compound with the compound (XI-a) or a salt thereof and the reaction of the resulting compound with a reactive derivative of the compound (XI-a) can be carried out in the same manner as in the reaction of the compound (VI-a) or a salt thereof with the compound (VII) or a salt thereof and the reaction of the compound (VI-a) or a salt thereof with a reactive derivative of the compound (VII), respectively.

In step (2), the subsequent removal of protective groups for amino group in Y' from the compound obtained in step (1-a) or (1-b) can be carried out by a conventional method. For example, when said protective groups are benzyloxycarbonyl group, palladium-carbon in suitable solvent (for example, tetrahydrofuran) may be used for removing them.

The starting compound (VI) can be prepared by the method in the present invention described above. The compound represented by the formula (VI) is also described in PCT Provisional Patent Publication No. 92/09589 and can be prepared by the method described in the above publication. That is, the compound (VI) can be prepared by condensing a compound represented by the formula (XII):

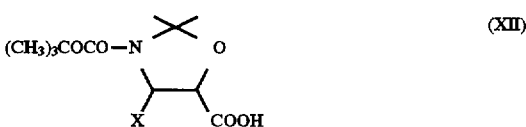

(XII)

wherein X has the same meaning as described above, and the compound (II), and then subjecting the resulting condensate to steps of cleaving an oxazolidine ring and removing tert-butoxycarbonyl group.

The compound (XII) can be prepared according to the method described in PCT Provisional Patent Publication No.

92/09589 or "Tetrahedron Letters", Vol. 33, p. 5185 (1992), for example, as shown in the following reaction scheme,

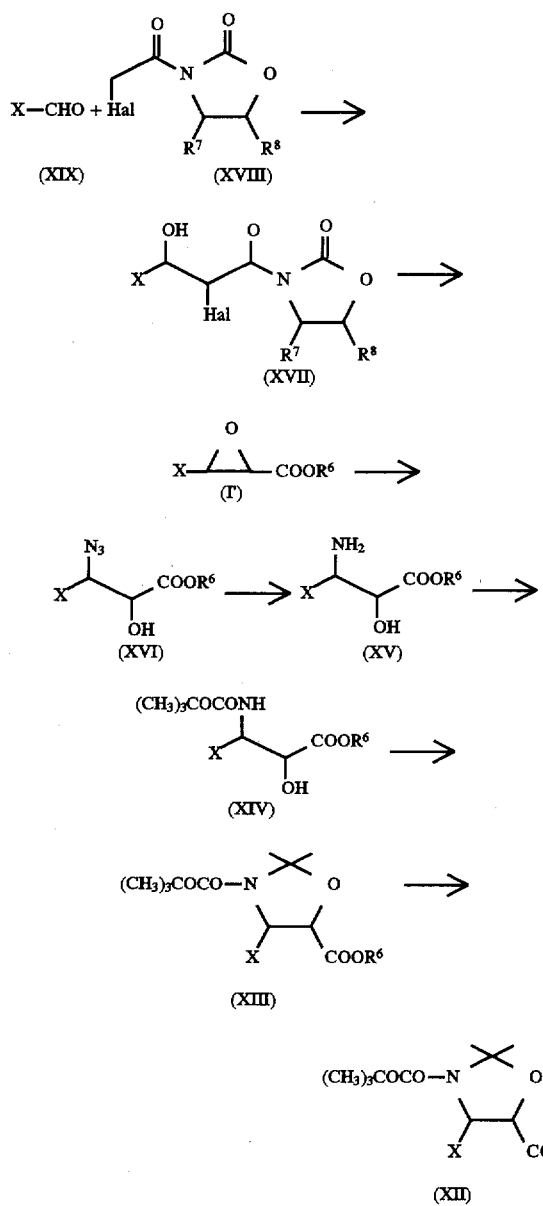

wherein Hal represents a halogen atom; $R^6$ represents an ester residue; $R^7$ and $R^8$ may be the same or different and each represent a lower alkyl group or phenyl group; and X has the same meaning as described above.

The compound (T) described in the above reaction scheme can be prepared by the method described in "Journal of Organic Chemistry", Vol. 55, p. 1957 (1990) and can be also synthesized according to the following reaction scheme.

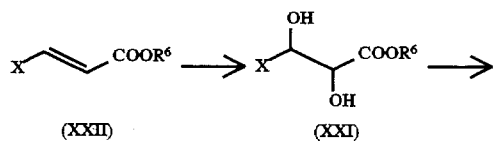

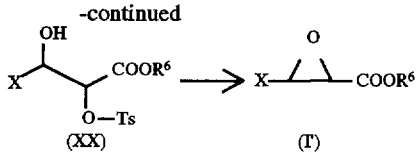

wherein Ts represents p-toluenesulfonyl group, and $R^6$ and X have the same meanings as described above.

Thus, for example, a compound (XII) in which X is 2,4-difluorophenyl group can be prepared by dihydroxylating methyl (2',4'-difluoro)cinnamate, eliminating hydroxy group at 2-position to prepare methyl 3-(2,4-difluorophenyl)-2-oxiranecarboxylate, subjecting the compound to azido group-introduction using a metal azide, subjecting the resulting compound to catalytic reduction, protecting amino group by tert-butoxycarbonyl group to obtain methyl 3-tert-butoxycarbonylamino-2-hydroxy-3-(2,4-difluorophenyl) propionate, protecting tert-butoxycarbonylamino group and hydroxy group of said compound by acetonide and then carrying out hydrolysis.

The compound (XIII) is described in Japanese Provisional Patent Publication No. 305077/1989 or No. 30479/1988 and can be prepared by protecting hydroxy group at 7-position and/or hydroxy group at 10-position of 10-deacetylbaccatin III, as desired.

The compound (XI-a) can be prepared by reacting a compound represented by the formula (XXIII):

Y'—OH        (XXIII)

wherein Y' represents the same meaning as described above, a salt thereof or a reactive derivative thereof with a compound represented by the formula (XXIV):

HZ(CH$_2$)$_n$COOR$^9$        (XXIV)

wherein $R^9$ represents hydrogen atom or an ester residue; and Z and n have the same meanings as described above, and removing the ester residue, if necessary.

In the desired compound (X), when X is a substituted aryl group, there may be mentioned a halogen atom, a lower alkyl group and a lower alkoxy group as the substituent on the aryl group.

As a substituent on the lower alkoxycarbonyl group, lower alkanoyl group, arylcarbonyl group or aromatic heterocyclic group-substituted carbonyl group of $R^5$, there may be mentioned a halogen atom and a lower alkoxy group. As an aromatic heterocyclic group portion of the aromatic heterocyclic group-substituted carbonyl group, there may be mentioned an aromatic heteromonocyclic group having sulfur atom, oxygen atom or nitrogen atom as a hereto atom, for example, a 5- or 6-membered aromatic heterocyclic group such as thienyl group, furyl group, pyridyl group, pirazinyl group and pyrimidinyl group. As the lower alkoxycarbonyl group having a cycloalkyl portion, there may be mentioned, for example, cyclopropylmethoxycarbonyl group, cyclobutylmethoxycarbonyl group and (2,2-dimethyl)cyclopropylmethoxycarbonyl group. Further, as an example of the lower alkoxycarbonyl group having a substituent and also having a cycloalkyl portion, there may be mentioned (2,2-difluoro-3,3-dimethyl)cyclopropylmethoxycarbonyl group.

In the desired compound (X), the amino acid of Y includes amino acids from natural or unnatural source and is a compound having each one of at least amino group and carboxyl group in one molecule. There may be mentioned an amino acid from natural source or an antipode thereof, a D- or L-amino acid obtained by synthesis, or a racemic mixture of these amino acids.

There may be specifically mentioned an α-amino acid or β-amino acid having amino group on carbon atom at α-position or β-position of carboxyl group or other amino acids. As the α-amino acid or β-amino acid, there may be mentioned a natural amino acid or a non-natural amino acid, and a neutral amino acid, an acidic amino acid or a basic amino acid thereof may be suitably used. As the basic amino acid, there may be mentioned an amino acid having plural amino groups such as asparagine, ornithine and lysine; as the acidic amino acid, there may be mentioned an amino acid having plural carboxyl groups such as glutamic acid and aspartic acid; and as the neutral amino acid, there may be mentioned an amino acid having the same number of amino groups and carboxyl groups such as alanine, isoleucine and leucine. Further, in the present invention, as a specific example of the amino acid which can be used suitably, there may be mentioned glycine, alanine, isoleucine, leucine, valine, glutamic acid, methionine, phenylalanine, proline, β-alanine, arginine, ornithine, serine, threonine, asparagine, aspartic acid, glutamine, cystine, cysteine, tyrosine, histidine, tryptophan, lysine, sarcosine, creatine, homocysteine, norleucine, isoserine, homoserine, norvaline, ε-aminocaproic acid, thioproline, α-aminoisobutanoic acid, piperidylcarboxylic acid, α,γ-diaminobutyric acid, β-aminobutyric acid and γ-aminobutyric acid.

Further, as the dipeptide of Y, there may be mentioned a dipeptide comprising the above amino acid, specifically a dipeptide comprising the above natural amino acid or an antipode thereof such as glycylglycine, valylglycine, methionylglycine, prolylglycine, glycylproline, glycylphenylalanine, phenylalanylglycine, glycylvaline, alanylproline, valylproline and phenylalanylvaline.

When the amino group and/or carbonyl group in Y is/are protected, a conventional protective group may be used as a protective group. As the protective group for the amino group, there may be mentioned, for example, benzyloxycarbonyl group, tert-butoxycarbonyl group and aminoacetyl group; and as the protective group for the carboxyl group, there may be mentioned methyl group, ethyl group, methoxyethyl, methoxyethoxyethyl and amino group.

As a preferred example of the desired compound (X) of the present invention, there may be mentioned a compound in which Y is an α- or β-amino acid or a residue obtained by removing hydroxy group from one carboxyl group of a dipeptide comprising the above acid (where amino group and/or carboxyl group existing in said residue may be protected).

As a more preferred example of the desired compound (X), there may be mentioned a compound in which X is a benzene ring which may be substituted by 1 or 2 groups selected from the group consisting of a halogen atom, a lower alkyl group and a lower alkoxy group; $R^5$ is a lower alkoxycarbonyl group which may be substituted by 1 to 3 groups selected from the group consisting of a halogen atom and a lower alkoxy group (where said lower alkoxycarbonyl group may have a 3- to 5-membered cycloalkyl portion), a lower alkanoyl group which may be substituted by a halogen atom, a benzoyl group which may be substituted by 1 or 2 lower alkoxy groups, furancarboxyl group or thiophenecarbonyl group; and Y is a natural amino acid or an antipode thereof, or a residue obtained by removing hydroxy group from one carboxyl group of a dipeptide comprising a natural amino acid or an antipode thereof (where amino group existing in said residue may be protected by benzyloxycarbonyl group, and carboxyl group existing in said residue may be protected by a lower alkyl group which may be substituted by a lower alkoxy group, or amino group).

As a further preferred compound of the desired compound (X) of the present invention, there may be mentioned a compound in which Y is asparagine, aspartic acid, proline, glycine, alanine or β-alanine, or a residue obtained by removing hydroxy group from one carboxyl group of a dipeptide comprising the above amino acid (where amino group existing in said residue may be protected by benzyloxycarbonyl group, and carboxyl group existing in said residue may be protected by a lower alkyl group which may be substituted by a lower alkoxy group, or amino group). Particularly preferred is a compound in which Y is a residue obtained by removing hydroxy group from one carboxyl group of aspartic acid, proline, glycine, alanine, β-alanine or glycylglycine (where amino group existing in said residue may be protected by benzyloxycarbonyl group, and carboxyl group existing in said residue may be protected by a lower alkyl group which may be substituted by a lower alkoxy group, or amino group).

In the present invention, as a compound exhibiting an excellent pharmaceutical effect, there may be mentioned a compound represented by the formula (X) in which $R^3$ is acetyl group; $R^4$ is benzoyl group; $R^5$ is a lower alkoxycarbonyl group; and Y is alanyl group, prolyl group, glycylglycyl group or β-aspartyl group (where carboxyl group may be protected by a lower alkyl group which may be substituted by a lower alkoxy group).

In the desired compound (X) of the present invention, various stereoisomers and optical isomers can exist based on two asymmetric carbon atoms of a substituted 3-phenylpropionyloxy group bonded to 13-position of a taxane skeleton and an asymmetric carbon atom existing in a substituent thereof. All of these stereoisomers, optical isomers and mixtures thereof are included in the present invention.

The desired compound (X) of the present invention can be used for medicinal purposes either in a free form or in the form of a pharmaceutically acceptable salt thereof. As the pharmaceutically acceptable salt, there may be mentioned an acid addition salt with an inorganic acid or an organic acid, or a salt with an inorganic base or an organic base, for example, salts such as hydrochloride, sulfate, hydrobromide, methanesulfonate, acetate, fumarate, maleate, oxalate, an alkali metal (e.g., sodium and potassium) salt, an alkaline earth metal (e.g., magnesium and calcium) sale and a triethylamine salt.

The desired compound (X) of the present invention or a pharmaceutically acceptable salt thereof can be administered either orally or parenterally, and it can be used as a suitable medical preparation such as a tablet, a granule, a capsule, a powder, an injection and an inhalation.

The dose of the desired compound (X) of the present invention or a pharmaceutically acceptable salt thereof varies depending on an administration method and age, body weight and state of a patient, but, in general, the dose per day is preferably about 0.2 to 20 mg/kg, particularly preferably 1.0 to 5 mg/kg.

In the present invention, the lower alkyl group, the lower alkenyl group, the lower alkynyl group, the lower alkoxy group and the lower alkanoyl group mean an alkyl group having 1 to 5 carbon atoms, an alkenyl group having 1 to 5 carbon atoms, an alkynyl group having 1 to 5 carbon atoms, an alkoxy group having 1 to 5 carbon atoms and an alkanoyl group having 2 to 6 carbon atoms, respectively. As the lower alkanoyl group or the lower alkoxycarbonyl group, there may be mentioned, for example, those having 2 to 7 carbon atoms, particularly 2 to 5 carbon atoms such as acetyl group, propionyl group, butyryl group, valeryl group, pivaloyl group, methoxycarbonyl group, ethoxycarbonyl group, propoxycarbonyl group and butoxycarbonyl group. As the halogen atom, there may be mentioned chlorine, bromine, fluorine and iodine.

Further, in the present specification, the taxane or taxane skeleton represents a diterpene skeleton represented by the following formula.

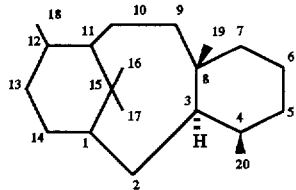

EXAMPLES

The present invention is described in detail by referring to Examples and Reference examples.

Example 1

(1) Under ice cooling, a solution of 0.504 g of lithium hydroxide monohydrate dissolved in 25 ml of water was added dropwise to a solution of 1.78 g of methyl (2R,3R)-3-phenyl-2,3-epoxypropionate dissolved in 50 ml of methanol. The mixture was allowed to room temperature and stirred for 1 hour at the same temperature. Methanol was removed from the reaction mixture, and the pH of the residue was adjusted to 3 to 4 by adding a 5% aqueous citric acid solution thereto under ice cooling, and then extracted with chloroform. The chloroform layer was washed with brine and then dried over magnesium sulfate. The solvent was removed under reduced pressure, and hexane was added to the residue. Crystals precipitated were collected by filtration, washed with hexane and then dried to obtain 1.32 g of (2R,3R)-3-phenyl-2,3-epoxypropionic acid. Yield: 80% m.p.: 81.5° to 83.0° C.

IR (nujol) $v_{max}$ (cm$^{-1}$): 3140, 1750, 1720, 1460, 1200

FAB-MS (m/z): 165 (MH$^+$)

$^1$H-NMR (CDCl$_3$) δ: 3.83 (1H, d, J=4.7 Hz), 4.31 (1H, d, J=4.7 Hz), 7.1 to 7.4 (5H, m), 8.2 (1H, broad s)

(2) In 250 ml of toluene were dissolved 1.376 g of (2R,3R)-3-phenyl-2,3-epoxypropionic acid and 4.998 g of 4α-acetoxy-2α-benzoyloxy-5β,20-epoxy-1β,13α-dihydroxy-7β,10β-di(2,2,2-trichloroethoxycarbonyloxy)-tax-11-en-9-one. To the solution were added 1.844 g of N,N'-dicyclohexylcarbodiimide and 0.34 g of 4-(N,N-dimethylamino)pyridine, and the mixture was stirred at 80° C. for 90 minutes. After the reaction mixture was cooled to room temperature, insolubles were removed by filtration, and the solvent was removed from the filtrate under reduced pressure. The residue was purified by silica gel flash column chromatography (solvent: ethyl acetate-hexane (2:5)) to obtain 5.734 g of 4α-acetoxy-2α-benzoyloxy-5β,20-epoxy-1β-hydroxy-7β,10β-di(2,2,2-trichloroethoxycarbonyloxy)-13α-[(2R,3R)-3-phenyl-2,3-epoxypropionyloxy]-tax-11-en-9-one. Yield: 99%

$[α]_D^{20}$=−15.77° (c=0.9, chloroform)

IR (nujol) $v_{max}$ (cm$^{-1}$): 3500, 1760, 1730, 1460, 1380, 1250, 1060

FAB-MS (m/z); 1039 (MH$^+$)

$^1$H-NMR (CDCl$_3$) δ: 1.14 (6H, s), 1.58 (1H, s), 1.83 (6H, s), 1.95 to 2.1 (3H, m), 2.39 (3H, s), 2.63 (1H, m), 3.87 (1H, d, J=7 Hz), 3.97 (1H, d, J=4.5 Hz), 4.14 (1H, d, J=9 Hz), 4.30 (1H, d, J=9 Hz), 4.33 (1H, d, J=4.5 Hz), 4.60 (1H, d, J=11.8 Hz), 4.76 (2H, s), 4.92 (1H, d, J=11.8 Hz), 4.97 (1H, m), 5.55 (1H, dd, J=7, 11 Hz), 5.63 (1H, d, J=7 Hz), 6.03 (1H, m), 6.19 (1H, s), 7.3 to 7.5 (7H, m), 7.64 (1H, m), 8.00 (2H, m)

(3-1) In a mixed solvent of 0.3 ml of water and 2.7 ml of methanol was dissolved 105 mg of 4α-acetoxy-2α-benzoyloxy-5β,20-epoxy-1β-hydroxy-7β,10β-di(2,2,2-trichloroethoxycarbonyloxy)-13α-[(2R,3R)-3-phenyl-2,3-epoxypropionyloxy]-tax-11-en-9-one. To the solution were added 0.3 ml of methyl formate and 195 mg of sodium azide, and the mixture was stirred at 50° C. for 40 hours. The reaction mixture was cooled to room temperature and then poured into cold water, and the aqueous mixture was extracted with ethyl acetate. The extract was washed with a 5% aqueous citric acid solution and then brine and dried over sodium sulfate, and the solvent was removed under reduced pressure. The residue was purified by silica gel thin layer chromatography (solvent: ethyl acetate-chloroform (1:20)) to obtain 92 mg of 4α-acetoxy-2α-benzoyloxy-5β,20-epoxy-1β-hydroxy-7β,10β-di(2,2,2-trichloroethoxycarbonyloxy)-13α-[(2R,3S)-3-phenyl-3-azido-2-hydroxypropionyloxy]-tax-11-en-9-one.

Yield: 85%

$[α]_D^{22}$=−16.43° (c=1, chloroform)

IR (nujol) $v_{max}$ (cm$^{-1}$): 3480, 2110, 1760, 1730, 1460, 1380, 1250

FAB-MS (m/z): 1082 (MH$^+$)

$^1$H-NMR (CDCl$_3$) δ: 1.20 (3H, s), 1.27 (3H, s), 1.70 (1H, s), 1.86 (3H, s), 2.09 (3H, d, J=1 Hz), 2.0 to 2.2 (3H, m), 2.30 (3H, s), 2.63 (1H, m), 3.12 (1H, d, J=8 Hz), 3.90 (1H, d, J=7 Hz), 4.16 (1H, d, J=8 Hz), 4.32 (1H, d, J=8 Hz), 4.44 (1H, dd, J=4, 8 Hz), 4.61 (1H, d, J=12 Hz), 4.76 (1H, d, J=12 Hz), 4.82 (1H, d, J=12 Hz), 4.92 (1H, d, J=12 Hz), 4.95 (1H, m), 5.01 (1H, d, J=4 Hz), 5.56 (1H, dd, J=7, 11 Hz), 5.68 (1H, d, J=7 Hz), 6.22 (1H, m), 6.27 (1H, s), 7.46 (5H, m), 7.51 (2H, m), 7.64 (1H, m), 8.06 (2H, m)

(3-2) In 1 ml of tri-n-butyltin azide was dissolved 104 mg of 4α-acetoxy-2α-benzoyloxy-5β,20-epoxy-1β-hydroxy-7β,10β-di(2,2,2-trichloroethoxycarbonyloxy)-13α-[(2R,3R)-3-phenyl-2,3-epoxypropionyloxy]-tax-11-en-9-one at 50° C. 6 mg of zinc iodide was added to the solution, and the mixture was stirred at 50° C. for 5 days. The reaction mixture was returned to room temperature, purified by silica gel column chromatography (solvent: chloroform) followed by thin layer chromatography (solvent: ethyl acetate-chloroform (1:20)) to obtain 73 mg of 4α-acetoxy-2α-benzoyloxy-5β,20-epoxy-1β-hydroxy-7β,10β-di(2,2,2-trichloroethoxycarbonyloxy)-13α-[(2R,3S)-3-phenyl-3-azido-2-hydroxypropionyloxy]-tax-11-en-9-one. Yield: 67%

(4-1) In 4 ml of methanol was dissolved 92 mg of 4α-acetoxy-2α-benzoyloxy-5β,20-epoxy-1β-hydroxy-7β,10β-di(2,2,2-trichloroethoxycarbonyloxy)-13α-[(2R,3S)-3-phenyl-3-azido-2-hydroxypropionyloxy]-tax-11-en-9-one, and 47 mg of 10% palladium-carbon was added to the solution. The mixture was stirred under the atmospheric pressure of hydrogen at room temperature for 2 hours. The catalyst was removed from the reaction mixture by filtration, and the filtrate was concentrated under reduced pressure to obtain 90 mg of crude 4α-acetoxy-2α-benzoyloxy-5β,20-epoxy-1β-hydroxy-7β,10β-di(2,2,2- trichloroethoxycarbonyloxy)-13α-[(2R,3S)-3-phenyl-3-amino-2-hydroxypropionyloxy]-tax-11-en-9-one. The compound obtained was dissolved in 4 ml of tetrahydrofuran, and 39.7 mg of di-t-butyldicarbonate and 25.5 mg of potassium hydrogen carbonate were added to the solution. The mixture was stirred at room temperature for 19 hours. After diluted with ethyl acetate, the reaction mixture was washed with water and then brine. The organic layer was dried and concentrated under reduced pressure. The residue was purified by silica gel thin layer chromatography (solvent: ethyl acetate-hexane (2:3)) to obtain 69 mg of 4α-acetoxy-2α-benzoyloxy-5β,20-epoxy-1β-hydroxy-7β,10β-di(2,2,2-trichloroethoxycarbonyloxy)-13α-[(2R,3S)-3-phenyl-3-(t-butoxycarbonylamino)-2-hydroxypropionyloxy]-tax-11-en-9-one. Yield: 70%

$[\alpha]_D^{20}$=−39.0° (c=1, chloroform)

IR (nujol) $v_{max}$ (cm$^{-1}$): 3440, 1760, 1720

FAB-MS (m/z): 1156 (MH$^+$)

$^1$H-NMR (CDCl$_3$) δ: 1.20 (3H, s), 1.28 (3H, s), 1.35 (9H, s), 1.71 (1H, s), 1.86 (3H, s), 1.96 (3H, s), 2.01 to 2.12 (1H, m), 2.33 (2H, m), 2.39 (3H, s), 2.56 to 2.69 (1H, m), 3.33 (1H, d, J=5.4 Hz), 3.91 (1H, d, J=6.9 Hz), 4.18 (1H, d, J=8 Hz), 4.34 (1H, d, J=8 Hz), 4.60 (1H, d, J=12 Hz), 4.62 to 4.67 (1H, m), 4.78 (2H, m), 4.91 (1H, d, J=12 Hz), 4.93 to 4.98 (1H, m), 5.22 to 5.39 (1H, m), 5.38 (1H, d, J=9.4 Hz), 5.55 (1H, dd, J=7, 11 Hz), 5.70 (1H, d, J=6.9 Hz), 6.17 to 6.25 (1H, m), 6.25 (1H, s), 7.29 to 7.45 (5H, m), 7.46 to 7.54 (2H, m), 7.59 to 7.66 (1H, m), 8.08 to 8.13 (2H, m)

(4-2) In a mixed solvent of 5 ml of tetrahydrofuran and 0.2 ml of water was dissolved 92 mg of 4β-acetoxy-2α-benzoyloxy-5β,20-epoxy-1β-hydroxy-7β,10β-di(2,2,2-trichloroethoxycarbonyloxy)-13α-[(2R,3S)-3-phenyl-3-azido-2-hydroxypropionyloxy]-tax-11-en-9-one, and 25 mg of triphenylphosphine was added to the solution. The mixture was stirred at room temperature for 18 hours to obtain a reaction mixture containing 4α-acetoxy-2α-benzoyloxy-5β,20-epoxy-1β-hydroxy-7β,10β-di(2,2,2-trichloroethoxycarbonyloxy)-13α-[(2R,3S)-3-phenyl-3-amino-2-hydroxypropionyloxy]-tax-11-en-9-one. To this reaction mixture were added 39.7 mg of di-t-butyldicarbonate and 25.5 mg of potassium hydrogen carbonate, and the mixture was stirred at room temperature for 19 hours. The solvent was removed from the reaction mixture under reduced pressure, and the residue was purified by silica gel thin layer chromatography (solvent: ethyl acetate-hexane (2:3)) to obtain 75 mg of 4α-acetoxy-2α-benzoyloxy-5β,20-epoxy-1β-hydroxy-7β,10β-di(2,2,2-trichloroethoxycarbonyloxy)-13α-[(2R,3S)-3-phenyl-3-(t-butoxycarbonylamino)-2-hydroxypropionyloxy]-tax-11-en-9-one. Yield: 76%

(4-3) In 2 ml of methylene chloride was dissolved 57.3 mg of 4α-acetoxy-2α-benzoyloxy-5β,20-epoxy-1β-hydroxy-7β,10β-di(2,2,2-trichloroethoxycarbonyloxy)-13α-[(2R,3S)-3-phenyl-3-azido-2-hydroxypropionyloxy]-tax-11-en-9-one, and 36.3 mg of di-t-butyldicarbonate, 26 mg of potassium hydrogen carbonate, 28.5 mg of triphenylphosphine and 0.05 ml of water were added to the solution. The mixture was stirred at room temperature for 20 hours. The solvent was removed from the reaction mixture, and the residue was purified by silica gel thin layer chromatography (solvent: ethyl acetate-hexane (2:3)) to obtain 46 mg of 4α-acetoxy-2α-benzoyloxy-5β,20-epoxy-1β-hydroxy-7β,10β-di(2,2,2-trichloroethoxycarbonyloxy)-13α-[(2R,3S)-3-phenyl-3-(t-butoxycarbonylamino)-2-hydroxypropionyloxy]-tax-11-en-9-one. Yield: 75%

(5) In a mixed solution of 1.2 ml of acetic acid and 10.8 ml of methanol was dissolved 273 mg of 4α-acetoxy-2α-benzoyloxy-5β,20-epoxy-1β-hydroxy-7β,10β-di(2,2,2-trichloroethoxycarbonyloxy)-13α-[(2R,3S)-3-phenyl-3-(t-butoxycarbonylamino)-2-hydroxypropionyloxy]-tax-11-en-9-one, and 544 mg of zinc powder was added to the solution. The mixture was stirred at 60° C. for 2 hours. Insolubles were removed from the reaction mixture by filtration, and the filtrate was concentrated. The residue dissolved in ethyl acetate was washed with 0.01M hydrochloric acid, 0.01M aqueous sodium hydrogen carbonate solution, and brine. The oranic layer was dried and concentrated, and the residue was purified by silica gel column chromatography (solvent: ethyl acetate-hexane (3:2)) to obtain 156 mg of 4α-acetoxy-2α-benzoyloxy-5β,20-epoxy-1β,7β,10β-trihydroxy-13α-[(2R,3S)-3-phenyl-3-(t-butoxycarbonylamino)-2-hydroxypropionyloxy]-tax-11-en-9-one. Yield: 82%

$[\alpha]_D^{20}$=−48.37° (c=0.74, chloroform)

IR (nujol) $v_{max}$ (cm$^{-1}$): 3440, 1720

FAB-MS (m/z): 808 (MH$^+$)

$^1$H-NMR (CDCl$_3$) δ: 1.13 (3H, s), 1.24 (3H, s), 1.34 (9H, s), 1.58 (1H, br s), 1.69 (1H, s), 1.77 (3H, s), 1.85 (4H, s+m), 2.27 (2H, d, J=8.7 Hz), 2.37 (3H, s), 2.54 to 2.62 (1H, m), 3.37 (1H, d, J=5.5 Hz), 3.91 (1H, d, J=7.0 Hz), 4.19 and 4.32 (each 2H, d, J=8.5 Hz), 4.21 to 4.26 (2H, m), 4.61 (1H, br s), 4.94 (1H, d, J=7.7 Hz), 5.21 (1H, d, J=1.7 Hz), 5.27 (1H, br d, J=9 Hz), 5.43 (1H, d, J=9.3 Hz), 5.68 (1H, d, J=7.0 Hz), 6.21 (1H, t, J=9 Hz), 7.3 to 7.4 (5H, m), 7.50 (2H, t, J=7.4 Hz), 7.61 (1H, d, J=7.4 Hz), 8.10 (2H, d, J=7.4 Hz)

Example 2

(1) Under argon atmosphere, in 70 ml of toluene was dissolved 4.92 g of 4α-acetoxy-2α-benzoyloxy-5β,20-epoxy-1β,13α-dihydroxy-7β,10β-di(2,2,2-trichloroethoxycarbonyloxy)-tax-11-en-9-one. To the solution were added 1.79 g of (2R,3S)-3-phenylepoxypropionic acid, 2.38 g of N,N'-dicyclohexylcarbodiimide and 342 mg of 4-(N,N-dimethylamino)pyridine at room temperature, and the mixture was stirred for 10 minutes. The reaction mixture was concentrated under reduced pressure, and the residue was purified by silica gel flash column chromatography (solvent: toluene-ethyl acetate (15:1)) to obtain 5.55 g of 4α-acetoxy-2α-benzoyloxy-5β,20-epoxy-1β-hydroxy-7β,10β-di(2,2,2-trichloroethoxycarbonyloxy)-13α-[(2R,3S)-3-phenyl-2,3-epoxypropionyloxy]-tax-11-en-9-one. Yield: 97%

IR (nujol) $v_{max}$ (cm$^{-1}$): 3520, 1760, 1730

FAB-MS (m/z): 1039 (MH$^+$)

$^1$H-NMR (CDCl$_3$) δ: 1.21 (3H, s), 1.28 (3H, s), 1.73 (1H, s), 1.86 (3H, s), 2.01 to 2.13 (1H, m), 2.09 (3H, s), 2.20 to 2.41 (2H, m), 2.22 (3H, s), 2.63 (1H, m), 3.64 (1H, d, J=1.7 Hz), 3.92 (1H, d, J=6.9 Hz), 4.16 (1H, d, J=8.2 Hz), 4.22 (1H, d, J=1.7 Hz), 4.32 (1H, d, J=8.2 Hz), 4.61 (1H, d, J=11.8 Hz), 4.79 (2H, s), 4.92 (1H, d, J=11.8 Hz), 4.94 (1H, m), 5.57 (1H, dd, J=7.1, 10.7 Hz), 5.69 (1H, d, J=6.9 Hz), 6.27 (1H, s), 6.31 (1H, m), 7.30 to 7.66 (8H, m), 8.07 (2H, m)

(2) Under argon atmosphere, 2.70 g of 4α-acetoxy-2α-benzoyloxy-5β,20-epoxy-1β-hydroxy-7β,10β-di(2,2,2-trichloroethoxycarbonyloxy)-13α-[(2R,3S)-3-phenyl-2,3-epoxypropionyloxy]-tax-11-en-9-one was dissolved in a mixed solvent of 50 ml of dichloromethane and 5 ml of hexamethylphosphoric triamide. The solution was cooled by an ice-acetone bath, and 2.80 g of titanium tetrabromide was added to the solution. Thereafter, the mixture was stirred for 18 hours while cooling by an ice bath. 100 ml of water was added to the reaction mixture, and the mixture was stirred for 10 minutes. The organic layer was separated and concentrated under reduced pressure. The residue was dissolved in 50 ml of ethyl acetate, 25 ml of hexane and 50 ml of water, and the organic layer was separated. After the organic layer was further washed with water and dried, the solvent was removed, and the residue was purified by silica gel flash column chromatography (solvent: hexane-ethyl acetate (2:1)) to obtain 2.22 g of 4α-acetoxy-2α-benzoyloxy-5β,20-epoxy-1β-hydroxy-7β,10β-di(2,2,2-trichloroethoxycarbonyloxy)-13α-[(2S,3R)-3-phenyl-3-bromo-2-hydroxypropionyloxy]-tax-11-en-9-one. Yield: 76%

IR (nujol) $v_{max}$ (cm$^{-1}$): 3440, 1760, 1720

FAB-MS (m/z): 1119, 1121 (MH$^+$)

$^1$H-NMR (CDCl$_3$) δ: 1.19 (3H, s), 1.25 (3H, s), 1.74 (1H, s), 1.81 (3H, d, J=1 Hz), 1.85 (3H, s), 2.06 (1H, m), 2.28 (2H, m), 2.39 (3H, s), 2.63 (1H, m), 2.99 (1H, d, J=7 Hz), 3.90 (1H, d, J=7 Hz), 4.16 (1H, d, J=8 Hz), 4.34 (1H, d, J=8 Hz), 4.60 (1H, d, J=12 Hz), 4.77 (2H, s), 4.78 (1H, dd, J=6, 7 Hz), 4.91 (1H, d, J=12 Hz), 4.97 (1H, m), 5.27 (1H, d, J=6 Hz), 5.53 (1H, dd, J=7, 11 Hz), 5.68 (1H, d, J=7 Hz), 6.17 (1H, m), 6.21 (1H, s), 7.4 to 7.5 (7H, m), 7.64 (1H, m), 8.07 (2H, m)

(3) In 2 ml of dimethylformamide was dissolved 112 mg of 4α-acetoxy-2α-benzoyloxy-5β,20-epoxy-1β-hydroxy-7β,10β-di(2,2,2-trichloroethoxycarbonyloxy)-13α-[(2S,3R)-3-phenyl-3-bromo-2-hydroxypropionyloxy]-tax-11-en-9-one, and 2 mg of 1,4,7,10,13-pentaoxacyclopentadecane was added to the solution. The mixture was cooled by an outer bath at −15° to −10° C., and 65 mg of sodium azide was added thereto. The mixture was stirred for 18 hours while cooling by an ice bath. The reaction mixture was poured into cool water and extracted with ethyl acetate. The organic layer was washed with brine and then dried over anhydrous sodium sulfate, and the solvent was removed under reduced pressure. The residue was purified by silica gel thin layer chromatography (solvent: ethyl acetate-hexane (2:3)) to obtain 77 mg of 4α-acetoxy-2α-benzoyloxy-5β,20-epoxy-1β-hydroxy-7β,10β-di(2,2,2-trichloroethoxycarbonyloxy)-13α-[(2R,3S)-3-phenyl-3-azido-2-hydroxypropionyloxy]-tax-11-en-9-one. Yield: 71% The physical property values were the same as those of the compound obtained in Example 1-(3-1).

Example 3

In 2 ml of dimethylformamide was dissolved 100 mg of 4α-acetoxy-2α-benzoyloxy-5β,20-epoxy-1β-hydroxy-7β,10β-di(2,2,2-trichloroethoxycarbonyloxy)-13α-[(2S,3R)-3-phenyl-3-bromo-2-hydroxypropionyloxy]-tax-11-en-9-one, and 0.12 ml of azidotrimethylsilane was added to the solution. The mixture was stirred in an outer bath at 50° C. for 2 hours. 29 mg of sodium azide was added to the reaction mixture, and the mixture was further stirred in an outer bath at 50° C. for 18 hours. The reaction mixture was poured into ice water and extracted with ethyl acetate. After the organic layer was washed with brine and dried over anhydrous sodium sulfate, the solvent was removed under reduced pressure. The residue was dissolved in 5 ml of ethanol. While cooling by an ice bath, an about 15% hydrogen chloride-ethanol solution was added to the solution, and the mixture was further stirred for 10 minutes. The reaction mixture was poured into ice water and extracted with ethyl acetate. The organic layer was washed with a saturated aqueous sodium hydrogen carbonate solution and then brine and dried over anhydrous sodium sulfate, and the solvent was removed under reduced pressure. The residue was purified by silica gel thin layer chromatography (solvent: ethyl acetate-hexane (2:3)) to obtain 63 mg of 4α-acetoxy-2α-benzoyloxy-5β,20-epoxy-1β-hydroxy-7β,10β-di(2,2,2-trichloroethoxycarbonyloxy)-13α-[(2R,3S)-3-phenyl-3-azido-2-hydroxypropionyloxy]-tax-11-en-9-one. Yield: 65% The physical property values were the same as those of the compound obtained in Example 1-(3-1).

Example 4

(1) Under argon atmosphere, a solution of methyl (2S,3R)-2,3-dihydroxy-3-(4-fluorophenyl)propionate (3.95 g, 18.4 mmol) dissolved in dichloromethane (100 ml) was cooled to −3° to −5° C., and triethylamine (3.86 ml, 27.7 mmol) and p-toluenesulfonyl chloride (3.62 g, 19.0 mmol) were added to the solution. After the mixture was stirred at −3° to −5° C. for 44 hours, the reaction mixture was washed with water and brine. After the organic layer was dried over anhydrous sodium sulfate, the solvent was removed, and the residue obtained was purified by silica gel flash column chromatography (ethyl acetate/hexane=1/2) to obtain methyl (2S,3R)-3-(4-fluorophenyl)-3-hydroxy-2-p-toluenesulfonyloxypropionate (5.64 g, yield: 83%).

m.p.: 122.5° to 123.5° C.

IR (nujol) $v_{max}$ (cm$^{-1}$): 3500, 1770, 1140, 730

FAB-MS (NaCl added) (m/z): 391 (M$^+$+Na)

$^1$H-NMR (300 MHz, CDCl$_3$) δ: 2.43 (3H, s), 2.66 (1H, d, J=6 Hz), 3.64 (3H, s), 4.88 (1H, d, J=4 Hz), 5.11 (1H, t-like), 6.87 to 6.95 (2H, m), 7.17 to 7.25 (4H, m), 7.55 to 7.60 (2H, m)

(2) In dimethylformamide (75 ml) was dissolved methyl (2S,3R)-3-(4-fluorophenyl)-3-hydroxy-2-p-toluenesulfonyloxypropionate (5.48 g, 14.9 mmol), and water (1.4 ml, 74.5 mmol) was added to the solution. The reaction mixture was cooled by an ice bath, potassium carbonate (6.16 g, 44.6 mmol) was added thereto, and the mixture was stirred at room temperature for 22 hours. The reaction mixture was cooled again by an ice bath, water (100 ml) was added thereto, and the mixture was extracted with ethyl acetate. The organic layer was washed with brine and then dried over anhydrous sodium sulfate. After the solvent was removed, the residue obtained was purified by silica gel column chromatography (diethyl ether/hexane=1/3) to obtain methyl (2R,3R)-3-(4-fluorophenyl)-2,3-epoxypropionate (2.69 g, yield: 92%).

IR (nujol) $v_{max}$ (cm$^{-1}$): 1740, 1510

EI-MS (m/z): 196 (M$^+$)

$^1$H-NMR (300 MHz, CDCl$_3$) δ: 3.57 (3H, s), 3.82 (1H, d, J=5 Hz), 4.24 (1H, d, J=5 Hz), 6.99 to 7.07 (2H, m), 7.36 to 7.44 (2H, m)

(3) A solution of methyl (2R,3R)-3-(4-fluorophenyl)-2,3-epoxypropionate (206 mg, 1.05 mmol) dissolved in 5 ml of methanol was cooled by an ice bath, and a solution of lithium hydroxide (30 mg, 1.26 mmol) dissolved in water (3 ml) was added to the above solution. After the mixture was stirred at room temperature for 1.5 hours, the reaction mixture was concentrated. While cooling by an ice bath, a 5% citric acid aqueous solution was added to the residue obtained, and the mixture was extracted with chloroform. The organic layer was washed with brine and then dried over anhydrous sodium sulfate. The solvent was removed to obtain (2R,3R)-3-(4-fluorophenyl)-2,3-epoxypropionic acid (which was unstable so that it could not be isolated nor purified).

Dichlorohexylcarbodiimide (227 mg, 1.10 mmol) and dimethylaminopyridine (14 mg, 0.12 mmol) were added to the solution of (2R,3R)-3-(4-fluorophenyl)-2,3-epoxypropionic acid and 4α-acetoxy-2α-benzoyloxy-5β-20-epoxy-1β,13α-dihydroxy-7β,10β-di (2,2,2-trichloroethoxycarbonyloxy)-tax-11-ene-9-one (235 mg, 0.26 mmol) in toluene. An outer bath was heated to 80° C., and the mixture was stirred for 2 hours. Thereafter, insolubles were removed by filtration, and the filtrate was concentrated. The residue obtained was purified by silica gel flash column chromatography (ethyl acetate/toluene=1/6) to obtain 4α-acetoxy-2α-benzoyloxy-5β-20-epoxy-1β-hydroxy-7β,10β-di(2,2,2-trichloroethoxycarbonyloxy)-13α-[(2R,3R)-3-(4-fluorophenyl)-2,3-epoxypropionyloxy]-tax-11-ene-9-one (167 mg, yield: 60%).

IR (nujol) $v_{max}$ (cm$^{-1}$): 1760, 1720, 1240, 720

FAB-MS (m/z): 1057 (MH$^+$) (1059 (MH$^+$+2), 1061 (MH$^+$+4))

$^1$H-NMR (300 MHz, CDCl$_3$) δ: 1.15 (3H, s), 1.16 (3H, s), 1.61 (1H, s), 1.83 (3H, s), 1.87 (3H, d, J=1 Hz), 2.0 to 2.1 (3H, m), 2.36 (3H, s), 2.63 (1H, m), 3.87 (1H, d, J=7 Hz), 3.95 (1H, d, J=4 Hz), 4.14 (1H, d, J=9 Hz), 4.30 (1H, d, J=4 Hz), 4.31 (1H, d, J=9 Hz), 4.61 (1H, d, J=12 Hz), 4.77 (2H, s), 4.92 (1H, d, J=12 Hz), 4.97 (1H, m), 5.56 (1H, dd, J=7, 11 Hz), 5.63 (1H, d, J=7 Hz), 6.01 to 6.08 (1H, m), 6.20 (1H, s), 7.07 (2H, m), 7.39 to 7.52 (4H, m), 7.60 to 7.68 (1H, m), 8.00 (2H, m)

(4) Methyl formate (0.7 ml) and sodium azide (432 mg, 6.64 mmol) were added to a solution of 4α-acetoxy-2α-benzoyloxy-5β-20-epoxy-1β-hydroxy-7β,10β-di(2,2,2-trichloroethoxycarbonyloxy)-13α-[(2R,3R)-3-(4-fluorophenyl)-2,3-epoxypropionyloxy]-tax-11-ene-9-one (235 mg, 0.22 mmol) dissolved in 11% aqueous methanol (7 ml). An outer bath was heated to 50° C., and the mixture was stirred for 24 hours. The reaction mixture was poured into ice water and extracted with ethyl acetate. The organic layer was washed with a 5% aqueous citric acid solution and then brine and dried over anhydrous sodium sulfate. The solvent was removed, and the residue obtained was purified by preparative thin layer chromatography to obtain 4α-acetoxy-2α-benzoyloxy-5β-20-epoxy-1β-hydroxy-7β,10β-di(2,2,2-trichloroethoxycarbonyloxy)-13α-[(2R,3S)-3-(4-fluorophenyl)-3-azido-2-hydroxypropionyloxy]-tax-11-ene-9-one (162 mg, yield: 67%).

IR (nujol) $v_{max}$ (cm$^{-1}$): 3480, 2110, 1760, 1720

FAB-MS (NaCl added) (m/z): 1122 (M$^+$+Na)

$^1$H-NMR (300 MHz, CDCl$_3$) δ: 1.22 (3H, s), 1.28 (3H, s), 1.74 (1H, s, D$_2$O exchange), 1.87 (3H, s), 2.12 (3H, d, J=1 Hz), 2.0 to 2.3 (3H, m), 2.31 (3H, s), 2.65 (1H, m), 3.21 (1H, d, J=8 Hz, D$_2$O exchange), 3.92 (1H, d, J=7 Hz), 4.18 (1H, d, J=8 Hz), 4.33 (1H, d, J=8 Hz), 4.42 (1H, dd, J=3, 8 Hz), 4.61 (1H, d, J=12 Hz), 4.76 (1H, d, J=12 Hz), 4.81 (1H, d, J=12 Hz), 4.93 (1H, d, J=12 Hz), 4.96 (1H, m), 5.03 (1H, d, J=3 Hz), 5.56 (1H, dd, J=7, 11 Hz), 5.69 (1H, d, J=7 Hz), 6.26 (1H, m), 6.28 (1H, s), 7.15 (2H, m), 7.47 (4H, m), 7.63 (1H, m), 8.06 (2H, m)

(5) To a solution of 4α-acetoxy-2α-benzoyloxy-5β-20-epoxy-1β-hydroxy-7β,10β-di(2,2,2-trichloroethoxycarbonyloxy)-13α-[(2R,3S)-3-(4-fluorophenyl)-3-azido-2-hydroxypropionyloxy]-tax-11-ene-9-one (81 mg, 0.073 mmol) dissolved in dichloromethane (3 ml) were added triphenylphosphine (39 mg, 0.149 mmol), water (0.05 ml), di-t-butyl dicarbonate (48 mg, 0.22 mmol) and potassium bicarbonate (37 mg, 0.37 mmol), and the mixture was stirred at room temperature for 22 hours. The reaction mixture was diluted with chloroform and washed with water and brine. After the organic layer was dried over anhydrous sodium sulfate, the solvent was removed. The residue obtained was purified by preparative thin layer chromatography to obtain 4α-acetoxy-2α-benzoyloxy-5β-20-epoxy-1β-hydroxy-7β,10β-di(2,2,2-trichloroethoxycarbonyloxy)-13α-[(2R,3S)-3-(4-fluorophenyl)-2-hydroxy-3-t-butoxycarbonylaminopropionyloxy]-tax-11-ene-9-one (33 mg, yield: 39%).

IR (nujol) $v_{max}$ (cm$^{-1}$): 3400, 1760, 1730

FAB-MS (m/z): 1174 (MH$^+$)

$^1$H-NMR (300 MHz, CDCl$_3$) δ: 1.21 (3H, s), 1.28 (3H, s), 1.35 (9H, s), 1.73 (1H, s, D$_2$O exchange), 2.1 (1H, m), 1.86 (3H, s), 1.96 (3H, s), 2.3 (2H, m), 2.36 (3H, s), 2.6 (1H, m), 3.41 (1H, d, J=5 Hz, D$_2$O exchange), 3.91 (1H, d, J=7 Hz), 4.18 (1H, d, J=8 Hz), 4.34 (1H, d, J=8 Hz), 4.60 (1H, m), 4.60 (1H, d, J=12 Hz), 4.78 (2H, s), 4.91 (1H, d, J=12 Hz), 4.96 (1H, m), 5.26 (1H, br), 5.36 (1H, m), 5.54 (1H, m), 5.70 (1H, d, J=7 Hz), 6.23 (1H, m), 6.25 (1H, s), 7.05 to 7.40 (4H, m), 7.50 (2H, m), 7.63 (1H, m), 8.10 (2H, m)

(6) Zinc powder (15 g) was added to a solution of 4α-acetoxy-2α-benzoyloxy-5β-20-epoxy-1β-hydroxy-7β,10β-di(2,2,2-trichloroethoxycarbonyloxy)-13α-[(2R,3S)-3-(4-fluorophenyl)-2-hydroxy-3-t-butoxycarbonylaminopropionyloxy]-tax-11-ene-9-one (6.42 g, 5.46 mmol) dissolved in methanol (200 ml) and acetic acid (50 ml). An outer bath was heated to 60° C., and the mixture was stirred for 30 minutes. Zinc powder was removed from the reaction mixture by filtration, and the filtrate was concentrated. The residue was dissolved in ethyl acetate and washed with a 1% HCl aqueous solution, a saturated aqueous sodium hydrogen carbonate solution and brine. After the organic layer was dried over anhydrous sodium sulfate, the solvent was removed. The residue obtained was purified by silica gel flash column chromatography (ethyl acetate/hexane=3/2) to obtain 4α-acetoxy-2α-benzoyloxy-5β-20-epoxy-1β,7β,10β-trihydroxy-13α-[(2R,3S)-3-(4-fluorophenyl)-2-hydroxy-3-t-butoxycarbonylaminopropionyloxy]-tax-11-ene-9-one (2.61 g, yield: 58%).

m.p.: 159° C. (slowly decomposed)

IR (nujol) $v_{max}$ (cm$^{-1}$): 3440, 1710, 1460

FAB-MS (m/z): 826 (MH$^+$)

$^1$H-NMR (300 MHz, CDCl$_3$) δ: 1.13 (3H, s), 1.24 (3H, s), 1.34 (9H, s), 1.73 (1H, s, D$_2$O exchange), 1.75 (1H, d-like, D$_2$O exchange), 1.76 (3H, s), 1.83 (1H, m), 1.86 (3H, d, J=1 Hz), 2.29 (2H, m), 2.36 (3H, s), 2.58 (1H, m), 3.49 (1H, d, J=5 Hz, D$_2$O exchange), 3.92 (1H, d, J=7 Hz), 4.19 (1H, d, J=8 Hz), 4.22 (1H, m), 4.23 (1H, d, J=2 Hz, D$_2$O exchange), 4.32 (1H, d, J=8 Hz), 4.58 (1H, m), 4.94 (1H, m), 5.21 (1H, d, J=2 Hz), 5.25 (1H, br), 5.43 (1H, br, D$_2$O exchange), 5.68 (1H, d, J=7 Hz), 6.24 (1H, m), 7.08 (2H, m), 7.38 (2H, m), 7.49 (2H, m), 7.61 (1H, m), 8.10 (2H, m)

Example 5

(1) While cooling by an ice-acetone bath, a solution of 262 mg of di-tert-butyl bicarbonate dissolved in 5 ml of tetrahydrofuran was added dropwise to a mixture of 663 mg of 4α-acetoxy-13α-[(2R,3S)-3-amino-2-hydroxy-3-phenylpropionyloxy]-2α-benzoyloxy-5β,20-epoxy-1β-hydroxy-7β,10β-bis(2,2,2-trichloroethoxycarbonyloxy)tax-11-en-9-one.formate, 151 mg of sodium hydrogen carbonate and 15 ml of tetrahydrofuran, and then the mixture was stirred at room temperature for 18 hours. Insolubles were removed by filtration, the filtrate was concentrated under reduced pressure, and then the residue was dissolved in ethyl acetate. After the ethyl acetate layer was washed with water and brine, and dried, the solvent was removed. The residue was purified by silica gel column chromatography (solvent; hexane:ethyl acetate=2:1) to obtain 523 mg of 4α-acetoxy-13α-[(2R,3S)-3-tert-butoxycarbonylamino-2-hydroxy-3-phenylpropionyloxy]-2α-benzoyloxy-5β,20-epoxy-1β-hydroxy-7β,10β-bis(2,2,2-trichloroethoxycarbonyloxy)tax-11-en-9-one. The physical property values were coincident with those of Compound 7a of "Tetrahedron", Vol. 45, p. 4177 (1989).

(2) ((3S)-3-benzyloxycarbonylamino-3-ethoxycarbonylpropionyloxy)acetic acid (185 mg), 129 mg of N,N'-dicyclohexylcarbodiimide and 5 mg of 4-dimethylaminopyridine were added to a solution of 505 mg of 4α-acetoxy-13α-[(2R,3S)-3-tert-butoxycarbonylamino-2-hydroxy-3-phenylpropionyloxy]-2α-benzoyloxy-5β,20-epoxy-1β-hydroxy-7β,10β-bis(2,2,2-trichloroethoxycarbonyloxy)tax-11-en-9-one dissolved in 20 ml of tetrahydrofuran, and the mixture was stirred at room temperature for 4 hours. Precipitates were removed by filtration, the filtrate was concentrated under reduced pressure, and the residue was dissolved in ethyl acetate. After the ethyl acetate layer was washed with water and brine, and dried, the solvent was removed. The residue was purified by silica gel column chromatography (solvent; hexane:ethyl acetate=2:1) to obtain 434 mg of 4α-acetoxy-13α-{(2R,3S)-3-tert-butoxycarbonylamino-2-[((3S)-3-benzyloxycarbonylamino-3-ethoxycarbonylpropionyloxy)acetoxy]-3-phenylpropionyloxy}-2α-benzoyloxy-5β,20-epoxy-1β-hydroxy-7β,10β-bis(2,2,2-trichloroethoxycarbonyloxy)tax-11-en-9-one.

IR (nujol) $v_{max}$ (cm$^{-1}$): 3360, 1760, 1730

FAB-MS (m/z): 1491 (MH$^+$)

(3) Zinc (1 g) was added to a solution of 412 mg of 4α-acetoxy-13α-{(2R,3S)-3-tert-butoxycarbonylamino-2-[((3S)-3-benzyloxycarbonylamino-3-ethoxycarbonylpropionyloxy)acetoxy]-3-phenylpropionyloxy}-2α-benzoyloxy-5β,20-epoxy-1β-hydroxy-7β,10β-bis(2,2,2-trichloroethoxycarbonyloxy)tax-11-en-9-one dissolved in methanol-acetic acid (12 ml-3 ml), and the mixture was stirred at 60° C. for 30 minutes. After the reaction mixture was cooled, zinc was removed by filtration. After the filtrate was concentrated under reduced pressure, the residue was dissolved in ethyl acetate. After the ethyl acetate layer was washed with a 1% aqueous HCl solution, a saturated aqueous sodium hydrogen carbonate solution and brine, and dried, the solvent was removed. The residue was purified by silica gel column chromatography (solvent; hexane:ethyl acetate=1:2) to obtain 220 mg of 4α-acetoxy-13α-{(2R,3S)-3-tert-butoxycarbonylamino-2-[(3S)-3-benzyloxycarbonylamino-3-ethoxycarbonylpropionyloxyacetoxy]-3-phenylpropionyloxy}-2α-benzoyloxy-5β,20-epoxy-1β,7β,10β-trihydroxytax-11-en-9-one.

m.p.: 130° to 134° C.

FAB-MS (m/z): 1143 (MH$^+$)

IR (nujol) $v_{max}$ (cm$^{-1}$): 3400, 1720

$^1$H-NMR (CDCl$_3$) δ: 1.12 (3H, s), 1.21 (3H, s), 1.24 (3H, t, J=7 Hz), 1.34 (9H, s), 1.58 (1H, m), 1.64 (1H, s), 1.75 (3H, s), 1.85 (1H, m), 1.92 (3H, s), 2.15 (1H, m), 2.25 (1H, m), 2.35 (3H, s), 2.59 (1H, m), 2.92 (1H, dd, J=5, 17 Hz), 3.11 (1H, dd, J=4, 17 Hz), 3.90 (1H, d, J=7 Hz), 4.15 to 4.25 (5H, m), 4.30 (1H, d, J=8 Hz), 4.57 to 4.70 (3H, m), 4.95 (1H, m), 5.12 (2H, s), 5.19 (1H, s), 5.45 to 5.55 (3H, m), 5.67 (1H, d, J=7.0 Hz), 5.91 (1H, br), 6.20 (1H, m), 7.28 to 7.42 (10H, m), 7.50 (2H, m), 7.62 (1H, m), 8.10 (2H, m)

Example 6

(1) Zinc (11.12 q) was added to a solution of 5.63 g of 4α-acetoxy-13α-[(2R,3S)-3-tert-butoxycarbonylamino-2-hydroxy-3-phenylpropionyloxy]-2α-benzoyloxy-5β,20-epoxy-1β-hydroxy-7β,10β-bis(2,2,2-trichloroethoxycarbonyloxy)tax-11-en-9-one dissolved in methanol-acetic acid (220 ml-50 ml), and the mixture was stirred at 60° C. for 1.5 hours. After the reaction mixture was cooled, zinc was removed by filtration. The filtrate was concentrated under reduced pressure, and the residue was dissolved in ethyl acetate. After the ethyl acetate layer was washed with a 1% aqueous HCl solution, a saturated aqueous sodium hydrogen carbonate solution and brine, and dried, the solvent was removed. The residue was purified by silica gel column chromatography (solvent; hexane:ethyl acetate=1:1 to 1:2) and then crystallized from hexane to obtain 2.86 g of 4α-acetoxy-13α-[(2R,3S)-3-tert-butoxycarbonylamino-2-hydroxy-3-phenylpropionyloxy]-2α-benzoyloxy-5β,20-epoxy-1β,7β,10β-trihydroxytax-11-en-9-one. The physical property values were coincident with those of Compound 10a of "Tetrahedron", Vol. 45, p. 4177 (1989).

(2) Under argon atmosphere, a solution of 328 mg of ((3S)-3-benzyloxycarbonylamino-3-ethoxycarbonylpropionyloxy)acetic acid dissolved in 3 ml of tetrahydrofuran was cooled by an ice-acetone bath. To the solution were added 123 mg of isopropyl chloroformate and 94 mg of triethylamine, and the mixture was stirred at 0° C. or lower for 30 minutes. To the reaction mixture was added dropwise a solution of 150 mg of 4α-acetoxy-13α-[(2R,3S)-3-tert-butoxycarbonylamino-2-hydroxy-3-phenylpropionyloxy]-2α-benzoyloxy-5β,20-epoxy-1β,7β,10β-trihydroxytax-11-en-9-one dissolved in 3 ml of tetrahydrofuran, and the mixture was stirred at 0° C. or lower for 4 hours. To the reaction mixture was added a saturated aqueous sodium hydrogen carbonate solution, and extracted with ethyl acetate. After the organic layer was washed with water and brine, and dried, the solvent was removed. The residue was purified by silica gel column chromatography (solvent; hexane:ethyl acetate=2:3) to obtain 167 mg of 4α-acetoxy-13α-{(2R,3S)-3-tert-butoxycarbonylamino-2-[((3S)-3-benzyloxycarbonylamino-3-ethoxycarbonylpropionyloxy)acetoxy]-3-phenylpropionyloxy}-2α-benzoyloxy-5β,20-epoxy-1β,7β,10β-trihydroxytax-11-en-9-one. The physical property values were the same as described in Example 5-(3).

Examples 7 to 31

By processing corresponding starting compounds in the same manner as in Example 5 or 6, the compounds shown in Tables 1 to 11 were obtained (in the tables, C$_6$H$_5$ represents phenyl group).

TABLE 1

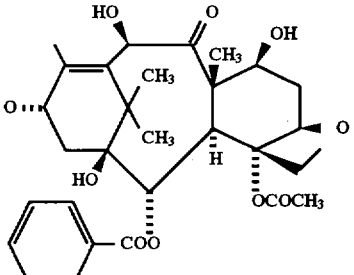

| Example No. | Y | Physical properties |
|---|---|---|
| 7 | 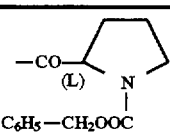 | m.p.: 140 to 148° C.<br>FAB-MS (m/z); 1097 (MH⁺)<br>IR (nujol)υ$_{max}$(cm⁻¹) : 3440, 1760, 1700<br>¹H-NMR (CDCl₃) δ: 1.12 (3H, s), 1.22 (3H, s), 1.27 (9H, s), 1.57 to 1.62 (2H, br), 1.66 (1H, s), 1.76 (3H, s), 1.80 to 2.10 (5H, m), 2.14 to 2.31 (2H, m), 2.48 (3H, s), 2.52 to 2.62 (1H,m), 3.41 to 3.66 (2H, m), 3.86 to 3.97 (1H, m), 4.16 to 4.31 (5H, m), 4.36 to 4.55 (1H, m), 4.62 (1H, d, J = 16Hz), 4.73 (1H, d, J = 16Hz), 4.93 to 5.00 (1H, m), 5.17 (2H, s), 5.22 (1H, s), 5.33 to 5.52 (1H, m), 5.55 to 5.62 (1H, m), 5.69 (1H, d, J = 7Hz), 6.17 to 6.31 (1H, m), 7.24 to 7.43 (10H, m) 7.45 to 7.53 (2H, m), 7.55 to 7.64 (1H, m), 8.10 to 8.14 (2H, m) |
| 8 | 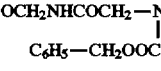 | m.p. : 161 to 163° C.<br>FAB-MS (m/z): 1136 (M⁺ + Na)<br>IR (nujol)υ$_{max}$(cm⁻¹) : 3360, 1760, 1710<br>¹H-NMR (CDCl₃) δ: 1.11 (3H, s), 1.19 (3H, s), 1.33 (9H, s), 1.62 to 1.65 (2H, m), 1.74 (3H, s), 1.89 (3H, s), 1.8 to 1.95 (1H, m), 2.05 to 2.6 (3H, m), 2.41 (3H, s), 3.80 to 3.89 (4H, m), 4.02 (1H, br), 4.10 to 4.15 (1H, m), 4.19 (1H, d, J = 8.6 Hz), 4.22 (2H, s), 4.21 to 4.28 (1H, m), (1H, m), 4.30 (1H, d, J = 8.6Hz), 4.58 (1H, m), 4.79 (1H, m), 4.95 (1H, d, J = 8.7Hz), 5.12 (2H, s), 5.23 (1H, br s), 5.40 (1H, br s), 5.48 (1H, m), 5.66 (1H, d, J = 7.2 Hz), 5.72 (1H, br s), 5.99 (1H, d, J = 9.1 Hz), 6.19 (1H, m), 6.77 (1H, br s), 7.28 to 7.42 (10H, m), 7.51 (2H, t-like), 7.62 (1H, t-like), 8.21 (2H, d-like) |

TABLE 2

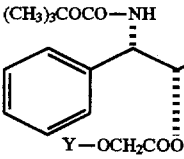

| Example No. | Y | Physical properties |
|---|---|---|
| 9 | 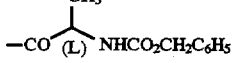 —CO—O—CH₂—CH(NHCO₂CH₂C₆H₅)(L)—CO₂(CH₂)₂OCH₃ | FAB-MS (m/z): 1172 (MH⁺)<br>IR (nujol)$\upsilon_{max}$(cm⁻¹): 3440, 3360, 1750, 1710<br>¹H-NMR (CDCl₃) δ: 1.11 (3H, s), 1.20 (3H, s), 1.34 (9H, s), 1.62 (7H, s), 1.75 (3H, s), 1.84 (1H, m), 1.92 (3H, s), 2.1 to 2.3 (2H, m), 2.32 (3H, s), 2.58 (1H, m), 2.94 (1H, m), 3.13 (1H, m), 3.33 (3H, s), 3.56 (2H, m), 3.89 (1H, d, J = 7Hz), 4.17 (1H, m), 4.20 (1H, s), 4.29 (4H, m), 4.61 (1H, d, J = 16Hz), 4.69 (1H, d, J = 16Hz), 4.73 (1H, m), 4.95 (1H, d, J = 9Hz), 5.11 (2H, s), 5.19 (1H, s), 5.46 (2H, m), 5.54 (1H, br), 5.67 (1H, d, J = 7Hz), 6.00 (1H, br s), 6.18 (1H, t-like), 7.36 (10H, m), 7.50 (2H, t-like), 7.62 (1H, t-like), 8.09 (2H, d-like) |
| 10 | —CO—CH(CH₃)(L)—NHCO₂CH₂C₆H₅ | m.p. 141 to 144° C.<br>FAB-MS (m/z): 1071 (MH⁺)<br>IR (nujol)$\upsilon_{max}$(cm⁻¹): 3340, 1750, 1710<br>¹H-NMR (CDCl₃) δ: 1.12 (3H, s), 1.21 (3H, s) 1.31 (9H, s), 1.41 (3H, d, J = 7.4Hz) 1.45 (1H, d, J = 7.2Hz), 1.67 (1H, s) 1.75 (3H, s), 1.85 (1H, m), 1.93 (3H, s), 2.1 to 2.4 (2H, m), 2.43 (3H, s), 2.58 (1H, m), 3.92 (1H, d, J = 6.9Hz), 4.19 (1H, d, J = 8.6Hz), 4.22 to 4.30 (1H, m), 4.32 (1H, d, J = 8.6 Hz), 4.35 to 4.41 (1H, m), 4.61 (1H, d, J = 15.9Hz), 4.68 to 4.75 (1H, m), 4.79 (1h, d, J = 15.9Hz), 4.96 (1H, d, J = 9.6Hz), 5.13 (2H, s), 5.2 (1H, br s), 5.21 (1H, s), 5.44 (1H, m), 5.53 (1H, m), 5.68 (1H, d, J = 6.9Hz), 5.88 (1H, d, J = 10.4Hz), 6.22 (1H, m), 7.25 to 7.45 (10H, m), 7.49 (2H, m), 7.60 m), 8.11 (2H, m) |

TABLE 3

Structure: Taxane derivative with (CH₃)₃COCO—NH group, phenyl, and Y—O(CH₂)₄COO— substituent

| Example No. | Y | Physical properties |
|---|---|---|
| 11 | —CO—CH(CO₂CH₂CH₃)—CH₂—O— (L), NHCO₂CH₂C₆H₅ | FAB-MS (m/z): 1185 (MH⁺)<br>IR (nujol)υ$_{max}$(cm⁻¹): 3440, 3360, 1720<br>¹H-NMR (CDCl₃) δ: 1.12 (3H, s), 1.23 (3H, s), 1.26 (3H, t-like), 1.33 (9H, s), 1.58 (6H, m), 1.76 (3H, s), 1.85 (1H, m), 1.95 (3H, s), 2.1 to 2.3 (2H, m), 2.43 (3H, s), 2.59 (1H, m), 2.85 (1H, m) 3.03 (1H, m), 3.93 (1H, d, J = 7Hz) 4.11 (2H, m), 4.2 to 4.3 (8H, m), 4.60 (1H, m), 4.97 (1H, d, J = 10 Hz), 5.12 (2H, s), 5.22 (1H, s-like), 5.38 (1H, m), 5.46 (2H, m), 5.69 (1H, d, J = 7Hz), 5.77 (1H, br), 6.24 (1H, m), 7.35 (10H, m), 7.51 (2H, t-like), 7.61 (1H, t-like), 8.12 (2H, d-like) |

TABLE 4

Structure: Taxane derivative with C₆H₅—CO—NH group, phenyl, and Y—OCH₂COO— substituent

| Example No. | Y | Physical properties |
|---|---|---|
| 12 | —CO—CH₂—CH₂—O—, NHCO₂CH₂C₆H₅ | m.p.: 117 to 119° C.<br>FAB-MS (m/z): 1097 (M⁺+Na)<br>IR (nujol)υ$_{max}$(cm⁻¹) : 3400, 1740, 1710<br>¹H-NMR (CDCl₃) δ: 1.10 (3H, s), 1.18 (3H, s), 1.58 (1H, m), 1.67 (1H, s), 1.75 (3H, s), 1.89 (3H, s), 1.8 to 1.9 (1H, m), 2.12 (1H, dd, J = 9, 15Hz), 2.31 (1H, dd, J = 9, 15Hz), 2.40 (3H, s), 2.57 (1H, ddd, J = 7.0, 9.7, 13.4Hz), 2.61 (2H, t, J = 6Hz), 3.42 to 3.57 (2H, m), 3.90 (1H, d, J = 7Hz), 4.15 to 4.27 (2H, m), 4.20 (1H, d, J = 8.5Hz), 4.32 (1H, d, J = 8.5Hz), 4.69 (1H, d, J = 15.9Hz), 4.76 (1H, d, J = 15.9Hz), 4.95 (1H, dd, J = 1.6, 9.7Hz), 5.06 (2H, s), 5.08 (1H, s), 5.52 (1H, d, J = 2.8Hz), 5.60 (1H, d, J = 7.0Hz), 5.98 (1H, dd, J = 2.8, 9.1Hz), 6.20 (1H, dd, J = 9, 9Hz), 6.92 (1H, d, J = 9.1Hz), 7.3 to 7.45 (12H, m), 7.47 to 7.55 (3H, m), 7.6 (1H, m), 7.74 (2H, m), 8.13 (2H, m) |

TABLE 4-continued

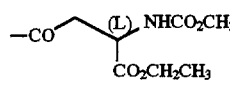

| Example No. | Y | Physical properties |
|---|---|---|
| 13 | $-CO-\underset{CO_2CH_2CH_3}{\overset{(L)\ NHCO_2CH_2C_6H_5}{\diagdown \diagup}}$ | FAB-MS (m/z): 1169 (M$^+$+Na)<br>IR (nujol)$\upsilon_{max}$(cm$^{-1}$): 3440, 3360, 1745, 2720<br>$^1$H-NMR (CDCl$_3$) δ: 1.90 (1H, s), 1.10 (3H, s), 1.16 (3H, s), 1.26 (3.H, t-like), 1.58 (1H, m), 1.67 (1H, s), 1.8 (1H, m), 1.76 (3H, s), 1.94 (3H, s), 2.1 to 2.3 (2H, m), 2.38 (3H, s), 2.6 (1H, m), 2.9 to 3.1 (2H, m), 3.90 (1H, d-like), 4.10 (2H, m), 4.21 (2H, m), 4.29 (2H, m), 4.67 (3H, m), 4.95 (1H, m), 5.05 (2H, s), 5.20 (1H, s), 5.67 (2H, m), 5.90 (1H, br), 5.96 (1H, s-like), 6.02 (1H, m), 6.21 (1H, m), 7.2 to 7.5 (16H, m), 7.60 (1H, m), 7.75 (2H, m), 8.13 (2H, d-like) |

TABLE 5

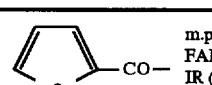

| Example No. | R$^5$ | Physical properties |
|---|---|---|
| 14 | ![furan]-CO— | m.p.; 119 to 135° C.<br>FAB-MS (m/z): 1137 (MH$^+$)<br>IR (nujol)$\upsilon_{max}$(cm$^{-1}$): 3400, 1750, 1720<br>$^1$H-NMR (CDCl$_3$) δ: 1.10 (3H, s), 1.17 (3H, s), 1.23 (3H, t, J = 7.2Hz), 1.58 to 1.62 (1H, r), 1.72 (1H, s), 1.75 (3H, s), 1.79 to 1.86 (1H, m), 1.89 (3H, s), 2.03 to 2.12 (1H, m), 2.22 to 2.29 (1H, m), 2.33 (3H, s), 2.52 to 2.69 (1H, m), 2.95 (1H, dd, J = 4.4, 17.1Hz), 3.12 (1H, dd, J = 4.4, 17.1Hz), 3.88 (1H, d, J = 7.0Hz), 4.14 to 4.33 (4H, m), 4.19 (2H, q, J = 7.2Hz), 4.62 to 4.73 (4H, m), 4.94 (1H, d, J = 8.8Hz), 5.08 (2H, s), 5.18 (1H, s), 5.65 (1H, d, J = 4.0Hz), 5.67 (1H, d, J = 7.0Hz), 5.93 (1H, dd, J = 4.0Hz), 5.67 (1H, d, J = 7.0Hz), 5.93 (1H, dd, J = 4.0, 9.3Hz), 5.98 (1H, d, J = 8.5 Hz), 6.17 (1H, t, J = 9.2Hz), 6.46 (1H, dd, J = 1.8, 3.5Hz), 7.04 (1H, d, J = 3.5Hz), 7.17 (1H, d, J = 9.3Hz), 7.28 to 7.44 (10H, m), 7.46 to 7.56 (2H, m), 7.47 (1H, d, J = 1.8Hz), 7.64 (1H, dd, J = 1.3, 7.4Hz), 8.11 to 8.16 (2H, m) |

TABLE 5-continued

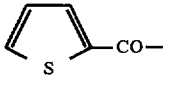

| Example No. | R⁵ | Physical properties |
|---|---|---|
| 15 | ![thiophene]-CO— (2-thienyl-CO—) | m.p.; 126 to 137° C.<br>FAB-MS (m/z): 1153 (MH⁺)<br>IR (nujol)$\upsilon_{max}$ (cm$^{-1}$) : 3400, 1740, 1720<br>$^1$H-NMR (DMSO-d$_6$) δ: 0.97 (3H, s), 0.98 (3H, s), 1.16 (3H, t, J = 7Hz), 1.34 to 1.47 (1H, m), 1.51 (3H, m), 1.59 to 1.79 (2H, m), 1.68 (3H, s), 2.19 (3H, s), 2.21 to 2.33 (1H, m), 2.71 to 2.90 (2H, m), 3.61 (1H, d, J = 7.9Hz), 3.95 to 4.14 (5H, m), 4.36 to 4.48 (2H, m), 4.82 (2H, br s), 4.84 to 4.93 (2H, m), 4.99 (1H, d, J.7.3Hz), 5.02 to 5.10 (3H, m), 5.34 to 5.41 (2H, m), 5.43 to 5.52 (1H, m), 5.81 (1H, t-like), 7.14 to 7.21 (2H, m), 7.28 to 7.47 (10H, m), 7.62 to 7.69 (2H, m), 7.73 (1H, d, J = 7.4Hz), 7.74 to 7.83 (1H, m), 7.87 (1H, d, J = 2.7Hz), 7.97 (2H, d, J = 7.0Hz) |

TABLE 6

| Example No. | R⁵ | Physical properties |
|---|---|---|
| 16 | Cl(CH$_2$)$_4$CO— | FAB-MS (m/z): 1160 (MH⁺)<br>IR (nujol)$\upsilon_{max}$ (cm$^{-1}$) : 3360, 1750, 1730<br>$^1$H-NMR (CDCl$_3$) δ: 1.12 (3H, s), 1.20 (3H, s), 1.26 (3H, t, J=7Hz), 1.50 (1H, d-like), 1.68 (4H, m), 1.75 (1H, s), 1.76 (3H, s), 1.84 (1H, m), 1.92 (3H, S), 2.13 (1H, m), 2.26 (3H, m), 2.40 (3H, s), 2.60 (1H, m), 2.94 (1H, m), 3.09 (1H, m), 3.37 (2H, m), 3.91 (1H, d, J=7Hz), 4.19 (1H, s), 4.2 to 4.3 (5H, m), 4.58 (1H, d, J=16Hz), 4.70 (1H, d, J=16Hz), 4.72 (1H, m), 4.95 (1H, d, J=9Hz), 5.11 (2H, m), 5.19 (1H, s), 5.54 (1H, m), 5.69 (1H, d, J=7Hz), 5.86 (1H, dd-like), 5.97 (1H, d, J=9Hz), 6.24 (1H, t-like), 6.83 (1H, d, J=10Hz), 7.34 (10H, m), 7.52 (2H, t-like), 7.62 (1H, t-like), 8.14 (2H, d-like) |

TABLE 6-continued

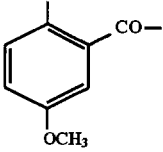

| Example No. | R⁵ | Physical properties |
|---|---|---|
| 17 | 2,5-dimethoxybenzoyl (OCH₃, OCH₃, CO—) | m.p.: 116 to 120° C.<br>FAB-MS (m/z) : 1207 (MH⁺)<br>IR (nujol)$\upsilon_{max}$(cm⁻¹) : 3360, 1760, 1720<br>¹H-NMR (CDCl₃) δ: 1.10 (3H, s), 1.21 (3H, s), 1.23 (3H, t, J=7.1Hz), 1.65 (1H, s), 1.68 (1H, d, J=7.6Hz), 1.76 (3H, s), 1.79 to 1.88 (1H, m), 1.90 (3H, s), 2.02 to 2.12 (1H, m), 2.23 to 2.33 (1H, m), 2.37 (3H, s), 2.52 to 2.68 (1H, m), 2.95 (1H, dd, J=4, 17Hz), 3.13 (1H, dd, J=A, 17Hz), 3.56 (3H, s), 3.89 (1H, d, J=7Hz), 3.98 (3H, s), 4.13 to 4.25 (4H, m), 4.25 to 4.34 (2H, m), 4.61 to 4.69 (1H, m), 4.63 (1H, d, J=16.0Hz), 4.79 (1H, d, J = 16.0Hz), 4.95 (1H, d, J=8.4Hz), 5.11 (2H, s), 5.18 (1H, s), 5.62 (1H, d, J=4.2Hz), 5.66 (1H, d, J=7Hz), 5.94 (1H, d, 7=B.4Hz), 6.00 (1H, dd, J=4.3, 8.7Hz), 6.18 (1H, t, J=9Hz), 6.94 (1H, d, J=9.0Hz), 6.99 (1H, dd, J=3.1, 9.0Hz), 7.29 to 7.42 (11H, m), 7.49 to 7.65 (3H, m), 8.12 to 8.17 (2H, m), 8.89 (1H, d, J=8.7Hz) |

35

TABLE 7

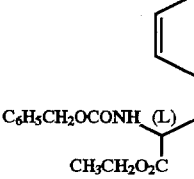

| Example No. | R⁵ | Physical properties |
|---|---|---|
| 18 | CH₃CH₂OCO— | FAB-MS (m/z): 1115 (MH⁺)<br>IR (nujol)$\upsilon_{max}$ (cm⁻¹) : 3360, 1750, 1720<br>¹H-NMR (CDCl₃) δ: 1.11 (3H, s), 1.13 (3H, t, J=7Hz), 1.20 (3H, s), 1.26 (3H, t, J=7Hz), 1.64 (1H, s), 1.72 (1H, s), 1.75 (3H, s), 1.85 (1H, m), 1.91 (3H, s), 2.24 (2H, m), 2.34 (3H, s), 2.58 (1H, m), 2.92 (1H, m), 3.12 (1H, m), 3.89 (1H, d, J=7Hz), 4.01 (2H, q, J=7Hz), 4.20 (1H, s), 4.2 to 4.3 (5H, m), 4.65 (2H, s), 4.67 (1H, m), 4.94 (1H, d, J=9Hz), 5.11 (2H, s), 5.19 (1H, s), 5.50 (2H, m), 5.66 (1H, d, J=7Hz), 5.85 (1H, br m), 5.97 (1H, br d), 6.21 (1H, m), 7.3 to 7.4 (10H, m), 7.49 (2H, t-like), 7.60 (1H, t- |

TABLE 7-continued

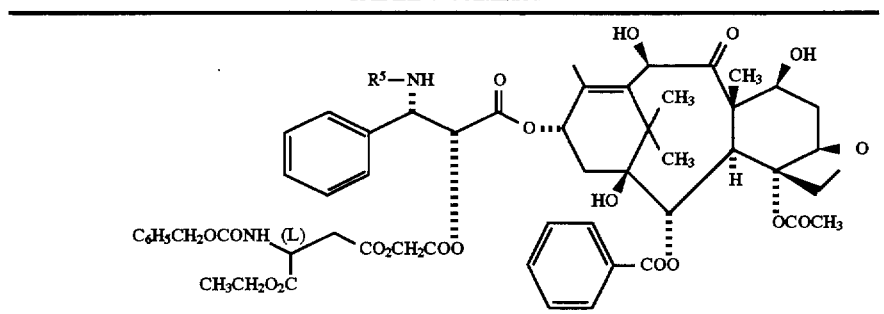

| Example No. | R[5] | Physical properties |
|---|---|---|
| 19 | 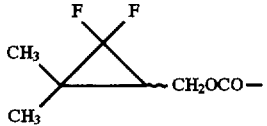 | like), 8.11 (2H, d, J=7Hz)<br>m.p.: 128 to 136° C.<br>FAB-MS (m/z): 1205 (MH+)<br>IR (nujol)υ$_{max}$(cm$^{-1}$): 3360, 1720<br>$^1$H-NMR (CDCl$_3$) δ: 0.97 (3H, s), 1.03 to 1.17 (6H, m), 1.11 (3H, s), 1.26 (3H, t, J=7.1Hz), 1.58 (1H, br), 1.60 (1H, s), 1.61 to 1.69 (1H, m), 1.75 (3H, s), 1.79 to 1.88 (1H, m), 1.91 (3H, s), 2.20 to 2.45 (5H, m), 2.50 to 2.60 (1H, m), 2.92 (1H, dd, J=4.2, 17.3Hz), 3.13 (1H, dd, J=4.2, 17.3Hz), 3.87 to 3.94 (1H, m), 4.01 to 4.07 (1H, m), 4.12 (2H, q, J=7.1 Hz), 4.16 to 4.32 (5H, m), 4.58 to 4.73 (3H, m), 4.94 (1H, d, J=7.8Hz), 5.12 (2H, s), 5.18 (1H, s), 5.52 (2.14, br s), 5.66 (1H, d, J=6.9Hz), 5.90 to 6.10 (2H, m), 6.18 to 6.20 (1H, m), 7.27 to 7.43 (10H, m), 7.47 to 7.54 (2H, m), 7.58 to 7.65 (1H, m), 8.12 (2H, d, J=8.0Hz) |

TABLE 8

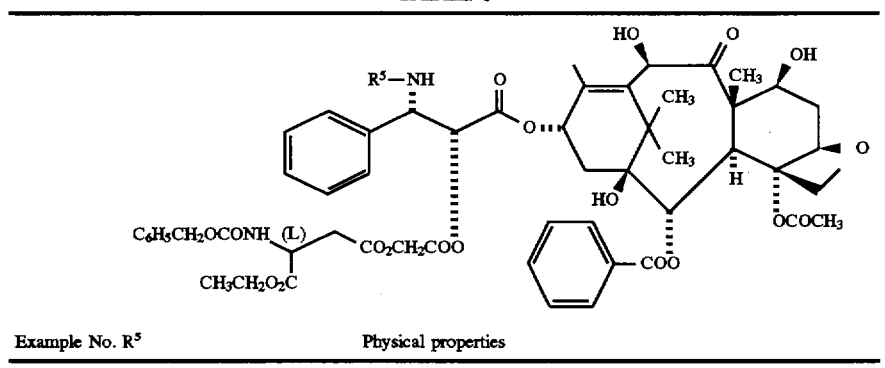

| Example No. | R[5] | Physical properties |
|---|---|---|
| 20 | CF$_3$CH$_2$OCO— | m.p.: 142 to 146° C.<br>FAB-MS (m/z): 1169 (MH+)<br>IR (nujol)υ$_{max}$ (cm$^{-1}$): 3400, 1740<br>$^1$H-NMR (CDCl$_3$) δ: 1.11 (3H, s), 1.20 (3H, s), 1.25 (3H, t, J=7Hz), 1.58 (1H, m), 1.65 (1H, s), 1.75 (3H, s), 1.78 to 1.91 (1H, m), 1.91 (3H, s), 1.93 to 2.05 (1H, m), 2.17 to 2.28 (1H, m), 2.34 (3H, s), 2.53 to 2.66 (1H, m), 2.84 to 2.97 (1H, m), 3.05 to 3.14 (1H, m), 3.90 (1H, d, J=7Hz), 4.14 to 4.41 (8H, m), 4.62 (1H, d, J=16Hz), 4.67 (1H, d, J=16Hz), 4.66 to 4.74 (1H, m), 4.94 (1H, d, J=9.4Hz), 5.12 (2H, s), 5.18 (1H, s), 5.45 to 5.55 (1H, m), 5.52 (1H, br s), 5.66 (1H, d, J=7Hz), 5.97 (1H, d, J=9Hz), 6.22 (1H, t-like), 6.40 (1H, d, J=9Hz), 7.26 to 7.43 (10H, |

TABLE 8-continued

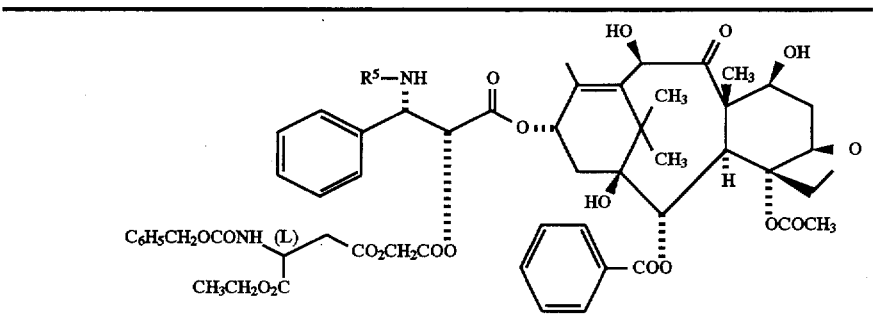

| Example No. | R[5] | Physical properties |
|---|---|---|
| 21 | $CH_3O(CH_2)_2OCO-$ | m), 7.50 (2m, t-like), 7.64 (1H, t, J=7.4Hz), 8.11 (2H, d, J=7.7Hz) m.p.: not lower than 97° C. FAB-MS (m/z): 1145 (MH+) IR (nujol)$\nu_{max}$ (cm$^{-1}$) : 3400, 1750, 1720 $^1$H-NM (CDCl$_3$) δ: 1.11 (3H, s), 1.21 (3H, s), 1.24 (3H, t, J=7.2Hz), 1.6 to 1.7 (2H, m), 1.76 (3H, s), 1.8 to 1.9 (1H, m), 1.90 (3H, s), 2.2 to 2.45 (2H, m), 2.36 (3H, s), 2.59 (1H, m), 2.92 (1H, dd, J=4.6, 17.1Hz), 3.13 (1H, dd, J=4.6, 17.1Hz), 3.28 (3H, s), 3.3 to 3.5 (2H, m), 3.89 (1H, d, J=7.3Hz), 3.93 to 4.33 (8H, m), 4.63 (2H, s), 4.67 (1H, m), 4.94 (1H, m), 5.12 (2H, s), 5.18 (1H, s), 5.51 (1H, m), 5.52 (1H, br s), 5.67 (1H, d, J=7.3Hz), 5.99 (2H, m), 6.22 (1H, m), 7.27 to 7.4 (10H, m), 7.5 (2H, m), 7.6 (1H, m), 8.13 (2H, m) |

TABLE 9

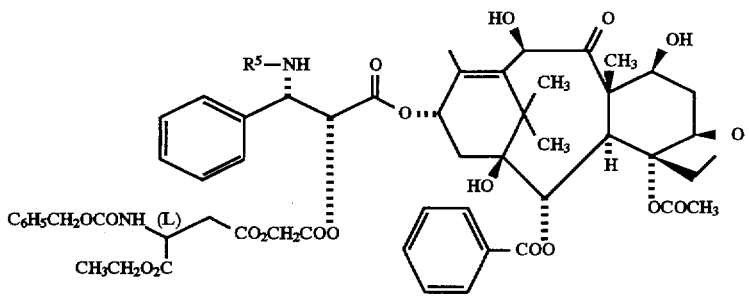

| Example No. | R[5] | Physical properties |
|---|---|---|
| 22 | cyclobutyl-CH$_2$-OCO— | m.p.: 117 to 120° C. FAB-MS (m/z) : 1155 (MH+) IR (nujol)$\nu_{max}$(cm$^{-1}$) ; 3440, 3360, 1750, 1730 $^1$H-NMR (CDCl$_3$) δ: 1.11 (3H, s), 1.21 (3H, s), 1.25 (3H, t, J=7.1Hz), 1.5 to 1.9 (10H, m), 1.75 (3H, s), 1.91 (3H, s), 2.1 to 2.3 (2H, m), 2.35 (3H, s), 2.6 (1H, m), 2.99 (1H, dd, J=5, 17Hz), 3.12 (1H, dd, J=5, 17Hz), 3.9 to 4.0 (3H, m), 4.15 to 4.3 (6H, m), 4.6 to 4.7 (3H, m), 4.95 (1H, m), 5.12 (2H, s), 5.20 (1H, s), 5.48 (1H, m), 5.67 (1H, d, J=7.0Hz), 5.8 to 6.0 (3H, m), 6.22 (1H, m), 7.35 (10H, m), 7.51 (2H, m), 7.62 (1H, m), 8.11 (2H, m) |

TABLE 9-continued

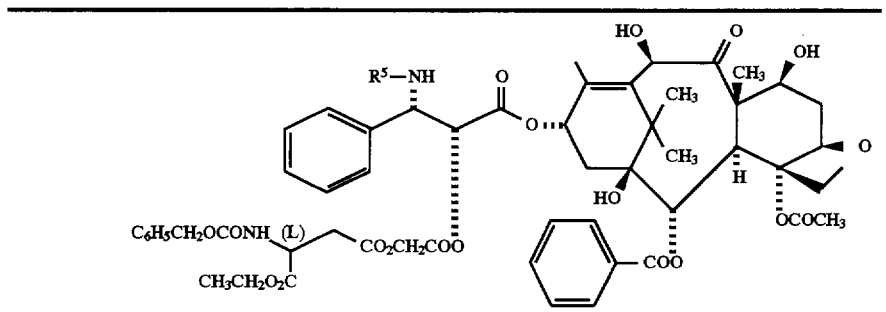

| Example No. | R[5] | Physical properties |
|---|---|---|
| 23 | ▱-CH2-OCO— | m.p.: 128 to 135° C.<br>FAB-MS (m/z): 1141 (MH+)<br>IR (nujol)υ_{max}(cm^{-1}): 3360, 1720<br>$^1$H-NMR (CDCl$_3$) δ: 0.04 to 0.17 (2H, m), 0.34 to 0.49 (2H, m), 0.93 to 1.05 (1H, m), 1.11 (3H, s), 2.20 (3H, s), 1.24 (3H, t, J=7.0Hz), 1.58 (1H, m), 1.66 (1H, s), 1.75 (3H, s), 1.91 (3H, s), 1.98 to 2.12 (1H, m), 2.18 to 2.45 (2H, m), 2.36 (3H, s), 2.54 to 2.68 (1H, m), 2.93 (1H, dd, J=4, 17Hz), 3.13 (1H, dd, J=4, 17Hz), 3.68 to 3.83 (2H, m), 3.90 (1H, d, J=7Hz), 4.14 to 4.33 (6H, m), 4.63 to 4.72 (3h, m), 4.94 (1H, d, J = 8.0Hz), 5.12 (2H, s), 5.16 (1H, s), 5.51 (2H, br s), 5.66 (1H, d, J=7Hz), 5.89 (1H, br), 5.94 to 6.00 (1H, m), 6.18 to 6.29 (1H, m), 7.27 to 7.42 (10H, m), 7.46 to 7.54 (2H, m), 7.57 to 7.65 (1H, m), 8.08 to 8.14 (2H, m) |

TABLE 10

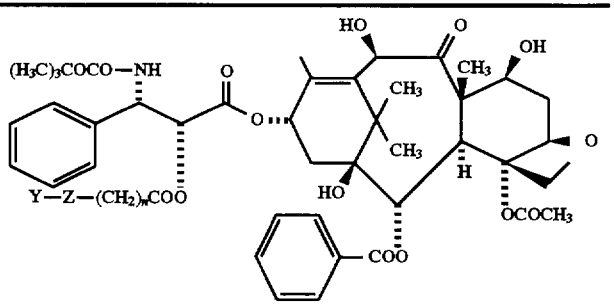

| Example No. | Y—Z—(CH$_2$)$_n$COO— |
|---|---|
| 24 | C$_6$H$_5$CH$_2$OCONH–CH(CONH$_2$)–COOCH$_2$COO— (L) |
| 25 | C$_6$H$_5$CH$_2$OCONH–CH(L)(CH$_3$)–CO—NH–CH$_2$CH$_2$–COO— |

TABLE 11A

[Structure: taxane core with (H₃C)₃COCO—NH, X substituent, Y—O—CH₂COO group, and standard baccatin substituents HO, OH, CH₃, CH₃, CH₃, OH, OCOCH₃, H, C₆H₅COO]

| Example No. | X | Y |
|---|---|---|
| 26 | 2,4-difluorophenyl | C₆H₅CH₂OCONH—CH(L)(COOCH₂CH₃)—CH₂—CO— |
| 27 | 3-fluorophenyl | C₆H₅CH₂OCONH—CH(L)(COOCH₂CH₃)—CH₂—CO— |
| 28 | 4-fluorophenyl | C₆H₅CH₂OCONH—CH(L)(COOCH₂CH₃)—CH₂—CO— |
| 29 | 2-methoxyphenyl | C₆H₅CH₂OCONH—CH(L)(COOCH₂CH₃)—CH₂—CO— |
| 30 | 4-methoxyphenyl | C₆H₅CH₂OCONH—CH(L)(COOCH₂CH₃)—CH₂—CO— |
| 31 | 2,4-difluorophenyl | C₆H₅CH₂OCONH—CH(L)(COOCH₂CH₂OCH₃)—CH₂—CO— |

TABLE 11B

| Example No. | Physical properties |
|---|---|
| 26 | FAB-MS (m/z): 1179 (MH⁺)<br>IR (nujol) $v_{max}$ (cm⁻¹): 3440, 3360, 1750, 1720<br>¹H-NMR (CDCl₃) δ: 1.12(3H, s), 1.21(3H, s), 1.26.(3H, t, J=7Hz), 1.32(9H, s), 1.60(1H, s), 1.68(1H, s), 1.75(3H, s), 1.85(1H, m), 1.91(3H, s), 2.05(1H, m) 2.17(1H, m), 2.38(3H, s), 2.61(1H, m), 2.94(1H, m), 3.13(1H, m), 3.91(1H, d, J=7Hz), 4.20(1H, s), 4.2 to 4.3(5H, m), 4.62(2H, s), 4.68(1H, m), 4.96(1H, d, J=8Hz), 5.12(2H, s), 5.19(1H, s), 5.47(1H, m), 5.68(1H, d, J=7Hz), 5.72(1H, br), 5.76(1H, m), 5.95(1H, br), 6.22(1H, m), 6.85(1H, m), 6.93(1H, m), 7.32(1H, m), 7.35(5H, m), 7.50(2H, m), 7.61(1H, m), 8.11(2H, m) |
| 28 | FAB-MS (m/z): 1161 (MH⁺)<br>IR (nujol) $v_{max}$ (cm⁻¹): 3440 to 3360, 1745, 1705<br>¹H-NMR (300MHz, CDCl₃) δ: 1.12(3H, s), 1.21(3H, s), 1.25(3H, t, J=7Hz), 1.33(9H, s), 1.67(2H, s, D₂O exchange), 1.75(3H, s), 1.85(1H, m), 1.91(3H, s-like), 2.1 to 2.4(2H, m), 2.34(3H, s), 2.6(1H, m), 2.9(1H, m), 3.1(1H, m), 3.9(1H, d, J=7Hz), 4.15 to 4.3(6H, m), 4.6 to 4.7(3H, m), 4.95(1H, m), 5.12(2H, s), 5.20(1H, br s), 5.46(1H, m), 5.47(1H, br), 5.57(1H, br), 5.68(1H, d, J=7Hz), 5.92(1H, br), 6.22(1H, m), 7.0 to 7.4(9H, m), 7.50(2H, m), 7.61(1H, m), 8.10(2H, m) |
| 31 | FAB-MS (m/z): 1209 (MH⁺)<br>IR (nujol) $v_{max}$ (cm⁻¹): 3360, 1750, 1720<br>¹H-NMR (CDCl₃) δ: 1.12(3H, s), 1.21(3H, s), 1.33(9H, s), 1.59(1H, s), 1.67(1H, s), 1.75(3H, s), 1.85(1H, m), 1.92(3H, s), 2.15(1H, m), 2.28(1H, m), 2.33(3H, s), 2.64(1H, m), 2.96(1H, m), 3.17(1H, m), 3.33(3H, s), 3.57(2H, m), 3.89(1H, d, J=7Hz), 4.16(1H, m), 4.21(1H, s), 4.30(4H, m), 4.59(1H, d, J=16Hz), 4.66(1H, d, J=16Hz), 4.74(1H, m), 4.96(1H, d, J=9Hz), 5.11(2H, s), 5.19(1H, s), 5.49(1H, m), 5.67(1H, d, J=7Hz), 5.70(2H, m), 6.04(1H, br d), 6.20(1H, m), 6.83(1H, m), |

TABLE 11B-continued

| Example No. | Physical properties |
|---|---|
| | 6.91(1H, m), 7.32(1H, m), 7.35(5H, m), 7.51(2H, m), 7.62(1H, m), 8.10(2H, m) |

Example 32

0.15 g of 10% palladium-carbon (containing 50% of water) and 14 μl of methanesulfonic acid were added to a solution of 205 mg of 4α-acetoxy-13α-{(2R,3S)-3-tert-butoxycarbonylamino-2-[((3S)-3-benzyloxycarbonylamino-3-ethoxycarbonylpropionyloxy)acetoxy]-3-phenylpropionyloxy}-2α-benzoyloxy-5β,20epoxy-1β,7β,10β-trihydroxytax-11-en-9-one dissolved in 15 ml of tetrahydrofuran, and the mixture was stirred under atmospheric pressure of hydrogen for 2 hours. The catalyst was removed by filtration, the filtrate was concentrated under reduced pressure, and diethyl ether was added to the residue.

Crystals precipitated were collected by filtration, washed with a diethyl ether-ethyl acetate mixed solution and then diethyl ether and dried to obtain 172 mg of 4α-acetoxy-13α-{(2R,3S)-3-tert-butoxycarbonylamino-2-[((3S)-3-amino-3-ethoxycarbonylpropionyloxy)acetoxy]-3-phenylpropionyloxy}-2α-benzoyloxy-5β,20-epoxy-1β,7β,10β-trihydroxytax-11-en-9-one.methanesulfonate.

Solubility: 5 mg/ml (physiological saline)

m.p.: 165° to 170° C. (decomposed)

FAB-MS (m/z): 1009 (MH$^+$)

IR (nujol) $v_{max}$ (cm$^{-1}$): 3400, 1750, 1720

$^1$H-NMR (DMSO-d$_6$) δ: 0.98 (6H, s), 1.23 (3H, t, J=7.1 Hz), 1.38 (9H, s), 1.51 (3H, s), 1.69 (3H, s), 2.20 to 2.34 (4H, m), 2.22 (3H, s), 2.30 (3H, s), 3.01 (1H, dd, J=5.5, 17.6 Hz), 3.09 (1H, dd, J=5.5, 17.6 Hz), 3.62 (1H, d, J=7.0 Hz), 3.97 to 4.07 (3H, m), 4.17 to 4.28 (3H, m), 4.40 (1H, d, J=5.5 Hz), 4.43 (1H, d, J=7.8 Hz), 4.78 to 5.13 (6H, m), 5.17 (1H, d, J=7.4 Hz), 5.40 (1H, d, J=7.0 Hz), 5.79 (1H, t, J=10 Hz), 7.18 (1H, br t), 7.35 to 7.44 (5H, m), 7.64 to 7.75 (2H, m), 7.90 (1H, d, J=8.6 Hz), 7.99 (2H, d, J=7.1 Hz), 8.44 (3H, br s)

Examples 33 to 57

By processing corresponding starting compounds in the same manner as in Example 32, the compounds shown in Tables 12 to 20 were obtained. In the tables, solubility means a solubility in physiological saline.

TABLE 12

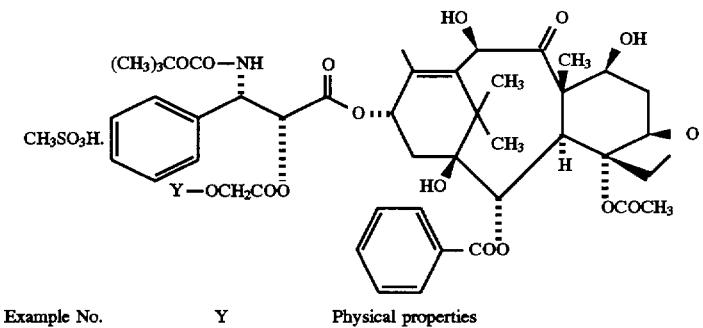

| Example No. | Y | Physical properties |
|---|---|---|
| 33 | —CO—(L)—N(pyrrolidine)H | Solubility: 1.4 mg/ml<br>m.p.: 163 to 176° C. (decomposed)<br>FAB-MS (m/z) : 963 (MH$^+$)<br>IR (nujol)$v_{max}$(cm$^{-1}$) : 3400, 1760, 1720<br>$^1$H-NMR (DMSO-d$_6$) δ: 0.98 (6H, s), 1.38 (9H, s), 1.52 (3H, s), 1.68 (3H, s), 1.88 to 2.42 (8H, m), 2.21 (3H, s), 2.31 (3H, s), 3.18 to 3.45 (2H, m), 3.61 (1H, d, J = 7.2Hz), 3.97 to 4.07 (1H, m), 4.01 (1H, br s), 4.01 (1H, d, J = 7.2Hz), 4.05 (1H, d, J = 7.2Hz), 4.40 to 4.48 (1H, m), 4.53 to 4.62 (1H, m), 4.87 to 4.99 (2H, m), 4.89 (1H, d, J = 8.1Hz), 5.06 (2H, br s), 5.12 (1H, s), 5.19 (1H, d, J = 7Hz), 5.40 (1H, d, T = 7.2Hz), 5.72 to 5.84 (1H, m), 7.18 (1H, t, J = 7Hz), 7.32 to 7.47 (5H, m), 7.62 to 7.78 (3H, m), 7.99 (2H, d, J = 7.0Hz), 9.00 (1H, br s), 9.50 (1H, br s) |

TABLE 12-continued

[Structure: taxane core with (CH3)3COCO—NH, phenyl, Y—OCH2COO substituents, CH3SO3H salt; labels include HO, OH, CH3, O, OCOCH3, COO-phenyl]

| Example No. | Y | Physical properties |
|---|---|---|
| 34 | —COCH₂NHCOCH₂NH₂ | Solubility: 10 mg/ml<br>m.p.: 159 to 161° C.<br>FAB-MS (m/z): 1002 (M⁺+Na), 980 (MH⁺)<br>IR (nujol)Σ_max(cm⁻¹): 3400, 1760, 1710<br>¹H-NMR (DMSO-d₆) δ: 0.98 (6H, s), 1.38 (9H, s), 1.51 (3H, s), 1.68 (3H, s), 1.6 to 1.9 (3H, m), 2.22 (3H, s), 2.22 (1H, m), 2.30 (3H, s), 3.5 to 3.7 (3H, m), 3.9 to 4.1 (4H, m), 4.11 (2H, d, J = 5.8Hz), 4.44 (1H, br s), 4.86 (1H, d, J = 16.6Hz), 4.92 (1H, d, J = 16.6Hz), 4.7 to 5.0 (2H, m), 5.07 (1H, s), 5.08 (1H, m), 5.16 (1H, d, J = 7.5Hz), 5.40 (1H, d, J = 7.0Hz), 5.78 (1H, m), 7.1 to 8.1 (14H, m), 8.85 (1H, t, J = 5.8Hz) |

TABLE 13

[Structure: taxane core with (CH3)3COCO—NH, phenyl, Y—OCH2COO substituents, CH3SO3H salt; labels include HO, OH, CH3, O, OCOCH3, COO-phenyl]

| Example No. | Y | Physical properties |
|---|---|---|
| 35 | —CO—CH₂—CH(L)(NH₂)—CO₂(CH₂)₂OCH₃ | Solubility: 10 mg/ml<br>m.p.: 153 to 155° C. (decomposed)<br>FAB-MS (m/z): 1039 (MH⁺)<br>IR (nujol)υ_max(cm⁻¹): 3420, 1755, 1715<br>¹H-NMR (DMSO-d₆) δ: 0.98 (6H, s), 1.37 (9H, s), 1.51 (1H, m), 1.51 (3H, s), 1.66 (1H, m), 1.69 (3H, s), 1.81 (1H, m), 2.23 (3H, s), 2.25 (1H, m), 2.30 (3H, s), 3.01 (1H, dd, J = 6, 18Hz), 3.09 (1H, dd, J = 6, 18Hz), 3.26 (3H, s), 3.56 (2H, t-like), 3.62 (1H, d, J = 7Hz), 4.02 (3H, m), 4.29 (2H, m), 4.44 (2H, m), 4.8 to 4.9 (3H, m), 4.94 (1H, d-like), 4.99 (1H, d-like), 5.07 (1H, s), 5.09 (1H, m), 5.17 (1h, d, J = 7Hz), 5.40 (1H, d, J = 7Hz), 5.79 (1H, t-like), 7.18 (1H, t-like), 7.40 (4H, m), 7.65 (2H, t-like), 7.73 (1H, t-like), 7.98 (2H, d, J = 7Hz), 7.90 (1H, d, J = 9Hz), 8.43 (3H, br s) |

TABLE 13-continued
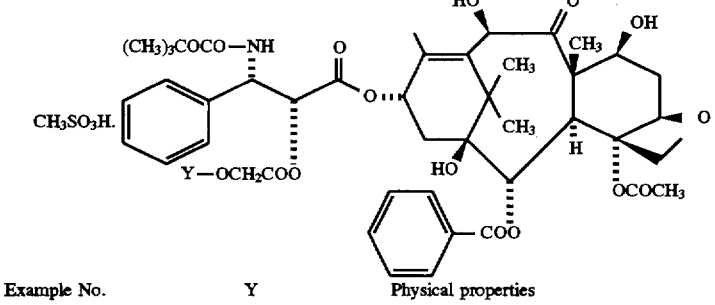
| Example No. | Y | Physical properties |
|---|---|---|
| 36 | —CO(L)C(CH₃)(NH₂)— | Solubility: 2 mg/ml<br>m.p.: 168 to 170° C.<br>FAB-MS (m/z): 937 (MH⁺)<br>IR (nujol)$\upsilon_{max}$ (cm⁻¹): 3420, 1760, 1710<br>¹H-NMR (DMSO-d₆) δ: 0.98 (6H, s), 1.38 (9H, s), 1.45 (3H, d, J=7.2Hz), 1.51 (3H, s), 1.69 (3H, s), 1.4 to 1.9 (3H, m), 2.21 (3H, s), 2.27 (1H, m), 2.32 (3H, s), 3.61 (1H, d, J=7.0Hz), 3.9 to 4.1 (3H, m), 4.26 (1H, br s), 4.44 (1H, br s), 4.75 (1H, q, J=7.2Hz), 4.89 (1H, d, J=9.1Hz), 4.94 (1H, m), 5.06 (2H, s), 5.08 (1H, m), 5.10 (1H, s), 5.17 (1H, d, J=7.5Hz), 5.39 (1H, d, J=7.0Hz), 5.79 (1H, d, J=9Hz), 7.1 to 8.0 (11H, m), 8.40 (3H, br s) |

TABLE 14
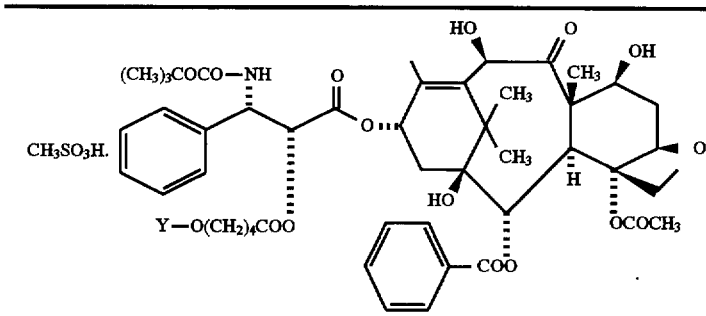
| Example No. | Y | Physical properties |
|---|---|---|
| 37 | —CO—O—CH₂—CH(NH₂)(L)—CO₂CH₂CH₃ | Solubility: 1 mg/ml<br>m.p.: not lower than 148° C. (slowly decomposed)<br>FAB-MS (m/z); 1051 (MH⁺)<br>IR (nujol)υ$_{max}$(cm$^{-1}$) : 3400, 1745, 1720<br>$^1$H-NMR (DMSO-$d_6$) δ: 0.97 (6H, s), 1.22 (3H, t, J = 7Hz), 1.37 (9H, s), 1.51 (3H, s), 1.60 (4H, m), 1.66 (1H, m), 1.70 (3H, s), 1.80 (1H, m), 2.24 (3H, s), 2.25 (1H, m), 2.30 (3H, s), 2.45 (1H, m), 2.89 (1H, dd, J = 6, 17Hz), 2.99 (1H, dd, J = 6, 17Hz), 3.63 (1H, d, J = 7Hz), 4.0 to 4.1 (7H, m), 4.21 (2H, q, J = 7Hz), 4.37 (1H, t, J = 6Hz), 4.42 (1H, s), 4.90 (1H, d, J = 10Hz), 5.0 to 5.1 (5H, m), 5.40 (1H, d, J = 7Hz), 5.77 (1H, t-like), 7.17 (1H, m), 7.37 (2H, m), 7.42 (2H, t-like), 7.66 (2H, t-like), 7.74 (1H, t-like), 7.86 (1H, d, J = 9Hz), 7.98 (2H, d-like), 8.42 (3H, br s) |

TABLE 15

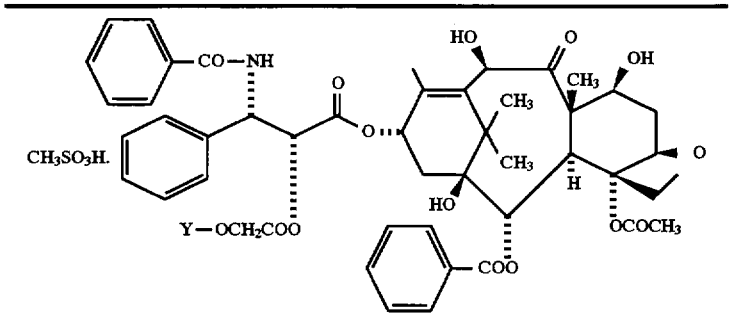

| Example No. | Y | Physical properties |
|---|---|---|
| 38 | —CO⌒⌒NH₂ | Solubility: 1 mg/ml<br>m.p.: 136 to 140° C. (decomposed)<br>FAB-MS (m/z) : 941 (MH⁺)<br>IR (nujol)υ$_{max}$(cm⁻¹) : 3420, 3260, 1750, 1730<br>1H-NMR (DMSO-d₆) δ: 0.98 (6H, s), 1.51 (3H, s), 1.68 (3H, s), 1.5 to 1.8 (3H, m), 2.22 (3H, s), 2.31 (3H, s), 2.73 (2H, m), 2.98 (2H, m), 3.60 (1H, d, J = 7.0Hz), 3.98 (1H, d, J = 8.3Hz), 4.03) (1H, d, J = 8.3Hz), 4.45 (1H, br s), 4.8 to 5.0 (4H, m), 5.06 (1H, s), 5.38 (1H, d, J = 7.0Hz), 5.42 (1H, d, J = 9.1Hz), 5.52.(1H, dd, J = 8.5, 9.1Hz), 5.80 (1H, m), 7.1 to 8.1 (18H, m), 9.26 (1H, d, J = 8.5Hz) |
| 39 | —CO⌒(L)⌒NH₂<br>CO₂CH₂CH₃ | m.p.; 133 to 137° C. (decomposed)<br>FAB-MS (m/z): 1013 (MH⁺)<br>IR (nujol)υ$_{max}$(cm⁻¹) : 3420, 1750, 1720<br>¹H-NMR (DMSO-d₆) δ: 0.96 (6H, m), 1.21 (3H, m), 1.51 (3H, s), 1.69 (6H, m), 1.9 (1H, br m), 2.2 (1H, m), 2.21 (3H, s), 2.25 (1H, br m), 2.31 (3H, s), 3.0 (2H, m), 3.60 (1H, m), 4.02 (2H, m), 4.21 (3H, m), 4.37 (1H, m), 4.89 (3H, m), 4.98 (1H, m), 5.06 (1H, s-like), 5.32 (1H, m), 5.40 (1H, m), 5.52 (1H, m), 5.80 (1H, m), 8.1 to 8.7 (15H, m), 8.45 (3H, br s), 9.26 (1H, d-like) |

TABLE 16

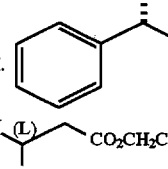

| Example No. | R[5] | Physical properties |
|---|---|---|
| 40 | 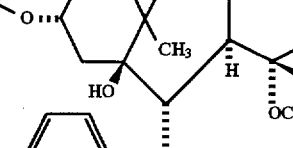 | Solubility: 6 mg/ml<br>m.p.: 142 to 146° C.<br>FAB-MS (m/z): 1003 (MH[+])<br>IR (nujol)$\upsilon_{max}$ (cm[-1]): 3400, 1760<br>$^1$H-NMR (DMSO-$d_6$) δ: 0.96 (6H, s), 1.24 (3H, t, J = 7Hz), 1.50 (3H, 3), 1.60 to 1.72 (1H, m), 1.67 (3H, s), 2.03 to 2.21 (3H, m), 2.20 (3H, s), 2.29 (3H, s), 2.90 to 3.10 (2H, m), 3.59 (1H, d, J = 7Hz), 3.94 to 4.03 (m, 3H), 4.17 to 4.34 (2H, m), 4.34 to 4.45 (2H, m), 4.81 to 5.00 (5H, m), 5.05 (1H, s), 5.28 to 5.48 (3H, m), 5.71 to 5.81 (1H, m), 6.67 (1H, dd, J = 1.6, 3.5Hz), 7.10 to 7.99 (22H, m), 8.45 (3H, br s), 9.30 (1H, br d, J = 8.1Hz) |
| 41 |  | Solubility: 0.7 mg/ml<br>m.p.: 148 to 152° C. (decomposed)<br>FAB-MS (m/z): 1019 (MH[+])<br>IR (nujol)$\upsilon_{max}$ (cm[-1]): 3440, 1750<br>$^1$H-NMR (DMSO-$d_6$) δ: 0.98 (6H, br s), 1.14 to 1.28 (3H, s), 1.51 (3H, s), 1.59 to 1.79 (1H, m), 1.69 (3H, s), 2.10 to 2.31 (3H, m), 2.19 (3H, s), 2.30 (3H, s), 2.90 to 3.10 (2H, m), 3.60 (1H, d, J = 7Hz), 3.97 to 4.07 (2H, m), 4.14 to 4.26 (3H, m), 4.33 to 4.41 (1H, m), 4.63 (1H, s), 4.83 to 5.03 (4H, m), 5.06 (1H, s), 5.34 to 5.52 (3H, m), 5.76 to 5.83 (1H, m), 7.16 to 7.97 (13H, m), 8.43 (3H, br s), 9.20 (1H br d, J = 8.2Hz) |

TABLE 17

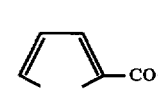

| Example No. | R[5] | Physical properties |
|---|---|---|
| 42 | CL(CH$_2$)$_4$CO— | Solubility: 5 mg/ml<br>m.p: not lower than 128° C. (slowly decomposed)<br>FAB-MS (m/z): 1027 (MH[+])<br>IR (nujol)$\upsilon_{max}$ (cm[-1]) : 3420, 1750<br>$^1$H-NMR (DMSO-$d_6$) δ: 0.98 (3H, s), 0.99 (3H, |

TABLE 17-continued

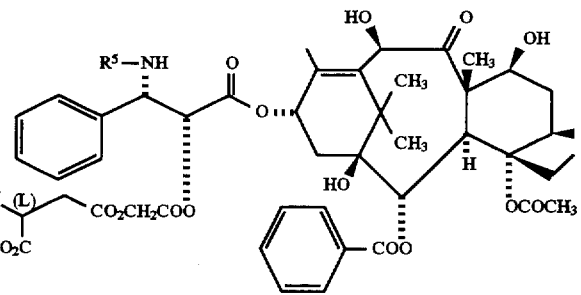

| Example No. | R[5] | Physical properties |
|---|---|---|
| | | s), 1.23 (3H, t, J = 7Hz), 1.51 (3H, s), 1.66 (4H, m), 1.71 (3H, s), 1.8 to 2.3 (6H, m), 2.24 (3H, s), 2.31 (3H, s), 2.9 to 3.1 (2H, m), 3.59 (2H, m), 3.64 (1H, d, J = 7Hz), 4.03 (3H, m), 4.21 (3H, m), 4.40 (2H, br s), 4.5 (1H, br 5), 4.89 (1H, d-like), 4.82 (1H, d, J = 16Hz), 4.91 (2H, d, J = 16Hz), 5.08 (1H, s), 5.28 (1H, d-like), 5.41 (1H, d, J = 7Hz), 5.48 (1H, t-like), 5.85 (1H, t-like), 7.2 to 7.5 (5H, m), 7.64 (2H, t-like), 7.72 (2H, t-like), 8.00 (2H, d-like), 8.44 (3H, br s), 8.76 (1H, d, J = 9Hz) |
| 43 | 2,5-dimethoxybenzoyl (OCH$_3$, OCH$_3$ substituted benzoyl – CO—) | Solubility: 0.5 mg/ml<br>m.p.: 144 to 147° C.<br>FAB-MS (m/z) : 1073 (MH$^+$)<br>IR (nujol)υ$_{max}$(cm$^{-1}$) : 3360, 1760<br>$^1$H-NMR (DMSO-d$_6$) δ: 0.98 (3H, s), 1.00 (3H, s), 1.21 (3H, t, J = 7Hz), 1.53 (3H, s), 1.62 to 1.72 (1H, m), 1.73 (3H, s), 1.97 to 2.07 (1H, m), 2.21 to 2.34 (2H, m), 2.28 (3H, s), 2.30 (3H, s), 2.98 (1H, dd, J = 5.6, 17.8Hz), 3.07 (1H, dd, J = 5.6, 17.8Hz), 3.64 (3H, s), 3.68 (1H, d, J = 7.0Hz), 3.87 (3H, s), 3.95 to 4.10 (3H, m), 4.16 to 4.26 (2H, m), 4.34 to 4.41 (1H, m), 4.56 (1H, s), 4.84 (1H, d, J = 16.4Hz), 4.93 (1H, d, J = 16.4Hz), 4.85 to 5.01 (3H, m), 5.08 (1H, s), 5.42 (1H, d, J = 7.0Hz), 5.51 (1H, d, J = 6.3Hz), 5.70 (1H, dd, J = 6.3, 8.9Hz), 5.92 (1H, t-like), 7.04 to 7.71 (11H, m), 8.02 (2H, d, J = 7.1Hz), 8.34 (3H, br s), 9.04 (1H, d, J = 8.9Hz) |

TABLE 18

| Example No. | R[5] | Physical properties |
|---|---|---|
| 44 | CH$_3$CH$_2$OCO— | Solubility: 4 mg/ml<br>m.p.: 157 to 159° C.<br>FAB-MS (m/z): 981 (MH$^+$)<br>IR (nujol)υ$_{max}$ (cm$^{-1}$): 3420, 1750, 1720<br>$^1$H-NMR (DMSO-d$_6$) δ: 0.98 (6H, s), 1.15 3H, t, J = 7Hz), 1.23 (3H, t, J = 7Hz), 1.5 (1Hm), 1.51 (3H, s), 1.65 (1H, m), 1.69 (3H, s), 1.80 (1H, m), 2.23 (3H, s), 2.25 |

TABLE 18-continued

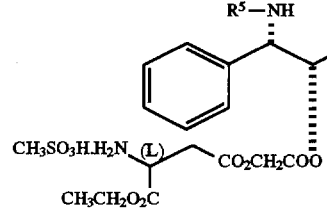

| Example No. | R⁵ | Physical properties |
|---|---|---|
| | | (1H, m), 2.30 (3H, s), 3.01 (1H, dd, J = 6, 18Hz), 3.09 (1H, dd, J = 6, 18Hz), 3.62 (1H, d, J = 7Hz), 4.00 (5H, m), 4.21 (2H, q, J = 7Hz), 4.41 (1H, m), 4.46 (1H, s), 4.9 to 5.0 (5H, m), 5.06 (1H, s), 5.11 (1H, m), 524 (1H, d, J = 8Hz), 5.40 (1H, d, J = 7Hz), 5.81 (1H, t-like), 7.18 (1H, m), 7.37 (2H, m), 7.43 (2H, m), 7.65 (2H, t-like), 7.73 (1H, t-like), 7.99 (2H, d, J = 7Hz), 8.21 (1H, d, J = 9Hz), 8.45 (3H, br s) |
| 45 | 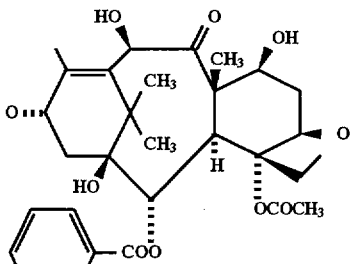 | Solubility: 0.6 mg/ml<br>m.p.: 142 to 146° C. (decomposed)<br>FAB-MS (m/z): 1071 (MH⁺)<br>IR (nujol)υ$_{max}$(cm⁻¹): 3400, 1760, 1720<br>¹H-NMR (DMSO-d₆) δ: 0.98 (6H, s), 1.05 to 1.20 (6H, m), 1.23 (3H, t, J = 7.1Hz), 1.40 to 1.55 (1H, m), 1.52 (3H, s), 1.61 to 1.68 (2H, m), 1.70 (3H, s), 1.75 to 1.90 (1H, m), 2.20 to 2.30 (1H, m), 2.25 (3H, d, J = 2.6Hz), 2.31 (3H, s), 3.01 (2H, dd, J = 56 17.4Hz), 3.10 (1H, dd, J = 5.6, 17.4Hz), 3.62 (1H, d, J = 6.9Hz), 3.93 to 4.18 (5H, m), 4.22 (2H, q, J = 7.0Hz), 4.36 to 4.47 (2H, m), 4.78 to 5.00 (5H, m), 5.06 (1H, s), 5.12 (1H, br q), 5.27 (1H, d, J = 7.9Hz), 5.40 (1H, d, J = 7.6Hz), 5.81 (1H, br t), 7.15 to 7.23 (1H, m), 7.34 to 7.47 (4H, m), 7.61 to 7.76 (3H, m), 7.99 (2H, d, 7.6Hz), 8.40 (1H, d, J = 9.2Hz), 8.46 (3H, br s) |

TABLE 19

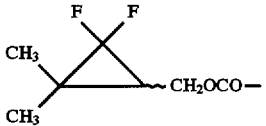

| Example No. | R⁵ | Physical properties |
|---|---|---|
| 46 | CF₃CH₂OCO— | Solubility: 5 mg/ml<br>138 to 142° C. (decomposed)<br>FAB-MS (m/z) : 1035 (MH⁺)<br>IR (nujol)υ$_{max}$ (cm⁻¹): 3440, 1750<br>¹H-NMR (DMSO-d₆) δ: 0.97 (6H, s), 1.23 (3H, t, J = 7Hz), 1.35 to 1.44 (1H, m), 1.51 (3H, s), 1.68 (3H, s), 1.60 to 1.83 (2H, m), 2.17 to 2.28 (1H, m), 2.22 (3H, s), |

TABLE 19-continued

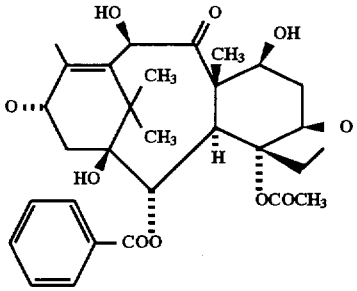

| Example No. | $R^5$ | Physical properties |
|---|---|---|
| | | 2.30 (3H, s), 3.01 (1H, dd, J = 5.6, 17.7Hz), 3.09 (1H, dd, J = 5.6, 17.7Hz), 3.61 (1H, d, J = 7.0Hz), 3.97 to 4.07 (3H, m), 4.17 to 4.28 (2H, m), 4.41 (1H, t, J = 5.4Hz), 4.45 (1H, s), 4.67 (2H, q, J = 9.1Hz), 4.81 to 5.11 (7H, m), 5.27 (1H, d, J = 7.9Hz), 5.39 (1H, d, J = 7.0Hz), 5.79 (1H, d, J = 9Hz), 7.19 (1H, t, J = 7.4Hz), 7.33 to 7.48 (4H, m), 7.66 (2H, t-like), 7.74 (1H, t, J = 7Hz), 7.98 (2H, d, J = 7Hz) 8.44 (3H, br s), 8.81 (1H, d, J = 9.1Hz) |
| 47 | $CH_3O(CH_2)_2OCO-$ | Solubility: >10 mg/ml<br>130 to 134° C. (decomposed)<br>FAB-MS (m/z) : 1011 (MH$^+$)<br>IF (nujol)$\upsilon_{max}$ (cm$^{-1}$) : 3400, 1750,<br>$^1$H-NMR (DMSO-d$_6$) δ: 0.98 (3H, s), 1.23 (3H, t, J = 7.0Hz), 1.43 (1H, m), 1.51 (3H, s), 1.65 (1H, m), 1.68 (3H, s), 1.79 (1H, m), 2.21 (1H, m), 2.22 (3H, s), 2.30 (3H, s), 3.01 (1H, dd, J = 5.4, 17.5Hz), 3.1 (1H, dd, J = 5.4, 17.5Hz), 3.24 (3H, s), 3.44 (2H, m), 3.61 (1H, d, J = 7.1Hz), 3.9 to 4.2 (5H, m), 4.22 (2H, q, J = 7.0Hz), 4,22 (1H, m), 4.41 (1H, br s), 4.43 (1H, m), 4.8 to 5.0 (4H, m), 5.06 (1H, s), 5.09 (1H, dd, J = 7.7, 9.1Hz), 5.23 (1H, d, J = 7.7Hz), 5.39 (1H, d, J = 7.1Hz), 5.79 (1H, m), 7.1 to 8.0 (10H, m), 8.36 (1H, d, J = 9.1Hz), 8.43 (3H, br s) |

TABLE 20

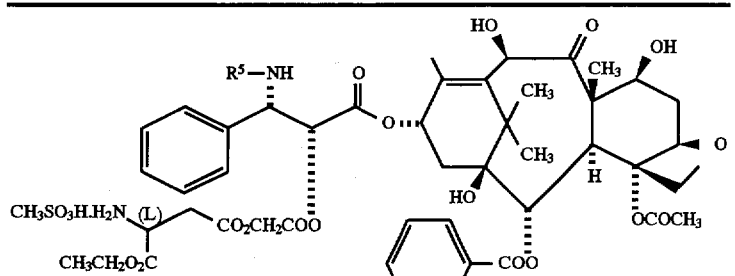

| Example No. | R⁵ | Physical properties |
|---|---|---|
| 48 | cyclobutyl-CH₂-OCO— | Solubility: 1 mg/ml<br>m.p.: 128 to 131° C. (decomposed)<br>FAB-MS (m/z); 1021 (MH⁺)<br>IR (nujol)$\upsilon_{max}$(cm⁻¹) : 3400, 1750, 1720<br>¹H-NMR (DMSO-d₆) δ: 0.97 (6H, s), 1.09 (3H, t, J = 7.0Hz), 1.51 (3H, s), 1.69 (3H, s), 1.1 to 2.0 (9H, m), 2.24 (3H, s), 2.26 (1H, m), 2.30 (3H, s), 2.52 (2H, m), 3.03 (2H, m), 3.62 (1H, d, J = 7.3Hz), 3.94 (2H, m), 3.99 (1H, d, J = 9.0Hz), 4.01 (1H, d, J = 9.0Hz), 4.20 (1H, m), 4.22 (2H, q, J = 7.0Hz), 4.43 (1H, m), 4.45 (1H, br s), 4.64 (1H, s), 4.82 (1H, d, J = 16Hz), 4.89 (1H, d, J = 9Hz), 4.91 (1H, d, J = 16Hz), 4.98 (1H, br s), 5.06 (1H, s), 5.11 (1H, dd, J = 7.7, 9.3Hz), 5.25 (1H, dd, J = 7.7, Hz), 5.40 (1H, d, J = 7.3Hz), 5.80 (1H, m), 7.2 to 8.0 (10H, m), 8.25 (1H, d, J = 9.3Hz), 8.44 (3H, br s) |
| 49 | cyclopropyl-CH₂-OCO— | Solubility: 5 mg/ml<br>m.p.: 147 to 151° C.<br>FAB-MS (m/z): 1007 (MH⁺)<br>IR (nujol)$\upsilon_{max}$(cm⁻¹) : 3400, 1750, 1720<br>¹H-NMR (DMSO-d₆) δ; 0. 17 to 0.26 (2H, m) 0.43 to 0.53 (2H, m), 0.98 (6H, s), 1.0 to 1.10 (1H, m), 1.17 (3H, t, J = 7.1Hz), 1.41 to 1.52 (1H, m), 1.51 (3H, s), 1.61 to 1.70 (1H, m), 1.69 (3H, s), 1.76 to 1.86 (1H, m), 2.19 to 2.34 (1H, m), 2.24 (3H, s), 2.30 (3H, s), 3.01 (1H, dd, J = 5.7, 17.6Hz), 3.09 (1H, dd, J = 5.7, 17.6Hz), 3.6 (1H, d, J = 6.9Hz), 3.79 (2H, d, J = 5.2Hz), 3.97 to 4.07 (4H, m), 4.17 to 4.29 2H, m), 4.40 (1H, t, J = 5.7Hz), 4.44 (1H, s), 4.81 to 5.12 (7H, m), 5.23 (1H, d, J = 7.5Hz), 5.40 (1H, d, J = 6.9Hz), 5.81 (1H, t-like), 7.18 (1H, t, J = 7.5.Hz), 7.33 to 7.45 (4H, m), 7.65 (2H, t, J = 7.5Hz), 7.73 (1H, t, J = 7.0Hz), 7.99 (2H, t, J = 7.9Hz), 8.28 (1H, d, J = 9.4Hz), 8.43 (3H, br s) |

TABLE 21
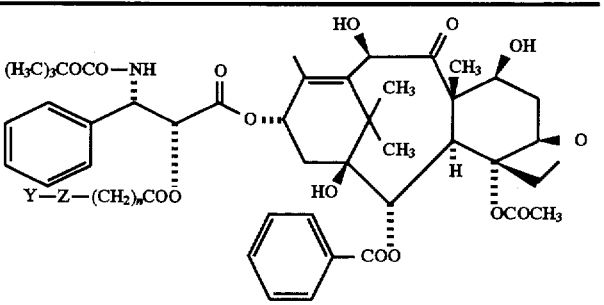
| Example No. | Y—Z—(CH₂)ₙCOO— |
|---|---|
| 50 |  |
| 51 | 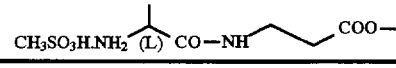 |
TABLE 22A
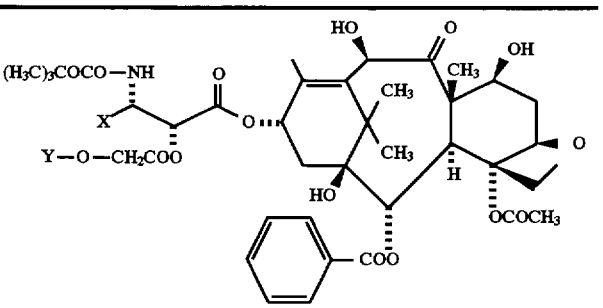
| Example No. | X | Y |
|---|---|---|
| 52 | 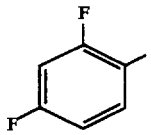 | 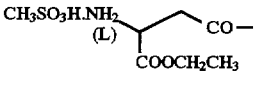 |
| 53 | 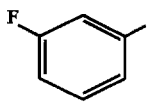 | 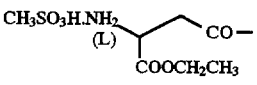 |
| 54 | 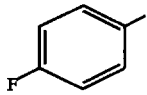 | 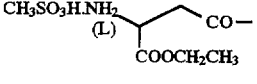 |
| 55 | 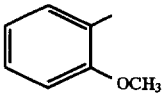 | 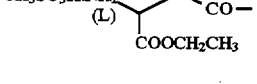 |
| 56 | 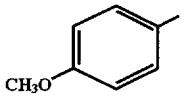 | 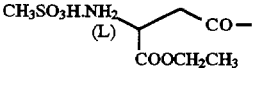 |

TABLE 22A-continued

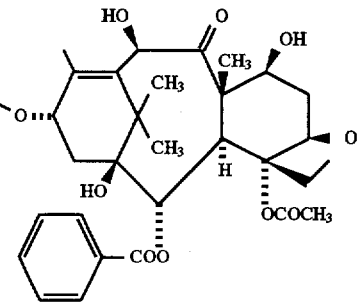

| Example No. | X | Y |
|---|---|---|
| 57 | (2,4-difluorophenyl) | CH₃SO₃H.NH₂ (L) -CH(-)-CH₂-CO- / COOCH₂CH₂OCH₃ |

TABLE 22B

| Example No. | Physical properties |
|---|---|
| 52 | Solubility: 1 mg/ml<br>m.p.: not lower than 157° C. (decomposed)<br>FAB-MS (m/z): 1045 (MH⁺)<br>IR (nujol)ν_max (cm⁻¹): 3420, 1760, 1720<br>¹H-NMR (DMSO-d₆) δ: 1.01(3H, s), 1.03(3H, s), 1.21 (3H, t, J=7Hz), 1.36(9H, s), 1.53(3H, s), 1.67(1H, m), 1.74(3H, s), 1.94(1H, m), 2.08(1H, m), 2.27(1H, m), 2.23(3H, s), 2.31(3H, s), 3.01(1H, dd, J=5, 17Hz), 3.09(1H, dd, J=5, 17Hz), 3.69(1H, d, J=7Hz), 4.04(3H, m), 4.20(2H, q, J=7Hz), 4.39(1H, m), 4.64 (1H, s), 4.79(1H, d, J=16Hz), 4.90(1H, d, J=16Hz), 4.92(1H, d, J=9Hz), 4.98(1H, br s), 5.02(1H, br), 5.11(1H, s), 5.16(1H, d, J=6Hz), 5.45(1H, d, J=7Hz), 5.53(1H, dd, J=6, 10Hz), 5.89(1H, m), 7.22(1H, m), 7.28(1H, m), 7.60(2H, m), 7.70(2H, m), 8.00(3H, m), 8.44(3H, br s) |
| 54 | m.p.: 161.5 to 164.5° C. (decomposed)<br>FAB-MS (m/z): 1027 (MH⁺)<br>IR (nujol)ν_max (cm⁻¹): 3440 to 3400, 1750, 1710<br>¹H-NMR (400MHz, DMSO-d₆) δ: 1.02(6H, s), 1.25(3H, t, J=7Hz), 1.39(9H, s), 1.55(3H, s), 1.69(2H, m), 1.73 (3H, s), 1.95(1H, m), 2.3(1H, m), 2.27(3H, s), 2.33 (3H, s), 3.03(1H, dd, J=6, 18Hz), 3.11(1H, dd, J=5, 18Hz), 3.68(1H, d, J=7Hz), 4.05(3H, m), 4.24(2H, m), 4.42(1H, m), 4.52(1H, s), 4.8 to 5.0(5H, m), 5.11 (1H, s), 5.17(1H, m), 5.24(1H, d, J=2Hz), 5.45(1H, d, J=7Hz), 5.86(1H, m), 7.26(2H, m), 7.45(2H, m), 7.91(1H, d, J=10Hz), 7.62(2H, m), 7.73(1H, m), 8.00 (2H, m), 8.43(3H, br s) |
| 56 | Solubility: 15 mg/ml<br>m.p.: 173 to 176° C. (decomposed)<br>FAB-MS (m/z): 1039 (M+H)<br>IR (nujol)ν_max (cm⁻¹): 3400, 1750, 1710<br>¹H-NMR (DMSO-d₆) δ: 1.00(6H, s), 1.09, 1.22 (each, 3H, t, J=7.0Hz), 1.36(9H, s), 1.52(3H, s), 1.6 to 1.8 (2H, m), 1.71(3H, s), 1.9 to 2.0(1H, m), 2.2 to 2.3 (1H, m), 2.28(3H, s), 2.31(2H, s), 3.01(1H, dd, J= 5.5, 17.7Hz), 3.09(1H, dd, J=5.5, 17.7Hz), 3.50(3H, s), 3.67(1H, d, J=7.1Hz), 4.0 to 4.1(3H, m), 4.22, 4.23(each, 2H, q, J=7.0Hz), 4.39(1H, br s), 4.40(1H, t, J=5.5Hz), 4.81(1H, d, J=16.5Hz), 4.91(1H, d, J= 16.5Hz), 4.92(1H, d, J=9Hz), 5.00(1H, m), 5.09(1H, s), 5.11(1H, m), 5.16(1H, d, J=6.7Hz), 5.43(1H, d, J=7.1Hz), 5.80(1H,m), 6.9 to 8.0(10H, m), 8.43(3H, br s) |
| 57 | Solubility: 5 mg/ml |

| Example No. | Physical properties |
|---|---|
| | m.p.: not lower than 157° C. (decomposed)<br>FAB-MS (m/z): 1075 (MH⁺)<br>IR (nujol)ν_max (cm⁻¹): 3400, 1760, 1720<br>¹H-NMR (DMSO-d₆) δ: 1.01(3H, s), 1.03(3H, s), 1.36 (9H, s), 1.53(3H, s), 1.67(1H, m), 1.74(3H, s), 1.94 (1H, m), 2.09(1H, m), 2.23(3H, s), 2.27(1H, m), 2.30 (3H, s), 3.00(1H, dd, J=6, 17Hz), 3.08(1H, dd, J=6, 17Hz), 3.25(3H, s), 3.55(2H, m), 3.69(1H, d, J=7Hz), 4.04 (3H, m), 4.28(2H, m), 4.43(1H, m), 4.64(1H, s), 4.78(1H, d, J=16Hz), 4.90(1H, d, J=16Hz), 4.96(1H, m), 5.01(2H, m), 5.11(1H, s), 5.16 (1H, d, J=6Hz), 5.54(1H, d, J=7Hz), 5.54(1H, m), 5.89(1H, m), 7.22 (1H, m), 7.28(1H, m), 7.60(2H, m), 7.70(2H, m), 8.00 (3H, m), 8.45(3H, br s) |

Example 58

186 mg of (3S)-3-benzyloxycarbonylamino-3-ethoxycarbonylpropionyloxyacetic acid and 127 mg of N,N'-dicyclohexylcarbodiimide were added to a solution of 0.15 g of taxol (=4α,10β-diacetoxy-13α-[(2R,3S)-3-benzoylamino-2-hydroxy-3-phenylpropionyloxy]-2α-benzoyloxy-5β,20-epoxy-1β,7β-dihydroxytax-11-en-9-one) dissolved in 8 ml of dichloromethane, and the mixture was stirred at room temperature for 26 hours. Insolubles were removed by filtration, and the filtrate was concentrated under reduced pressure. The residue was purified by silica gel column chromatography (solvent; hexane:ethyl acetate:dichloromethane=2:4:1) to obtain 209 mg of 4α,10β-diacetoxy-13α-{(2R,3S)-3-benzoylamino-2-[((3S)-3-benzyloxycarbonylamino-3-ethoxycarbonylpropionyloxy)acetoxy]-3-phenylpropionyloxy}-2α-benzoyloxy-5β,20-epoxy-1β,7β-dihydroxytax-11-en-9-one.

FAB-MS (m/z): 1189 (MH⁺)

IR (nujol) ν_max (cm⁻¹): 3320, 1750, 1720

¹H-NMR (CDCl₃) δ: 1.11 (3H, s), 1.20 (3H, s), 1.25 (3H, t, J=7 Hz), 1.59 (1H, S), 1.68 (3H, S), 1.71 (1H, s), 1.91 (3H, s), 1.93 to 2.05 (1H, m), 2.1 to 2.2 (1H, m), 2.23 (3H, s), 2.3 to 2.4 (1H, m), 2.43 (3H, s), 2.56 (1H, m), 2.90 (1H, m), 3.10

(1H, m), 3.80 (1H, d, J=7 Hz), 4.10 (1H, m), 4.12 (2H, q, J=7 Hz), 4.25 (2H, ABq, J=9 Hz), 4.45 (1H, m), 4.62 (1H, d, J=16 Hz), 4.67 (1H, d, J=16 Hz), 4.97 (1H, d, J=8 Hz), 5.0 to 5.1 (1H, m), 5.04 (2H, s), 5.64 (1H, d, J=3.5 Hz), 5.68 (1H, d, J=7.0 Hz), 5.90 (1H, t, J=8 Hz), 6.05 (1H, dd, J=3.5, 8 Hz), 6.25 (1H, t, J=8 Hz), 6.30 (1H, s), 7.2 to 7.6 (16H, m), 7.75 (2H, d, J=7 Hz), 8.15 (2H, d, J=7 Hz)

Example 59

195 mg of 4α,10β-diacetoxy-13α-{(2R,3S)-3-benzoylamino-2-[((3S)-3-benzyloxycarbonylamino-3-ethoxycarbonylpropionyloxy)acetoxy]-3-phenylpropionyloxy}-2α-benzoyloxy-5β,20-epoxy-1β,7β-dihydroxytax-11-en-9-one was processed in the same manner as in Example 32 to obtain 4α,10β-diacetoxy-13α-{(2R,3S)-3-benzoylamino-2-[((3S)-3-amino-3-ethoxycarbonylpropionyloxy)acetoxy]-3-phenylpropionyloxy}-2α-benzoyloxy-5β,20-epoxy-1β,7β-dihydroxytax-11-en-9-one.methanesulfonate.

Solubility: 0.3 mg/ml (physiological saline)

m.p.: 113° to 115° C. (decomposed)

FAB-MS (m/z): 1055 (MH$^+$)

$^1$H-NMR (DMSO-d$_6$) δ: 0.99 (3H, s), 1.02 (3H, s), 1.21 (3H, t, J=7 Hz), 1.59 (3H, s), 1.77 (3H, s), 1.59 to 1.79 (2H, m), 2.1 to 2.31 (2H, m), 2.11 (3H, s), 2.20 (3H, s), 2.30 (3H, s), 2.9 to 3.1 (2H, m), 3.55 (1H, d, J=7 Hz), 3.9 to 4.4 (6H, m), 4.82 to 4.86 (4H, m), 5.32 (1H, m), 5.40 (1H, d, J=7 Hz), 5.50 to 5.56 (1H, m), 5.8 (1H, m), 6.28 (1H, s), 7.2 to 8.0 (1H, m), 8.43 (3H, br s), 9.26 (1H, d, J=8.5 Hz)

Example 60

(1) Under argon atmosphere, a solution of (3S)-3-benzyloxycarbonylamino-3-ethoxycarbonylpropionyloxy) acetic acid (972 mg, 2.75 mmol) dissolved in tetrahydrofuran (10 ml) was cooled to −10° C. To the solution were added triethylamine (278 mg, 2.75 mmol) and isopropyl chlorocarbonate (337 mg, 2.75 mmol), and the mixture was stirred for 30 minutes. To the mixture was added dropwise a solution of 4α-acetoxy-2α-benzoyloxy-5β-20-epoxy-1β,7β,10β-trihydroxy-13α-[(2R,3S)-3-(4-fluorophenyl)-2-hydroxy-3-tert-butoxycarbonylaminopropionyloxy]-tax-11-ene-9-one (454 mg, 0.55 mmol) dissolved in tetrahydrofuran (10 ml), and the mixture was further stirred for 7 hours. After a saturated aqueous sodium hydrogen carbonate solution (20 ml) was added to the reaction mixture, the mixture was extracted with ethyl acetate. The organic layer was washed with water and brine and dried over anhydrous sodium sulfate. The solvent was removed, and the residue obtained was purified by silica gel flash column chromatography (ethyl acetate/hexane=2/1) to obtain 4α-acetoxy-2α-benzoyloxy-5β-20-epoxy-1β,7β,10β-trihydroxy-13α-[(2R,3S)-3-(4-fluorophenyl)-2-[((3S)-3-benzyloxycarbonylamino-3-ethoxycarbonylpropionyloxy)acetoxy]-3-tert-butoxycarbonylaminopropionyloxy]-tax-11-ene-9-one (544 mg, yield: 85%). The physical property values were the same as those of the compound obtained in Example 58.

(2) Methanesulfonic acid (32 μl, 0.49 mmol) and palladium-carbon (Pd—C) (250 mg) were added to a solution of 4α-acetoxy-2α-benzoyloxy-5β-20-epoxy-1β,7β,10β-trihydroxy-13α-[(2R,3S)-3-(4-fluorophenyl)-2-[(3S)-3-benzyloxycarbonylamino-3-ethoxycarbonylpropionyloxy)acetoxy]-3-tert-butoxycarbonylaminopropionyloxy]-tax-11-ene-9-one (520 mg, 0.448 mmol) dissolved in tetrahydrofuran (50 ml). The mixture was stirred under the atmospheric pressure at room temperature for 1 hour. After the catalyst was removed from the reaction mixture by filtration, the filtrate was concentrated. Diethyl ether was added to the concentrate, and the mixture was stirred for 30 minutes while cooling by an ice bath. Precipitates were collected by filtration using a glass filter and sufficiently washed with diethyl ether. The precipitates were dried under reduced pressure to obtain 4α-acetoxy-2α-benzoyloxy-5β-20-epoxy-1β,7β,10β-trihydroxy-13α-[(2R,3S)-3-(4-fluorophenyl)-2-[((3S)-3-amino-3-ethoxycarbonylpropionyloxy)acetoxy]-3-tert-butoxycarbonylaminopropionyloxy]-tax-11-ene-9-one-methanesulfonate (404 mg, yield: 80%).

Reference Example 1

(1) 78 mg of 1,4-bis(9-O-dihydroquinidyl)phthalazine was added to a solution of 9.88 g of potassium ferricyanide and 4.14 g of potassium carbonate dissolved in 100 ml of tert-butanol-water (1:1), and the mixture was stirred at room temperature for 30 minutes. The reaction mixture was adjusted to about pH 11 by adding phosphoric acid thereto. 0.05 ml of osmium tetraoxide (0.4M toluene solution) was added to the mixture, and the resulting mixture was stirred at room temperature for 30 minutes. After the mixture was cooled with ice bath, 1.98 g of methyl (2',4'-difluoro) cinnamate was added thereto, and the mixture was stirred at room temperature overnight. After the mixture was cooled with ice bath, to the reaction mixture was added 15 g of sodium sulfite, and then, the mixture was stirred at room temperature for 30 minutes. Thereafter, ethyl acetate was added to the mixture, and the organic layer was collected by separation. The solvent was removed under reduced pressure, and the residue was purified by silica gel column chromatography (solvent; hexane:ethyl acetate=1:1) and further recrystallized from dichloromethane-hexane to obtain 1.73 g of methyl (2S,3R)-3-(2,4-difluorophenyl)-2,3-dihydroxypropionate.

$[α]_D^{20}$=−10.0° (c=1, chloroform)

IR (nujol) ν$_{max}$ (cm$^{-1}$): 3440, 3360, 1750

MS (m/z): 232 (M$^+$)

$^1$H-NMR (CDCl$_3$) δ: 2.89 (1H, d, J=7.3 Hz), 3.22 (1H, d, J=5.9 Hz), 3.85 (3H, s), 4.35 (1H, dd, J=3.0, 5.9 Hz), 5.29 (1H, dd, J=3.0, 7.3 Hz), 6.81 (1H, m), 6.92 (1H, m), 7.52 (1H, m)

(2) Under argon atmosphere, a solution of 955 mg of methyl (2S,3R)-3-(2,4-difluorophenyl)-2,3-dihydroxypropionate dissolved in 30 ml of dichloromethane was cooled to 0° C., and to the solution was added 940 mg of p-toluenesulfonyl chloride and 624 mg of triethylamine. After the mixture was stirred at 0° C. for 3 days, the reaction mixture was washed with water and dried, and the solvent was removed. The residue was purified by silica gel column chromatography (solvent; hexane:ethyl acetate=2:1) to obtain 1.15 g of methyl (2S,3R)-3-(2,4-difluorophenyl)-3-hydroxy-2-(p-toluenesulfonyloxy)propionate.

IR (nujol) ν$_{max}$ (cm$^{-1}$): 3500, 1745

FAB-MS (m/z): 409 (M$^+$+Na)

$^1$H-NMR (CDCl$_3$) δ: 2.43 (3H, s), 2.75 (1H, d, J=7 Hz), 3.76 (3H, s), 5.00 (1H, d, J=3 Hz), 5.41 (1H, dd, J=3, 7 Hz), 6.57 (1H, m), 6.79 (1H, m), 7.20 (2H, m), 7.37 (1H, m), 7.53 (2H, m)

(3) 0.26 ml of water and 1.20 g of potassium carbonate were added to a solution of 1.12 g of methyl (2S,3R)-3-(2,4-difluorophenyl)-3-hydroxy-2-(p-toluenesulfonyloxy) propionate dissolved in 15 ml of dimethylformamide, and the mixture was stirred at room temperature overnight. Ethyl acetate and ice water were added to the reaction mixture, and the organic layer was collected by separation. After the organic layer was washed with water and dried, the solvent was removed. The residue was purified by silica gel column chromatography (solvent; hexane:ethyl acetate=10:1) to obtain 502 mg of methyl (2R,3R)-3-(2,4-difluorophenyl)-2-epoxypropionate.

IR (nujol) $v_{max}$ (cm$^{-1}$): 1760, 1740

FAB-MS (m/z): 237 (M$^+$+Na)

$^1$H-NMR (CDCl$_3$) δ: 3.60 (3H, s), 3.87 (1H, dd, J=4.4 Hz), 4.36 (!H, d, J=4.4 Hz), 6.80 (1H, m), 6.88 (1H, m), 7.48 (1H, m)

(4) Under argon atmosphere, 1 ml of methyl formate and 360 mg of sodium azide were added to a solution of 237 mg of methyl (2R,3R)-3-(2,4-difluorophenyl)-2-epoxypropionate dissolved in 9 ml of methanol-water (8:1), and the mixture was stirred at 50° C. for 43 hours. After the reaction mixture was cooled, ethyl acetate and ice water were added to the reaction mixture, and the organic layer was collected by separation. After the organic layer was washed with water and dried, the solvent was removed. The residue was purified by silica gel column chromatography (solvent; hexane:ethyl acetate=5:1) to obtain 274 mg of methyl (2R,3S)-3-(2,4-difluorophenyl)-3-azido-2-hydroxypropionate.

IR (nujol) $v_{max}$ (cm$^{-1}$): 3480, 2120, 1750

FAB-MS (m/z): 258 (MH$^+$)

$^1$H-NMR (CDCl$_3$) δ: 3.15 (1H, d, J=6.7 Hz), 3.89 (3H, s), 4.38 (1H, dd, J=2.7, 6.7 Hz), 5.22 (1H, d, J=2.7 Hz), 6.87 (1H, m), 6.96 (1H, m), 7.65 (1H, m)

(5) 529 mg of di-tert-butyl bicarbonate and 200 mg of 10% palladium-carbon were added to a solution of 519 mg of methyl (2R,3S)-3-(2,4-difluorophenyl)-3-azido-2-hydroxypropionate dissolved in 20 ml of ethyl acetate, and the mixture was stirred under hydrogen atmosphere (1 atmospheric pressure) at room temperature for 9 hours. The catalyst was removed by filtration, and the filtrate was concentrated under reduced pressure. The residue was purified by silica gel column chromatography (solvent; hexane:ethyl acetate=4:1) to obtain 594 mg of methyl (2R,3S)-3-(2,4-difluorophenyl)-3-tert-butoxycarbonylamino-2-hydroxypropionate.

$[α]_D^{20}$=−13.59° (c=1, chloroform)

IR (nujol) $v_{max}$ (cm$^{-1}$): 3500, 3380, 1740, 1680

FAB-MS (m/z): 334 (MH$^+$)

$^1$H-NMR (CDCl$_3$) δ: 1.41 (9H, s), 3.16 (1H, d, J=4.2 Hz), 3.86 (3H, s), 4.42 (1H, br), 5.39 (1H, br), 5.48 (1H, br), 6.8 to 6.9 (2H, m), 7.33 (1H, m)

(6) 0.3 ml of isopropenyl methyl ether and 39 mg of pyridinium p-toluenesulfonate were added to a solution of 515 mg of methyl (2R,3S)-3-(2,4-difluorophenyl)-3-tert-butoxycarbonylamino-2-hydroxypropionate dissolved in 30 ml of benzene, and the mixture was stirred at room temperature for 30 minutes. The mixture was further stirred at 90° C. for 30 minutes and then returned to room temperature. 0.3 ml of isopropenyl methyl ether was added to the mixture, and the resulting mixture was stirred at 90° C. for 30 minutes. The mixture was cooled again to room temperature, 0.15 ml of isopropenyl methyl ether was added thereto, and the mixture was stirred at 90° C. for 4 hours. The reaction mixture was concentrated under reduced pressure, and the residue was purified by silica gel column chromatography (solvent; toluene:ethyl acetate=50:1) to obtain 428 mg of methyl (4S,5R)-3-tert-butoxycarbonyl-2, 2-dimethyl-4-(2,4-difluorophenyl)-5-oxazolidinecarboxylate.

IR (nujol) $v_{max}$ (cm$^{-1}$): 1760, 1740, 1700

FAB-MS (m/z): 394 (M$^+$+Na)

$^1$H-NMR (CDCl$_3$) δ: 1.19 (9H, br s), 1.69 (3H, s), 1.76 (3H, s), 3.80 (3H, s), 4.47 (1H, d, J=6 Hz), 5.36 (1H, br), 6.82 (1H, m), 6.90 (1H, m), 7.30 (1H, m)

(7) Under ice cooling, a solution of 31 mg of lithium hydroxide dissolved in 5 ml of water was added dropwise to a solution of 402 mg of methyl (4S,5R)-3-tert-butoxycarbonyl-2,2-dimethyl-4-(2,4-difluorophenyl)-5-oxazolidinecarboxylate dissolved in 10 ml of methanol. After the mixture was stirred at room temperature for 45 minutes, the reaction mixture was concentrated under reduced pressure. Water and diethyl ether were added to the residue, and the aqueous layer was collected by separation. The aqueous layer was adjusted to about pH 2 by adding 10% aqueous hydrochloric acid thereto under ice cooling and then extracted with chloroform. After the chloroform layer was washed with water and dried, the solvent was removed to obtain 385 mg of (4S,5R)-3-tert-butoxycarbonyl-2,2-dimethyl-4-(2,4-difluorophenyl)-5-oxazolidinecarboxylic acid.

IR (neat) $v_{max}$ (cm$^{-1}$): 3200 to 2980, 1740, 1700, 1680

FAB-MS (m/z): 380 (M$^+$+Na)

$^1$H-NMR (CDCl$_3$) δ: 1.21 (9H, br s), 1.72 (3H, s), 1.78 (3H, s), 4.53 (1H, d, J=5.9 Hz), 4.7 (1H, br), 5.37 (1H, br), 6.82 (1H, m), 6.91 (1H, m), 7.31 1H, m)

Reference Example 2

In the same manner as in Reference example 1, the carboxylic acid compounds described in Table 23 shown below were obtained.

TABLE 23

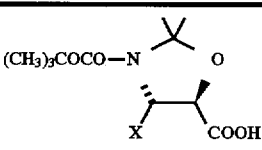

| No. | X |
| --- | --- |
| a | 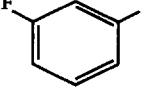 |
| b | 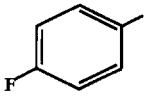 |
| c | 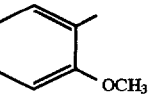 |
| d | 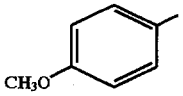 |

Reference Example 3

(1) A solution of 0.36 g of (4S,5R)-3-tert-butoxycarbonyl-2,2-dimethyl-4-(2,4-difluorophenyl)-5- oxazolidinecarboxylic acid, 0.572 g of 4α-acetoxy-2α-benzoyloxy-5,β20-epoxy-1β,13α-dihydroxy-7β,10β-bis(2,2,2-trichloroethoxycarbonyloxy)tax-11-en-9-one, 0.211 g of N,N-dicyclohexylcarbodiimide and 0.039 g of 4-dimethylaminopyridine dissolved in 20 ml of toluene was stirred under argon atmosphere at 80° C. for 2.5 hours. After the reaction mixture was cooled, precipitates were removed by filtration, and the filtrate was concentrated under reduced pressure. The residue was purified by silica gel column chromatography (solvent; hexane:ethyl acetate=4:1) to obtain 0.721 g of 4α-acetoxy-2α-benzoyloxy-13α-[4S,5R)-3-tert-butoxycarbonyl-2,2-dimethyl-4-(2,4-difluorophenyl)oxazolidin-5-ylcarbonyloxy)-5β,20-epoxy-1β-hydroxy-7β,10β-bis(2,2,2-trichloroethoxycarbonyloxy)tax-11-en-9-one.

FAB-MS (m/z): 1234 (MH$^+$+2)

(2) A solution of 0.694 g of 4α-acetoxy-2α-benzoyloxy-13α-[4S,5R)-3-tert-butoxycarbonyl-2,2-dimethyl-4-(2,4-difluorophenyl)oxazolidin-5-ylcarbonyloxy]-5β,20-epoxy-1β-hydroxy-7β,10β-bis(2,2,2-trichloroethoxycarbonyloxy)tax-11-en-9-one dissolved in 15 ml of formic acid was stirred at room temperature for 18 hours. Formic acid was removed, and small amount of ethanol and diisopropyl ether were added to the residue. Precipitate was collected by filtration and dried to obtain 0.526 g of 4α-acetoxy-2α-benzoyloxy-13α-[(2R,3S)-3-amino-3-(2,4-difluorophenyl)-2-hydroxypropionyloxy]-5β,20-epoxy-1β-hydroxy-7β,10β-bis(2,2,2-trichloroethoxycarbonyloxy)tax-11-en-9-one.formate.

FAB-MS (m/z): 1094 (MH$^+$+2)

(3) 0.116 g of sodium hydrogen carbonate was added to a solution of 0.526 g of 4α-acetoxy-2α-benzoyloxy-13α-[(2R,3S)-3-amino-3-(2,4-difluorophenyl)-2-hydroxypropionyloxy]-5β,20-epoxy-1β-hydroxy-7β,10β-bis(2,2,2-trichloroethoxycarbonyloxy)tax-11-en-9-one.formate dissolved in 12 ml of tetrahydrofuran, and then a solution of 0.201 g of di-tert-butyl bicarbonate dissolved in 3 ml of tetrahydrofuran was added dropwise to the mixture under ice cooling. Then, the resulting mixture was stirred at room temperature for 18 hours. Insolubles were removed by filtration, the filtrate was concentrated under reduced pressure, and the residue was dissolved in ethyl acetate. After the ethyl acetate layer was washed with water and dried, the solvent is removed. The residue was purified by silica gel column chromatography (solvent; toluene:ethyl acetate=5:1) to obtain 0.288 g of 4α-acetoxy-2α-benzoyloxy-13α-[2R,3S)-3-tert-butoxycarbonylamino-3-(2,4-difluorophenyl)-2- hydroxypropionyloxy]-5β,20-epoxy-1β-hydroxy-7β,10β-bis( 2,2,2-trichloroethoxycarbonyloxy) tax-11-en-9-one.

FAB-MS (m/z): 1194 (MH$^+$+2)

(4) 0.71 g of zinc powder was added to a solution of 0.26 g of 4α-acetoxy-2α-benzoyloxy-13α-[2R,3S)-3-tert-butoxycarbonylamino-3-(2,4-difluorophenyl)-2-hydroxypropionyloxy]-5β,20-epoxy-1β-hydroxy-7β,10β-bis(2,2,2-trichloroethoxycarbonyloxy)tax-11-en-9-one dissolved in methanol-acetic acid (12 ml-3 ml), and the mixture was heated to 60° C. and stirred for 90 minutes. After the mixture was cooled, zinc was removed by filtration, and the filtrate was concentrated under reduced pressure. The residue was dissolved in ethyl acetate, washed with a 1% HCl aqueous solution, a saturated aqueous sodium hydrogen carbonate solution and brine and dried, and then the solvent was removed. The residue was purified by silica gel column chromatography (solvent; hexane:ethyl acetate=2:3) to obtain 0.091 g of 4α-acetoxy-2α-benzoyloxy-13α-[2R,3S)-3-tert-butoxycarbonylamino-3-(2,4-difluorophenyl)-2-hydroxypropionyloxy]-5β,20-epoxy-1β,7β,10β-trihydroxytax-11-en-9-one.

IR (nujol) $v_{max}$ (cm$^{-1}$): 3440, 1720, 1460, 1380, 1270, 1250, 1110

FAB-MS (m/z): 844 (MH$^+$)

$^1$H-NMR (CDCl$_3$) δ: 1.13 (3H, s), 1.26 (3H, s), 1.31 (9H, s), 1.60 (1H, s), 1.73 (1H, s), 1.76 (3H, s), 1.85 (1H, m), 1.93 (3H, s), 2.2 to 2.4 (2H, m), 2.43 (3H, s), 2.59 (1H, m), 3.38 (1H, br), 3.93 (1H, d, J=7 Hz), 4.20 (1H, d, J=8 Hz), 4.22 (2H, m), 4.33 (1H, d, J=7 Hz), 4.56 (1H, br), 4.96 (1H, d-like), 5.21 (1H, s), 5.39 (1H, d-like), 5.53 (1H, br d), 5.69 (1H, d, J=7 Hz), 6.29 (1H, t-like), 6.87 (1H, m), 6.93 (1H, m), 7.38 (1H, m), 7.50 (2H, t-like), 7.60 (1H, t-like), 8.12 (2H, d, J=7 Hz)

Reference Example 4

(1) In the same manner as in Reference example 3-(1), the compounds in Table 24 shown below were obtained from corresponding starting compounds.

TABLE 24

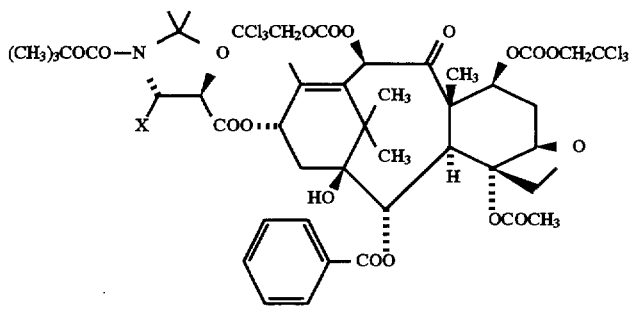

| No. | X |
|---|---|
| a | 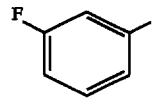 |

TABLE 24-continued
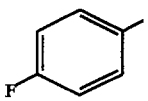
| No. | X |
|---|---|
| b | 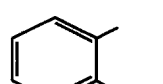 |
| c |  |
| d |  |
(2) In the same manner as in Reference example 3-(2), the compounds in Table 25 shown below were obtained from corresponding starting compounds.
TABLE 25
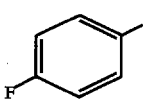
| No. | X |
|---|---|
| a | 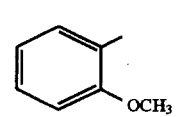 |
| b | 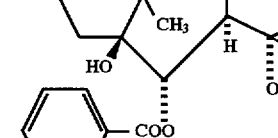 |
| c | 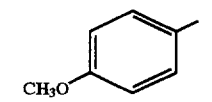 |
TABLE 25-continued
| No. | X |
|---|---|
| d | (4-CH₃O-C₆H₄-) |
(3) In the same manner as in Reference example 3-(3), the compounds in Table 26 shown below were obtained from corresponding starting compounds.

TABLE 26

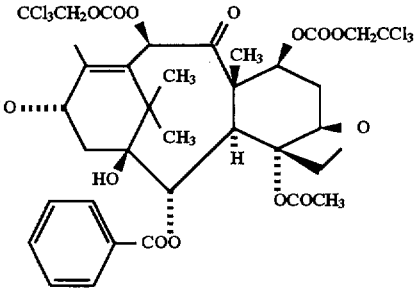

| No. | X |
|---|---|
| a | 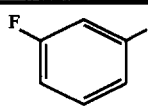 |
| b | 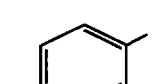 |
| c | 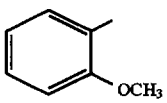 |
| d | 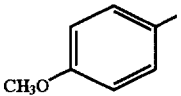 |

(4) In the same manner as in Reference example 3-(4), the compounds in Table 27 shown below were obtained from corresponding starting compounds.

TABLE 27

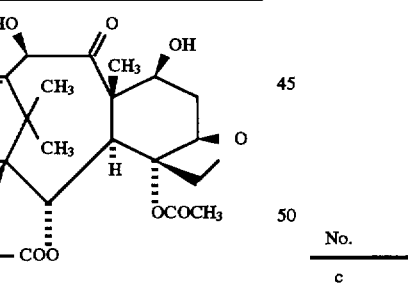

| No. | X |
|---|---|
| a |  |
| b |  |

TABLE 27-continued

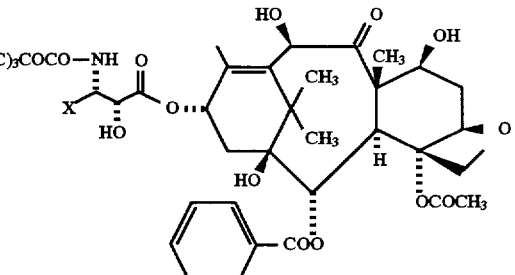

| No. | X |
|---|---|
| c | 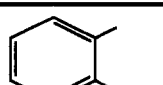 |
| d | 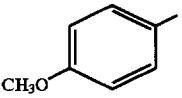 |

The process of the present invention is different from either of the methods which have been reported, i.e., the method in which a reaction time is long and N-benzoyl-3-phenylisoserine having protected hydroxyl group and giving a low yield is used (the above method (A)); the method using an azetidinone compound or an oxazolidine compound synthesis of which is complicated (the above methods (B) and (C)); and the method using osmium oxidation having no regioselectivity and giving a low yield (the above method (D)). The feature of the process of the present invention resides in that the 13α-(3-amino-2-hydroxypropionyloxy) baccatin derivative (VI) can be prepared efficiently by quantitatively introducing an epoxypropionyl group in which 3-position is substituted by an aryl group or the like into hydroxyl group at 13-position of the baccatin compound (II); cleaving by a metal azide, or cleaving and halogenating an oxirane ring of the resulting compound regioselectively and stereoselectively; and then substituting an azido group by a halogen atom regioselectively and stereoselectively; and then reducing an azido group.

The 13α-(3-amino-2-hydroxypropionyloxy)baccatin derivative (VI) obtained as described above is a synthetic intermediate of taxol, N-debenzoyl-N-(t-butoxycarbonyl)-10-deacetyltaxol or the like which is useful as an antitumor agent. By using the process described in the present specification, the taxol derivative (X) can be prepared efficiently.

Further, the 13α-(epoxypropionyloxy)baccatin compound (III), the 13α-(3-halogeno-2-hydroxypropionyloxy)baccatin compound (IV) and a 13α-(3-azido-2-hydroxypropionyloxy)baccatin compound (V) which are generated in the course of the process of the present invention are novel compounds and have important significance in asymmetric synthesis of the taxol, N-debenzoyl-N-(t-butoxycarbonyl)-10-deacetyltaxol or the like which is efficiently prepared by the present invention.

The desired compound (X) of the present invention or a pharmaceutically acceptable salt thereof has high water-solubility and high stability and also an excellent anti-tumor activity. For example, the taxol derivative of the present invention exhibits a significant antitumor activity and a significant life-prolongating effect on a mouse to which P-388 cells are transplanted intraperitoneally, a nude mouse to which human breast carcinoma MX-1 cells are transplanted subcutaneously or a mouse to which B16 melanoma cells are transplanted intraperitoneally or subcutaneously.

Further, the taxol derivative of the present invention or a pharmaceutically acceptable salt thereof has low toxicity and high water solubility. For example, When 4α-acetoxy-13α-{(2R,3S)-3-tert-butoxycarbonylamino-2-[((3S)-3-amino-3-ethoxycarbonylpropionyloxy)acetoxy]-3-phenylpropionyloxy}-2α-benzoyloxy-5β,20-epoxy-1β,7β,10β-trihydroxytax-11-en-9-one.methanesulfonate (solubility: 5 mg/ml) or 4α-acetoxy-13α-{(2R,3S)-3-tert-butoxycarbonylamino-2-[((3S)-3-amino-3-(2-methoxyethoxycarbonyl)propionyloxy)acetoxy]-3-phenylpropionyloxy}-2α-benzoyloxy-5β,20-epoxy-1β,7β,10β-trihydroxytax-11-en-9-one.methanesulfonate (solubility: 10 mg/ml) was intraperitoneally administered (25 mg/kg) to $BDF_1$ mice 4 times once a day and the mice were observed for 20 days, no case of death was observed.

Thus, the desired compound (X) of the present invention can be suitably used for medical treatment of a wide range of tumors such as breast carcinoma, ovary cancer, lung cancer and malignant melanoma.

We claim:
1. A process for preparing a 13α-(3-amino-2-hydroxypropionyloxy)baccatin compound represented by the formula (VI):

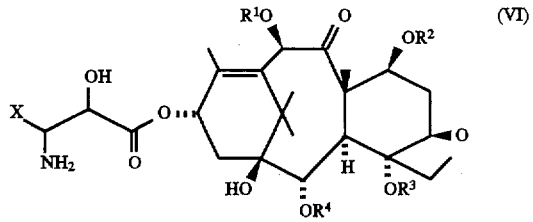

wherein $R^1$ represents a lower alkanoyl group or a protective group for hydroxy group; $R^2$ represents a protective group for hydroxy group; $R^3$ represents a lower alkanoyl group; $R^4$ represents a substituted or unsubstituted benzoyl group; and X represents a substituted or unsubstituted aryl group, a substituted or unsubstituted lower alkenyl group, or a substituted or unsubstituted lower alkynyl group, or a salt thereof, which comprises reducing a 13α-(3-azido-2-hydroxypropionyloxy)baccatin compound represented by the formula (V):

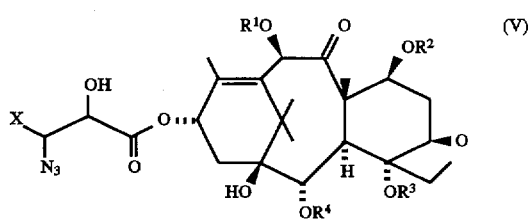

wherein $R^1$, $R^2$, $R^3$, $R^4$ and X have the same meanings as defined above, and, if necessary, converting the resulting compound to a salt thereof.

2. The process of claim 1, wherein said compound represented by the formula (V) is prepared by introducing an azido group to a 13α-epoxypropionyloxybaccatin compound represented by the formula (III):

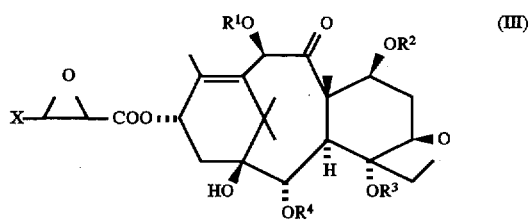

wherein $R^1$, $R^2$, $R^3$, $R^4$ and X have the same meanings as defined in claim 1.

3. The process of claim 2, wherein said compound represented by the formula (III) is prepared by condensing a baccatin compound represented by the formula (II):

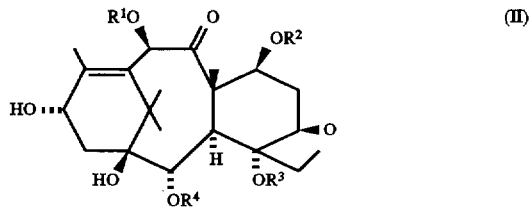

wherein $R^1$, $R^2$, $R^3$ and $R^4$ have the same meanings as defined in claim 2, and an epoxypropionic acid compound represented by the formula (I):

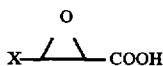
(I)

wherein X has the same meaning as defined in claim 1, or a reactive derivative thereof.

4. A process for preparing a 13α-(3-azido-2-hydroxypropionyloxy)baccatin compound represented by the formula (V):

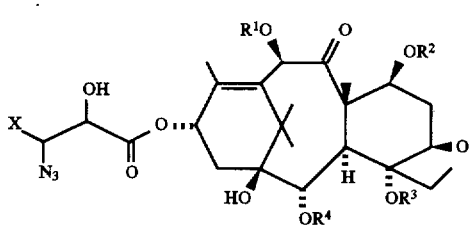
(V)

wherein $R^1$ represents a lower alkanoyl group or a protective group for hydroxy group; $R^2$ represents a protective group for hydroxy group; $R^3$ represents a lower alkanoyl group; $R^4$ represents a substituted or unsubstituted benzoyl group; and X represents a substituted or unsubstituted aryl group, a substituted or unsubstituted lower alkenyl group, or a substituted or unsubstituted lower alkynyl group, which comprises introducing an azido group to a 13α-epoxypropionyloxybaccatin compound represented by the formula (III):

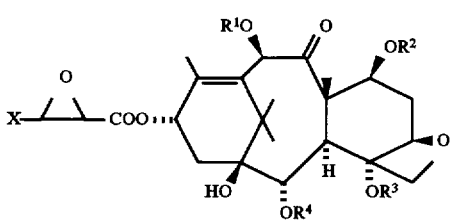
(III)

wherein $R^1$, $R^2$, $R^3$, $R^4$ and X have the same meanings as defined above.

5. The process of claim 4, wherein said compound represented by the formula (III) is prepared by condensing a baccatin compound represented by the formula (II):

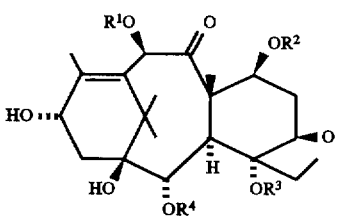
(II)

wherein $R^1$, $R^2$, $R^3$ and $R^4$ have the same meanings as defined in claim 4, and an epoxypropionic acid compound represented by the formula (I):

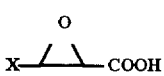
(I)

wherein X has the same meaning as defined in claim 4, or a reactive derivative thereof.

6. A process for preparing a 13α-(3-amino-2-hydroxypropionyloxy)baccatin compound represented by the formula (VI):

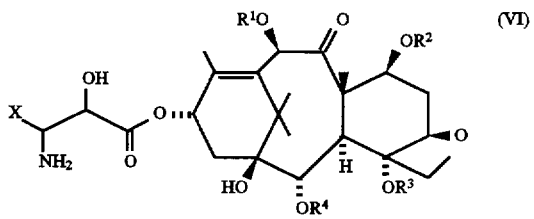
(VI)

wherein $R^1$ represents a lower alkanoyl group or a protective group for hydroxy group; $R^2$ represents a protective group for hydroxy group; $R^3$ represents a lower alkanoyl group; $R^4$ represents a substituted or unsubstituted benzoyl group; and X represents a substituted or unsubstituted aryl group, a substituted or unsubstituted lower alkenyl group, or a substituted or unsubstituted lower alkynyl group, or a salt thereof, which comprises introducing an azido group to a 13α-(3-halogeno-2-hydroxypropionyloxy)baccatin compound represented by the formula (IV):

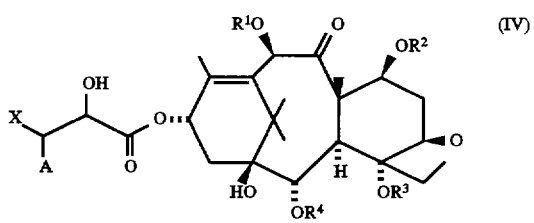
(IV)

wherein A represents a halogen atom; and $R^1$, $R^2$, $R^3$, $R^4$ and X have the same meanings as defined above, and reducing the resulting 13α-(3-azido-2-hydroxypropionyloxy)baccatin compound represented by the formula (V):

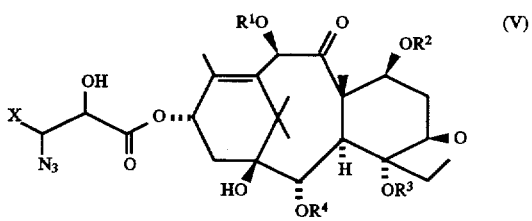
(V)

wherein $R^1$, $R^2$, $R^3$, $R^4$ and X have the same meanings as defined above, and, if necessary, converting the resulting compound to a salt thereof.

7. The process of claim 6, wherein said compound represented by the formula (IV) is prepared by halogenating a 13α-epoxypropionyloxybaccatin compound represented by the formula (III):

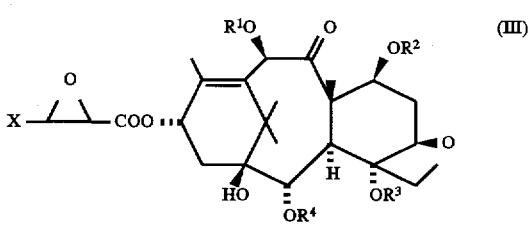
(III)

wherein $R^1$, $R^2$, $R^3$, $R^4$ and X have the same meanings as defined in claim 6.

8. The process of claim 7, wherein said compound represented by the formula (III) is prepared by condensing a baccatin compound represented by the formula (II):

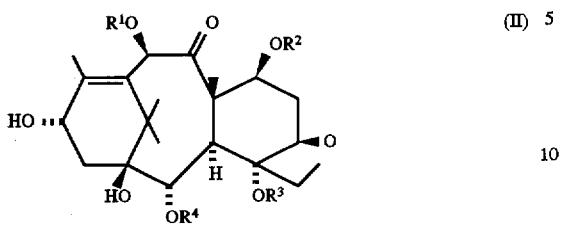

wherein $R^1$, $R^2$, $R^3$ and $R^4$ have the same meanings as defined in claim 7, and an epoxypropionic acid compound represented by the formula (I):

wherein X has the same meaning as defined in claim 7, or a reactive derivative thereof.

9. A process for preparing a 13α-(3-azido-2-hydroxypropionyloxy)baccatin compound represented by the formula (V):

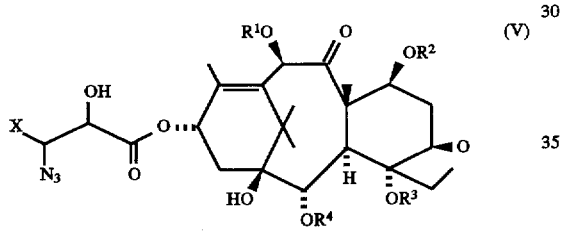

wherein $R^1$ represents a lower alkanoyl group or a protective group for hydroxy group; $R^2$ represents a protective group for hydroxy group; $R^3$ represents a lower alkanoyl group; $R^4$ represents a substituted or unsubstituted benzoyl group; and X represents a substituted or unsubstituted aryl group, a substituted or unsubstituted lower alkenyl group, or a substituted or unsubstituted lower alkynyl group, which comprises introducing an azido group to a 13α-(3-halogeno-2-hydroxypropionyloxy)baccatin compound represented by the formula (IV):

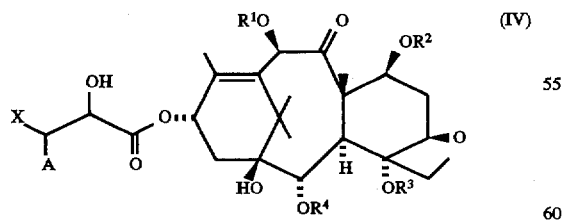

wherein A represents a halogen atom; and $R^1$, $R^2$, $R^3$, $R^4$ and X have the same meanings as defined above.

10. The process of claim 9, wherein said compound represented by the formula (IV) is prepared by halogenating a 13α-epoxypropionyloxybaccatin compound represented by the formula (III):

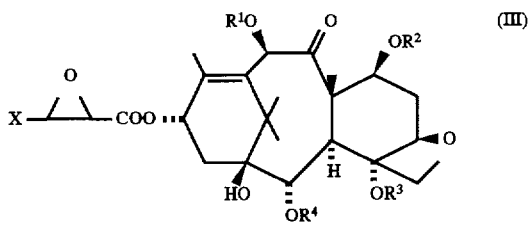

wherein $R^1$, $R^2$, $R^3$, $R^4$ and X have the same meanings as defined in claim 9.

11. The process of claim 10, wherein said compound represented by the formula (III) is prepared by condensing a baccatin compound represented by the formula (II):

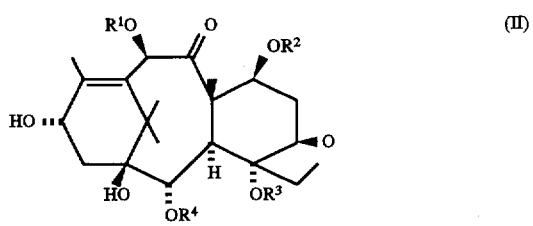

wherein $R^1$, $R^2$, $R^3$ and $R^4$ have the same meanings as defined in claim 10, and an epoxypropionic acid compound represented by the formula (I):

wherein X has the same meaning as defined in claim 10, or a reactive derivative thereof.

12. A process for preparing a 13α-(3-halogeno-2-hydroxypropionyloxy)baccatin compound represented by the formula (IV):

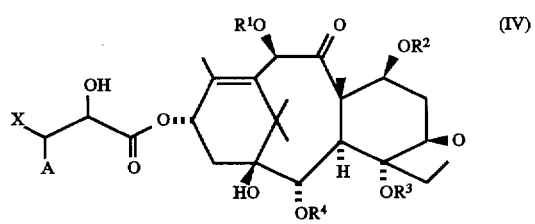

wherein $R^1$ represents a lower alkanoyl group or a protective group for hydroxy group; $R^2$ represents a protective group for hydroxy group; $R^3$ represents a lower alkanoyl group; $R^4$ represents a substituted or unsubstituted benzoyl group; X represents a substituted or unsubstituted aryl group, a substituted or unsubstituted lower alkenyl group, or a substituted or unsubstituted lower alkynyl group; and A represents a halogen atom, which comprises halogenating a 13α-epoxypropionyloxybaccatin compound represented by the formula (III):

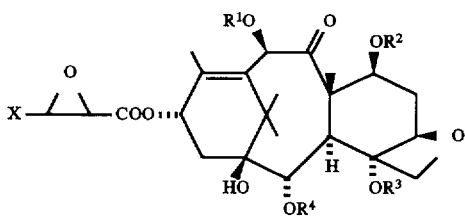

wherein $R^1$, $R^2$, $R^3$, $R^4$ and X have the same meanings as defined above.

13. The process of claim 12, wherein said compound represented by the formula (III) is prepared by condensing a baccatin compound represented by the formula (II):

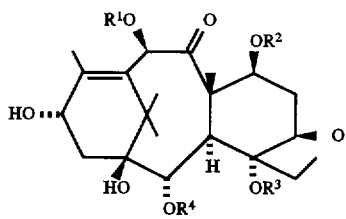

wherein $R^1$, $R^2$, $R^3$ and $R^4$ have the same meanings as defined in claim 12, and an epoxypropionic acid compound represented by the formula (I):

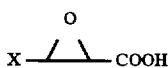

wherein X has the same meaning as defined in claim 12, or a reactive derivative thereof.

14. A process for preparing a 13α-epoxypropionyloxybaccatin compound represented by the formula (III):

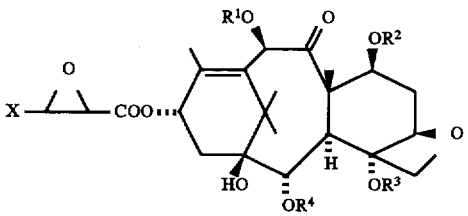

wherein $R^1$ represents a lower alkanoyl group or a protective group for hydroxy group; $R^2$ represents a protective group for hydroxy group; $R^3$ represents a lower alkanoyl group; $R^4$ represents a substituted or unsubstituted benzoyl group; and X represents a substituted or unsubstituted aryl group, a substituted or unsubstituted lower alkenyl group, or a substituted or unsubstituted lower alkynyl group, which comprises condensing a baccatin compound represented by the formula (II):

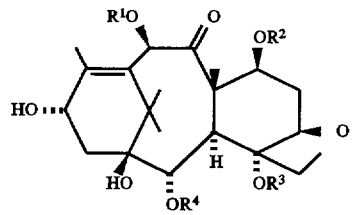

wherein $R^1$, $R^2$, $R^3$ and $R^4$ have the same meanings as defined above, and an epoxypropionic acid compound represented by the formula (I):

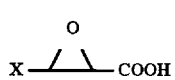

wherein X has the same meaning as defined above, or a reactive derivative thereof.

15. The process of any one of claims 1 to 14, wherein $R^1$ is a lower alkanoyl group, a trihalo-lower alkoxycarbonyl group or a tri-lower alkylsilyl group; $R^2$ is a trihalo-lower alkoxycarbonyl group or a tri-lower alkylsilyl group; $R^3$ is a lower alkanoyl group; $R^4$ is unsubstituted benzoyl group; and X is a substituted or unsubstituted phenyl group or an unsubstituted lower alkenyl group.

16. The process of claim 15, wherein $R^1$ is trichloroethoxycarbonyl group, $R^2$ is trichloroethoxycarbonyl group, $R^3$ is acetyl group, $R^4$ is benzoyl group, X is unsubstituted phenyl group and Y is bromine atom.

17. A process for preparing a taxol compound represented by the formula (IX):

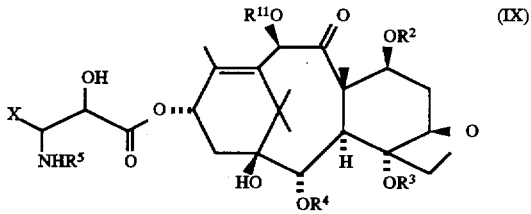

wherein $R^3$ represents a lower alkanoyl group; $R^4$ represents a substituted or unsubstituted benzoyl group; $R^5$ represents a substituted or unsubstituted lower alkoxycarbonyl group where said lower alkoxycarbonyl group may have a cycloalkyl portion, a substituted or unsubstituted lower alkanoyl group, a substituted or unsubstituted arylcarbonyl group or a substituted or unsubstituted aromatic heterocyclic group-substituted carbonyl group; $R^{11}$ represents a lower alkanoyl group or hydrogen atom; and X represents a substituted or unsubstituted aryl group, a substituted or unsubstituted lower alkenyl group, or a substituted or unsubstituted lower alkynyl group, which comprises reducing a 13α-(3-azido-2-hydroxypropionyloxy)baccatin compound represented by the formula (V):

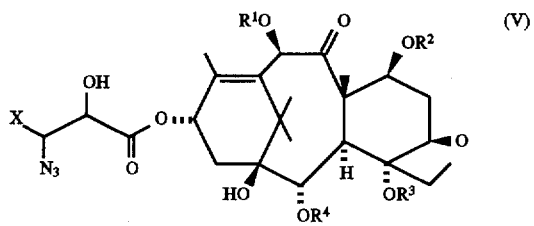

wherein R¹ represents a lower alkanoyl group or a protective group for hydroxy group; R² represents a protective group for hydroxy group; R³, R⁴ and X have the same meanings as defined above, or a salt thereof in the presence of a compound represented by the formula (VII):

wherein R⁵ has the same meaning as defined above, a salt thereof or a reactive derivative thereof, and removing a protective group from the resulting 13α-(3-acylamino-2-hydroxypropionyloxy)baccatin compound represented by the formula (VIII):

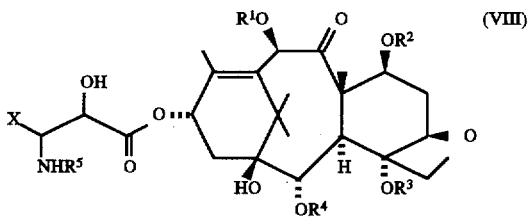

wherein R¹, R², R³, R⁴, R⁵ and X have the same meanings as described above.

18. A 13α-epoxypropionyloxybaccatin compound represented by the formula (III):

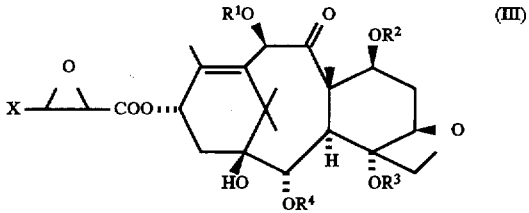

wherein R¹ represents a lower alkanoyl group or a protective group for hydroxy group; R² represents a protective group for hydroxy group; R³ represents a lower alkanoyl group; R⁴ represents a substituted or unsubstituted benzoyl group; and X represents a substituted or unsubstituted aryl group, a substituted or unsubstituted lower alkenyl group, or a substituted or unsubstituted lower alkynyl group.

19. A 13α-(3-halogeno-2-hydroxypropionyloxy)baccatin compound represented by the formula (IV):

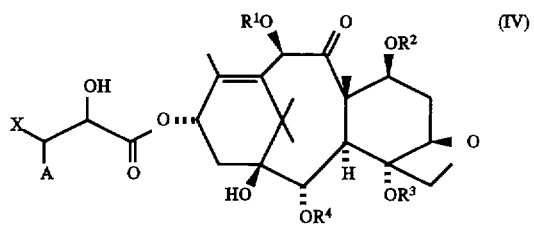

wherein R¹ represents a lower alkanoyl group or a protective group for hydroxy group; R² represents a protective group for hydroxy group; R³ represents a lower alkanoyl group; R⁴ represents a substituted or unsubstituted benzoyl group; X represents a substituted or unsubstituted aryl group, a substituted or unsubstituted lower alkenyl group, or a substituted or unsubstituted lower alkynyl group; and A represents a halogen atom.

20. A 13α-(3-azido-2-hydroxypropionyloxy)baccatin compound represented by the formula (V):

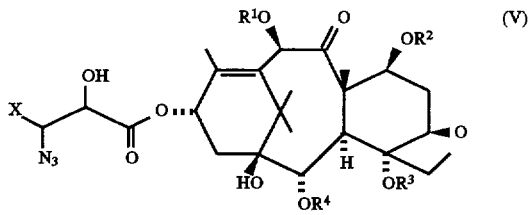

wherein R¹ represents a lower alkanoyl group or a protective group for hydroxy group; R² represents a protective group for hydroxy group; R³ represents a lower alkanoyl group; R⁴ represents a substituted or unsubstituted benzoyl group; and X represents a substituted or unsubstituted aryl group, a substituted or unsubstituted lower alkenyl group, or a substituted or unsubstituted lower alkynyl group.

21. A taxol compound represented by the formula (X):

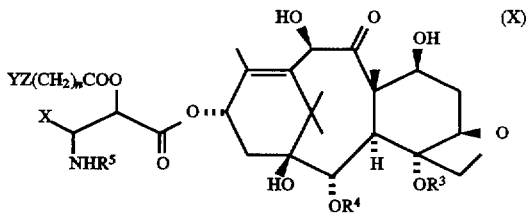

wherein R³ represents a lower alkanoyl group; R⁴ represents a substituted or unsubstituted benzoyl group; R⁵ represents a substituted or unsubstituted lower alkoxycarbonyl group where said lower alkoxycarbonyl group may have a cycloalkyl portion, a substituted or unsubstituted lower alkanoyl group, a substituted or unsubstituted arylcarbonyl group or a substituted or unsubstituted aromatic heterocyclic group-substituted carbonyl group; X represents a substituted or unsubstituted aryl group, a substituted or unsubstituted lower alkenyl group, or a substituted or unsubstituted lower alkynyl group; Y represents a residue obtained by removing hydroxy group from one carboxyl group of an amino acid or dipeptide where amino group and/or carboxyl group existing in said residue may be protected; Z represents a group represented by the formula of —O— or —NH—, and n represents an integer of 1 to 6, or a salt thereof.

22. A process as claimed in one of claims 1, 2, 3, 6, 7, or 8, further comprising reacting the 13α-(3-amino-2-hydroxypropionyloxy)baccatin compound represented by the formula (VI):

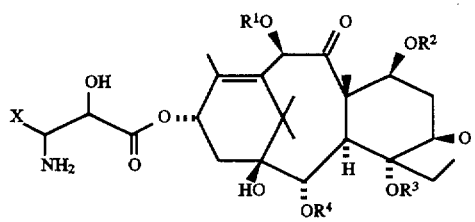

or a salt thereof, with a compound represented by the formula (VII):

a salt thereof or a reactive derivative thereof, wherein $R^5$ represents a substituted or unsubstituted lower alkoxycarbonyl group where said lower alkoxycarbonyl group may have a cycloalkyl portion, a substituted or unsubstituted lower alkanoyl group, a substituted or unsubstituted arylcarbonyl group or a substituted or unsubstituted aromatic heterocyclic group-substituted carbonyl group; and removing a protective group from the resulting 13α-(3-acylamino-2-hydroxypropionyloxy)baccatin compound represented by the formula (VIII):

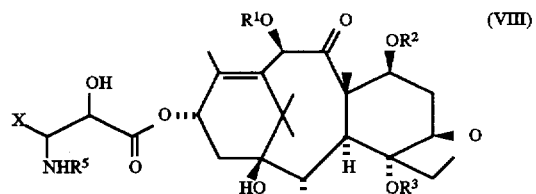

to form a taxol compound represented by the formula (IX):

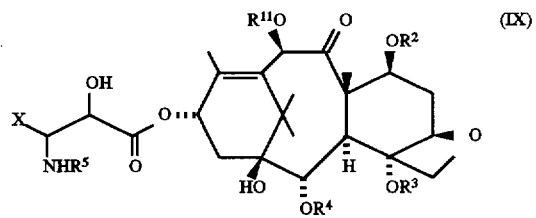

wherein $R^{11}$ represents a lower alkanoyl group or hydrogen atom;

wherein $R^1$, $R^2$, $R^3$, $R^4$, and X have the same meanings as defined above.

* * * * *